United States Patent [19]
Rohr et al.

[11] Patent Number: 5,998,224
[45] Date of Patent: Dec. 7, 1999

[54] MAGNETICALLY ASSISTED BINDING ASSAYS UTILIZING A MAGNETICALLY RESPONSIVE REAGENT

[75] Inventors: Thomas E. Rohr, Gurnee; Tuan A. Elstrom, Lake Bluff; Lawrence V. Howard, Libertyville; Eric B. Shain, Glencoe, all of Ill.

[73] Assignee: Abbott Laboratories, Abbott Park, Ill.

[21] Appl. No.: 08/857,440

[22] Filed: May 16, 1997

[51] Int. Cl.$^6$ .................................................. G01N 33/553
[52] U.S. Cl. .................... 436/526; 436/528; 436/534; 436/536; 436/538; 436/806; 435/7.1
[58] Field of Search .................... 436/526, 528, 436/534, 806, 536, 538; 422/236; 207/214; 435/7.1

[56] References Cited

U.S. PATENT DOCUMENTS

| | | |
|---|---|---|
| 3,985,649 | 10/1976 | Eddelman . |
| 4,070,246 | 1/1978 | Kennedy et al. . |
| 4,745,077 | 5/1988 | Holian et al. . |
| 4,960,691 | 10/1990 | Gordon et al. . |
| 5,076,950 | 12/1991 | Ullman et al. .................. 252/62.51 |
| 5,108,933 | 4/1992 | Liberti et al. . |
| 5,145,784 | 9/1992 | Cox et al. . |
| 5,236,824 | 8/1993 | Fujiwara et al. ..................... 435/5 |
| 5,252,459 | 10/1993 | Tarcha . |
| 5,322,756 | 6/1994 | Ziolo . |
| 5,350,676 | 9/1994 | Oberhardt et al. . |
| 5,358,659 | 10/1994 | Ziolo . |
| 5,374,531 | 12/1994 | Jensen . |
| 5,445,970 | 8/1995 | Rohr . |
| 5,445,971 | 8/1995 | Rohr . |

FOREIGN PATENT DOCUMENTS

| | | |
|---|---|---|
| 0 438 520 | 7/1991 | European Pat. Off. . |
| 9319370 | 9/1993 | WIPO . |
| 9319371 | 9/1993 | WIPO . |
| WO 94/20855 | 9/1994 | WIPO . |
| WO 95/04279 | 2/1995 | WIPO . |

OTHER PUBLICATIONS

D. Jiles, Introduction to Magnetism and Magnetic Materials, Chapman & Hall (London: 1991).

*Primary Examiner*—Jeffrey Stucker
*Attorney, Agent, or Firm*—David L. Weinstein

[57] ABSTRACT

Assay methods utilizing the response of a magnetically responsive reagent to the influence of a magnetic field to qualitatively or quantitatively measure binding between specific binding pair members. According to the invention, the presence of an analyte mediates whether or not the magnetically responsive reagent binds to a mobile solid phase reagent. The extent of binding will modulate the response of the magnetically responsive reagent or that of the mobile solid phase reagent, or both, to the influence of a magnetic field. Hence, by measuring the response to the magnetic field of the magnetically responsive reagent, or that of the mobile solid phase reagent, the presence or amount of analyte contained in a test sample can accurately be determined. The invention utilizes various devices to carry out the assay methods described.

44 Claims, 25 Drawing Sheets

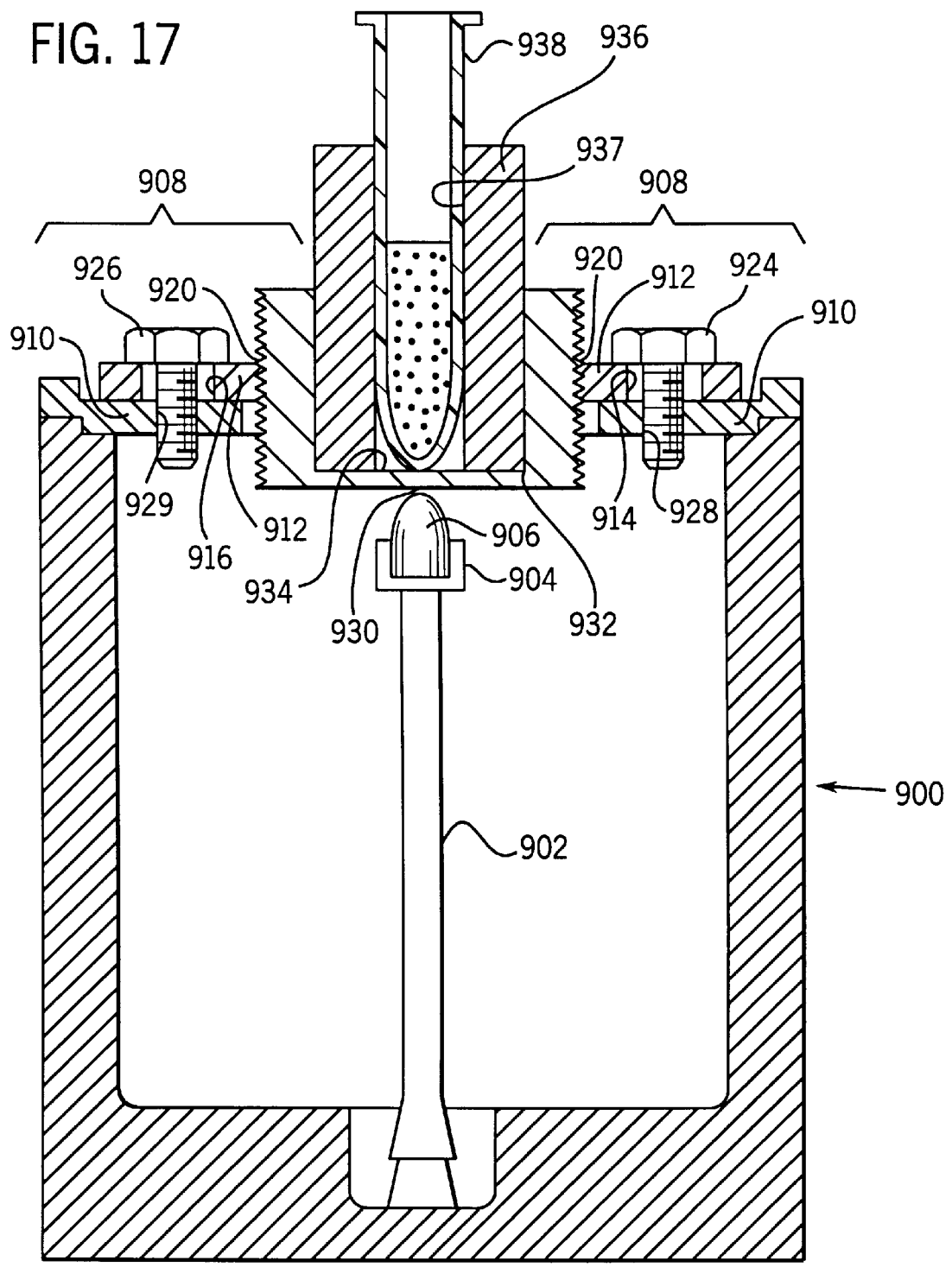

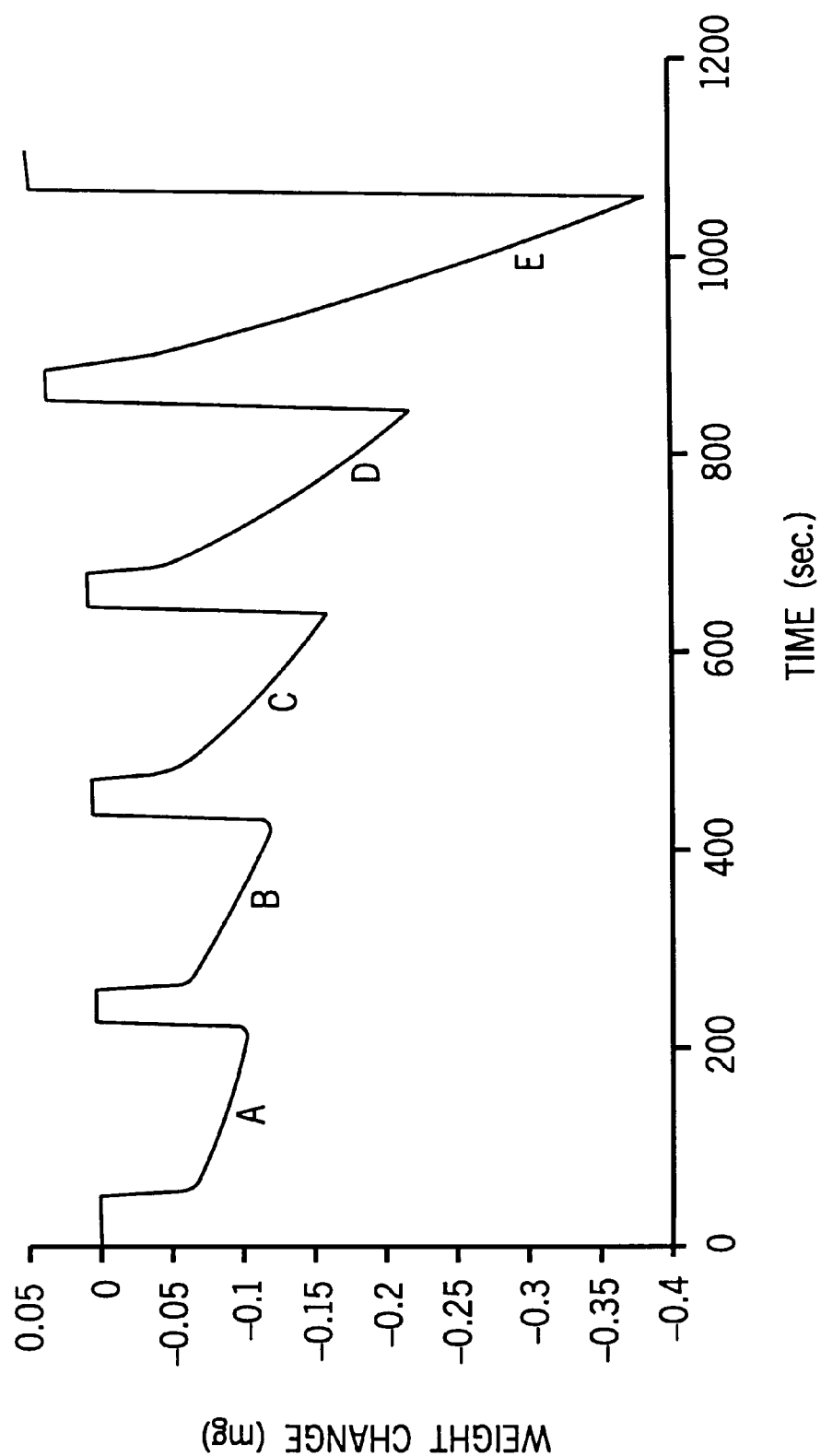

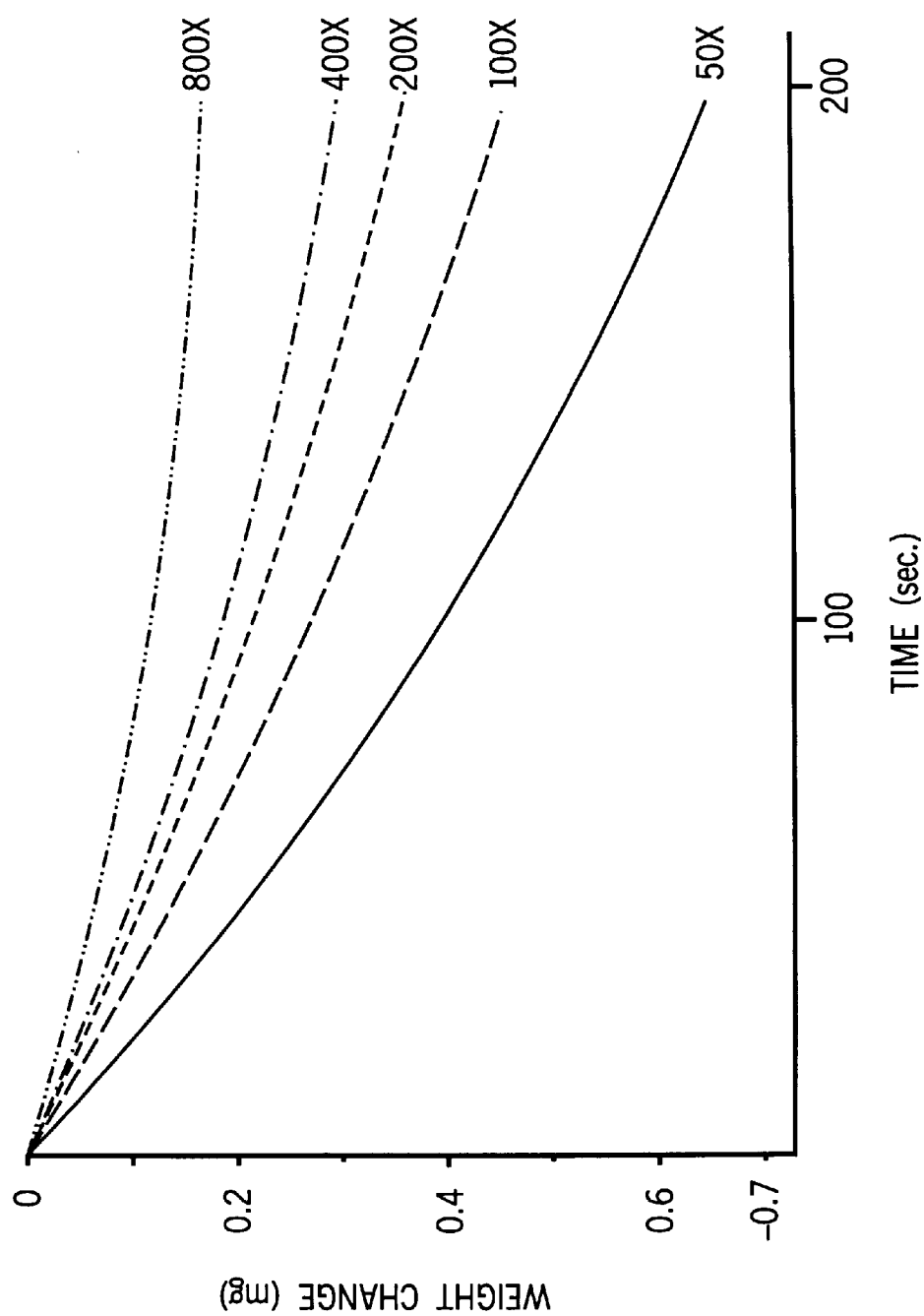

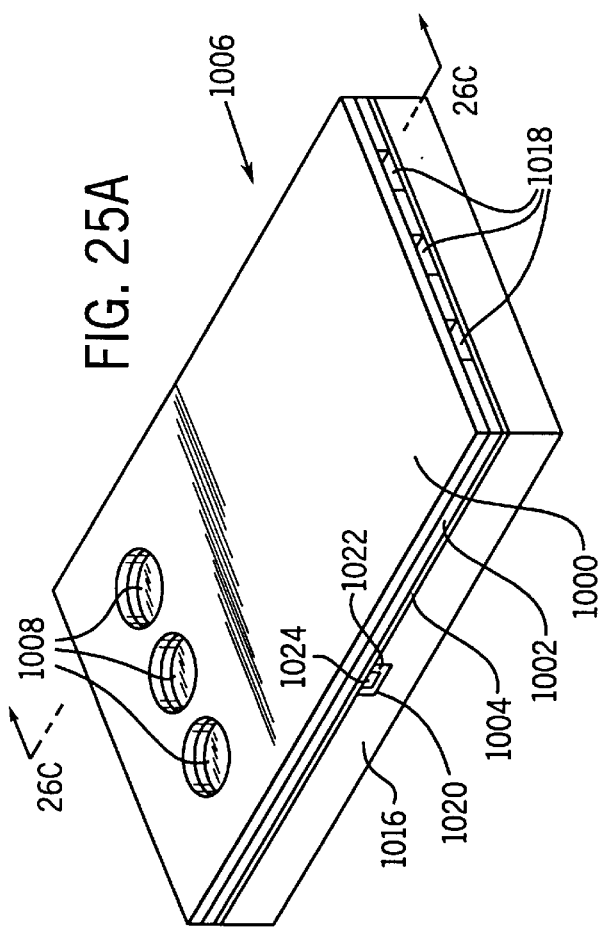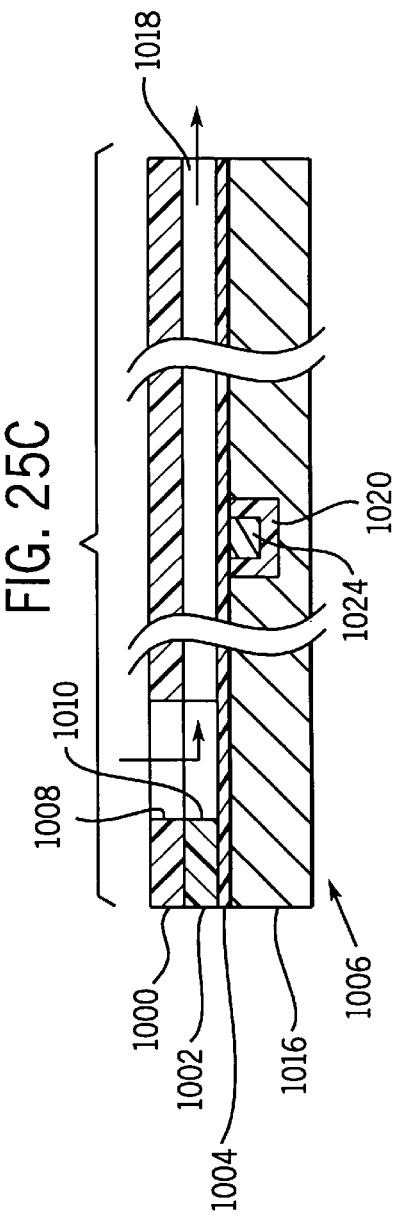

MAGNETICALLY ASSISTED BINDING ASSAYS UTILIZING A MAGNETICALLY RESPONSIVE REAGENT

BACKGROUND OF THE INVENTION

1. Field of the Invention

This invention relates to a method for determining the presence or amount of analyte in a test sample using magnetically responsive materials. More particularly, the invention relates to the use of magnetically responsive materials to change the properties of components in binding assays.

2. Discussion of the Art

Diagnostic assays have become an indispensable means for detecting analytes in test samples by using the mutual reaction between the analyte and a specific binding member for the analyte, such as the immunoreaction between an antigen and an antibody that binds to that antigen. Typically, detectable tags or labels attached to antibodies, which in turn bind to the analyte of interest, are employed in such diagnostic assays, wherein the detection of the resultant labeled antibody-analyte complex, or detection of the labeled antibody that does not bind to the analyte to form a complex, is used to indicate the presence or amount of analyte in the test sample.

Two commonly used diagnostic assay techniques employing specific binding members are the radioimmunoassay (RIA) and the enzyme immunoassay (EIA), both of which employ a labeled specific binding member. The RIA uses a radioactive isotope as the detectable tag or label attached to a specific binding member. Because the radioactive isotope can be detected in very small amounts, it can be used to detect or quantify small amounts of analyte. However, substantial disadvantages associated with the RIA include the special facilities and extreme caution that are required in handling radioactive materials, the high costs of such reagents, and their unique disposal requirements.

The EIA uses an enzyme as the detectable tag or label attached to a specific binding member, wherein the enzymatic activity of the enzyme is used to detect the immunoreaction. While the EIA does not have some of the same disadvantages of the RIA, EIA techniques typically require the addition of substrate materials to elicit the detectable enzyme reaction. In addition, enzyme substrates are often unstable and have to be prepared just prior to use or be stored under refrigeration. Moreover, enzyme labels may be difficult to purify and conjugate to binding members, and may be unstable during storage at room temperature or even under refrigerated conditions. Enzyme immunoassays are also unsatisfactory in that the methods typically require complex incubations, multiple liquid additions, and multiple wash steps.

More recently, assay techniques using metallic sol particles as visual labels have been developed. In these techniques, a metal (e.g., gold, silver, platinum), a metal compound, or a nonmetallic substance coated with a metal or a metal compound, is used to form an aqueous dispersion of particles. Generally, the specific binding member to be labeled is adsorbed onto the metallic sol particles, and the particles are captured or aggregated in the presence of analyte. Although the metallic sol particles have the advantage of producing a signal that is visually detectable as well as measurable by an instrument, they are difficult to measure quantitatively. The metallic sol particles also have a limited color intensity, and consequently, limited sensitivity in some assays. In addition, the surfaces of inorganic metallic sol particles, such as gold, may not readily accept the covalent attachment of specific binding members. Thus, during use in a binding assay, care must be taken so that the adsorbed specific binding members are not removed from the inorganic particles through the combination of displacement by other proteins or surface active agents and the shear forces that accompany washing steps used to remove non-specifically bound material. Metallic sol particles can be difficult to coat without inducing aggregation; they may aggregate upon storage or they may aggregate upon the addition of buffers or salts. Furthermore, such particulate labels are difficult to concentrate and can be difficult to disperse.

Other materials for labels include chemiluminescent and fluorescent substances. However, these substances can be unstable, and fluorescent materials may undergo quenching. Non-metallic particles, such as dyed or colored latex particles and selenium particles, have also been used as visual labels.

Self-performing immunoassay devices have proven to be of great benefit in the field of diagnostics. A self-performing immunoassay device is a kit containing immunoreagents to which a biological sample can first be added by the patient or laboratory technician, then the diagnostic assay performed without the need for complex laboratory instruments. Commercially available self-performing immunoassay devices, such as the strip assay device having the trademark "TESTPACK PLUS", distributed by Abbott Laboratories, enable immunoassays to be performed quickly and reliably.

Typically, self-performing immunoassay devices involve chromatographic test strips. For example, U.S. Pat. No. 4,960,691 discloses a test strip for analysis of an analyte in a sample by means of a sequential series of reactions. The test strip comprises a length of chromatographic material having capillarity and the capacity for chromatographic solvent transport of non-immobilized reagents and reactive components of a sample by means of a selected chromatographic solvent. The test strip includes (1) a first end at which chromatographic solvent transport begins, (2) a second end at which chromatographic solvent transport ends, and (3) a plurality of zones positioned between the first and second ends. These zones include (1) a first zone impregnated with a first reagent which is mobile in the solvent and capable of a specific binding reaction with the analyte, (2) a second zone for receiving the sample, and (3) a third zone, downstream of the second zone, impregnated with a second reagent that is immobilized against solvent transport and is capable of a specific binding reaction with the analyte so as to immobilize the analyte in the third zone. The test strip is designed so that the first reagent can be detected at the third zone as a measure of the analyte.

A common feature of chromatographic test strips involves the flow of a fluid or a mixture of a fluid and particles through a porous matrix. The test strip typically includes a reaction zone where binding reactions can occur. For proper binding reactions to occur in chromatographic test strips, the fluid or mixture must flow substantially uniformly through the reaction zone.

A problem with assay devices of this type is the inherent variability in the material from which the porous matrix is formed. This variability (for example, in porosity) directly affects the flow of fluid through the matrix and may adversely affect the precision of the assay device. Furthermore, the matrix will often non-specifically bind the particles or reagents at sites at the intended reaction zone or elsewhere, thereby necessitating the use of elaborate passivating procedures after the immobilized reagent has been applied. Consequently, there is a desire to develop a rapid, simple, self-performing assay device that does not require a fluid to flow through a porous matrix.

Another problem with self-performing immunoassay devices is the necessity of immobilizing a specific binding reagent on the test strip so that reagents involved in the assay can be captured at the reaction zone. The process of immobilizing the specific binding reagents on the test strip can be difficult to control, leading to lot-to-lot variations in the binding capacity of the reaction zone. Furthermore, the immobilized binding reagents can be unstable, causing the binding capacity of the reaction zone to change after shipping or storage. Because the immobilized specific binding reagent is specific for the assay of a particular analyte, test strips must be dedicated to a particular assay. An additional problem with self-performing immunoassay devices is lot-to-lot variation resulting from manufacturing processes, especially variation of the activity of the biological reagents, such as the binding molecules. For example, lot-to-lot variations in the binding capacity of the binding reagent at the capture zone of a test strip can affect assay results. Although adjustments in the activities or concentrations of the other reagents can compensate, making such adjustments involves introducing undue complexity to the manufacturing process and necessitates matching each lot of test strips to particular lots of reagents. The ability to use a completely stable, uniform test strip in assays for several different analytes would greatly simplify the production and control of strip-based self-performing assays. Alternatively, the ability to readily adapt a test strip during manufacturing to meet the requirements of a set of reagents would be advantageous.

In several applications it is desirable to use a self-performing assay which gives a positive result above a certain analyte concentration and a negative result below that concentration, with a very narrow range of transition concentrations. This result has been difficult to achieve with conventional test strips.

Superparamagnetic microparticles are also used extensively in the performance of immunoassays. Superparamagnetic microparticles are magnetically responsive in that an applied magnetic field will cause a force to act upon them in the direction of the magnetic field generator. However, they will not retain any residual magnetism after the applied magnetic field is removed. Typically, the particles are attached to a specific binding member to form a conjugate, the specific binding member being capable of binding to an analyte of interest. The specific binding member-particle conjugate is dispersed in a liquid, which is then mixed with the sample to form a test mixture, thereby allowing the specific binding member-particle conjugate to bind the analyte, if analyte is present. The conjugate-analyte complex is thee attracted to a solid surface by the application of a magnetic field and the material not bound to the conjugate is removed (commonly known as bound/free separation), as described in U.S. Pat. Nos. 4,745,077; 4,070,246; and 3,985, 649 . Additional wash steps, reagent additions, and bound/ free separations are usually required before a measurable signal is produced. Analytical methods of this type typically use light emission (chemiluminescence or fluorescence), light absorption after the enzymatic production of a chromophore, or radioactive emission as the signal indicative of the amount of the analyte of interest. Typically, the magnetic responsiveness of the superparamagnetic particles is used only as an aid in the bound/free separation steps, with the remainder of the assay procedure involving conventional reagents and protocols. Consequently, conventional analyses using superparamagnetic particles are limited to either complex automated instrumentation (for example, the ACS 180 from Ciba Corning Diagnostics) or an extended series of manual assay steps.

The size and composition of the superparamagnetic particles and the strength and gradient of the applied magnetic field will determine the magnitude of the magnetic force exerted upon them. When a magnetic field is applied to a liquid suspension of such particles, the magnitude of the force exerted on each particle, and the hydrodynamic drag of each particle, will determine its rate of movement through the liquid toward the magnetic field generator. For magnetically responsive particles of similar composition, the force exerted upon an individual particle by an applied magnetic field, and hence its rate of movement through the liquid, depends upon its volume, while drag is determined by its cross-sectional area. Smaller magnetically responsive particles will move more slowly in an applied magnetic field because of the weaker force exerted upon each particle relative to its cross-sectional area, and very small superparamagnetic particles such as ferrofluids will move very slowly because the force exerted on them is comparable to that of the random forces of the molecules surrounding them. These random forces result from thermal (Brownian) motion. As particles increase in size, their volume increases more rapidly than does their cross-sectional area, with the result that magnetic force increases more rapidly than does drag. The assembly of several small, slowly moving particles into aggregates will result in the sum of the forces acting upon the individual particles being exerted upon the aggregates, with the result that the aggregates will move more quickly through the liquid toward the source of the magnetic field than will the individual particles. The strength and gradient of the applied magnetic field can also be selected to favor the movement or capture of particular types or forms of magnetically responsive reagents.

U.S. Pat. No. 5,108,933 discloses a method whereby colloidal, magnetically responsive particles can be used for the separation of any one of a variety of target substances from a test medium suspected of containing the substance of interest through conversion of particles to micro-agglomerates including the target substance, via manipulation of their of their colloidal properties. The resultant agglomerates can subsequently be removed from the medium using ordinary laboratory magnets, as the particles are comprised of sufficient magnetic material, above an empirical threshold, to effect such removal. The method is carried out by adding to the test medium agglomerable and resuspendable colloidal particles, which are capable of stable suspension in the test medium, forming a magnetic agglomerate comprising the colloidal particles and any target substance present in the test medium, and separating the resulting magnetic agglomerates from the medium. This method of analysis, however, uses only a single type of particle, thereby presenting difficulties in detection. The presence or absence of aggregated magnetic particles in the vicinity of the magnet is neither easily nor precisely determined by visual means. It would be desirable to use indicator particles which could easily and accurately be detected visually.

The use of non-magnetic indicator particles is described by U.S. Pat. No. 5,374,531, which discloses the simultaneous use of magnetic particles and non-magnetic, fluorescent particles in the quantification of leukocyte phenotypes or other particulate analytes. Both the magnetic particles and the non-magnetic, fluorescent particles contain binding substances that bring about formation of rosettes consisting of magnetic particles, non-magnetic fluorescent particles, and the desired cells. The rosettes are separated from the non-magnetic components of the test sample by application of a magnetic field, whereupon the number of cells can be measured by the amount of fluorescence emitted by the non-magnetic, fluorescent particles. Rosette formation is applicable only to the detection of particulate analytes (such as cells), as it entails binding magnetic particles and indicator particles around the target cells, which cells must be of similar or greater size than the magnetic particles and the indicator particles. The rosettes described in this patent cannot be formed with molecular-scale analytes, as such analytes are much smaller than the magnetic particles and the indicator particles The aggregation of magnetic and non-magnetic indicator particles as a function of the presence of molecular-scale analytes is described in U.S. Pat. No. 5,145,784. In this patent, magnetic particles and nonmagnetic detectable particles which have antigen and/or antibody affixed to their surfaces are combined with the sample to be analyzed, free antibody if required, and any necessary buffers, salts, and other reagents. After incubation for a specific time and under conditions appropriate for antigen and specific antibody to bind, the magnetic particles are removed by attraction to a magnet. The presence or absence and/or quantity of non-magnetic detectable particles is subsequently determined and the presence or absence and/or quantity of antigen or antibody of interest in the sample is determined. In this process, the presence of analyte is not detected by directly observing the separated magnetic/nonmagnetic particle complexes near the location of the magnet.

U.S. Pat. Nos. 5,445,970 and 5,445,971 describe the use of a magnetically-attractable material as a detectable label in binding assays. The magnetic label is subjected to a magnetic field and the label, in turn, displays a resultant force or movement as a result of the application of the magnetic field. The extent of the force or movement is modulated by an analyte that may be present in a test sample. Because the presence or amount of analyte in a test sample is responsible for the magnitude of the force exerted or the amount of movement displayed by the magnetically-attractable material, the effect of the magnetic field on the magnetically-attractable label can be used as a measure of the presence or amount of analyte in a test sample. This approach requires that the presence of an analyte cause a change in the degree of binding of the magnetically-attractable material to a solid phase such that the bound magnetically-attractable material is prevented from moving in an applied magnetic field. Application of a magnetic field then causes a partitioning of the free magnetically-attractable material and the magnetically-attractable material bound to the solid phase. Measurement of the force exerted on the magnetically-attractable material bound to the solid phase, or on the free magnetically-attractable material, then reflects the quantity of analyte present in the test mixture. Although self-performing assay formats are possible using this approach, specific capture on some form of non-mobile solid phase is required.

For some applications, an assay format using only mobile solid phases such as microparticles would have distinct advantages, as would formats that do not require the measurement of magnetic force to determine analyte concentration. It would also be advantageous to utilize reagents that will not settle out of suspension. Latex particles that form stable suspensions can be produced, but superparamagnetic particles small enough to form stable suspensions, called ferrofluids, are only weakly attracted to the source of a magnetic field and therefore cannot be readily captured magnetically. Ferrofluids also are usually not compatible with aqueous solutions. It would be advantageous to develop self-performing immunoassay formats that do not require a chromatographic material. It would also be advantageous to develop a medium for a self-performing immunoassay that could be used for a multiplicity of immunoassays and easily adapted to reagent variations resulting from manufacturing processes.

SUMMARY OF THE INVENTION

The present invention involves a method for determining the presence or amount of an analyte in a test sample. In one embodiment, the method comprises the steps of:

(1) contacting said test sample with both a mobile solid phase reagent and a magnetically responsive reagent to form a reaction mixture, whereby said analyte becomes bound to both said mobile solid phase reagent and said magnetically responsive reagent to form a complex;

(2) subjecting said reaction mixture to a magnetic field such that a magnetic force is exerted upon said complex, the influence of said magnetic force being manifested by the movement or capture of said complex at a different rate from that of said magnetically responsive reagent alone or from that of said mobile solid phase reagent alone; and (3) measuring the degree of the manifestation to provide a measure of the presence or amount of said analyte in said test sample.

In a second embodiment, the method comprises the steps of:

(1) contacting said test sample with a magnetically responsive reagent and a mobile solid phase reagent to form a reaction mixture, whereby said analyte becomes bound to said magnetically responsive reagent to form a first complex comprising said magnetically responsive reagent and said analyte and said magnetically responsive reagent becomes bound to said mobile solid phase reagent to form a second complex comprising said magnetically responsive reagent and said solid phase reagent;

(2) subjecting said reaction mixture to a magnetic field such that a magnetic force is exerted upon said complexes, the influence of said magnetic force being manifested by the movement or capture of said second complex at a different rate from that of said magnetically responsive reagent alone or from that of said mobile solid phase reagent alone or said first complex; and (3) measuring the degree of the manifestation to provide a measure of the presence or amount of said analyte in said test sample.

In an alternative of the second embodiment, the method comprises the steps of:

(1) contacting said test sample with a magnetically responsive reagent and a mobile solid phase reagent to form a reaction mixture, whereby said analyte becomes bound to said mobile solid phase reagent to form a first complex comprising said mobile solid phase reagent and said analyte and said magnetically responsive reagent becomes bound to said mobile solid phase reagent to form a second complex comprising said magnetically responsive reagent and said solid phase reagent;

(2) subjecting said reaction mixture to a magnetic field such that a magnetic force is exerted upon said complexes, the influence of said magnetic force being manifested by the movement or capture of said second complex at a different rate from that of said magnetically responsive reagent alone or from that of said mobile solid phase reagent alone or said first complex; and (3) measuring the degree of the manifestation to provide a measure of the presence or amount of said analyte in said test sample.

The magnetically responsive reagent comprises a specific binding member attached to a magnetically responsive material. The magnetically responsive reagent preferably comprises a first specific binding member attached to a superparamagnetic microparticle or a ferrofluid. The mobile solid phase reagent comprises a specific binding member attached to a mobile solid phase material. The mobile solid phase reagent preferably comprises a second specific binding member attached to a mobile solid phase particle, such as a polymeric microparticle or latex.

In the first embodiment, commonly known as the sandwich format, the first specific binding member is selected to specifically bind to the analyte, and the second specific binding member is selected to also specifically bind to the analyte such that both specific binding members can be bound to the analyte simultaneously. In the presence of the analyte or when the concentration of analyte is above a specified threshold, both the first and the second specific binding members specifically bind to the analyte to form a detectable amount of complex comprising the analyte, the first and second specific binding members, and the magnetically responsive reagent and the solid phase reagent to which the first and second specific binding members, respectively, are attached. In the absence of the analyte or when the concentration of analyte is below a specified threshold, the amount of complex containing both specific binding members formed will be below the threshold of the assay.

In a variation of this first embodiment, the mobile solid phase reagent can be replaced by a magnetically responsive reagent. In this variation, in the presence of the analyte or when the concentration of analyte is above a specified threshold, both the first and the second specific binding members specifically bind to the analyte to form a detectable amount of complex comprising the analyte, the first and second specific binding members, and the magnetically responsive reagents to which the first and second specific binding members, respectively, are attached. In the absence of the analyte or when the concentration of analyte is below a specified threshold, the amount of complex containing both specific binding members formed will be below the threshold of the assay.

In the second embodiment, commonly known as the competitive format, one of the specific binding members exhibits an epitope displayed by the analyte. One of the specific binding members is selected to bind to that epitope, which epitope is also displayed by the other specific binding member. In the absence of the analyte or when the concentration of analyte is below a specified threshold, the specific binding members bind to each other to form a complex comprising the specific binding members and the magnetically responsive reagent and the solid phase reagent to which the specific binding members are attached. In the presence of the analyte or when the concentration of analyte is above a specified threshold, one of the specific binding members binds to the analyte, thereby inhibiting the binding thereof to the other specific binding member and preventing formation of the complex containing the magnetically responsive reagent and the mobile solid phase reagent.

The method of the present invention advantageously uses the presence of the analyte to modulate the binding of particles of magnetically responsive reagent to particles of mobile solid phase reagent to form complexes. In an applied magnetic field, the complexes will display magnetic responses that are different from those magnetic responses of the individual particles of magnetically responsive reagent and from those magnetic responses of the individual particles of mobile solid phase reagent. Such analyte-modulated complex formation can take place between particles exhibiting very different degrees of magnetic responsiveness, for example between superparamagnetic and diamagnetic particles. The resulting complexes will, because of the presence of the superparamagnetic particles, be attracted to the source of a magnetic field. The responses of complexes containing a plurality of paramagnetic, superparamagnetic, or ferrofluid particles, or the like, resulting from complex formation can serve as a measure of the presence or amount of an analyte present in a test sample. The change in magnetic response of particles of magnetically responsive reagent and particles of mobile solid phase reagent resulting from formation of complexes containing these particles can be manifested as an altered rate of movement of either type of particle in the applied field, or as an altered rate of accumulation of either type of particle at a location near the source of an applied magnetic field, or as a detectable accumulation of particle-containing complexes at a location near the source of an applied magnetic field.

The present invention also provides devices for determining the presence or amount of an analyte in a test sample. One such device comprises (i) a reaction vessel where unbound magnetically responsive reagent and magnetically responsive reagent attached to a mobile solid phase reagent in the form of a complex are produced in relation to the amount of analyte in the test sample; (ii) a magnetic field generator for the application of a magnetic field to the test mixture; and (iii) a measurement means to assess the altered responsiveness of the magnetically responsive reagent or the mobile solid phase reagent or both as a measure of the presence or amount of the analyte in the test sample. Magnetic field generators suitable for this invention include permanent magnets and electromagnets. Preferred measurement means for the devices of this invention comprise one or more of the following elements:

(1) a balance device for measuring the extent of complex formation by measuring the variation in the force exerted upon the reagents by an applied magnetic field or the variation in force exerted upon the source of the magnetic field by the reagents during or following magnetic separation of the complexes;

(2) a visual device for measuring the extent of complex formation by magnetic separation of unbound reagents from reagents in complexes;

(3) a visual device, or an optical device, for measuring (a) the extent of complex formation by magnetic capture of magnetically responsive reagent bound to a mobile solid phase reagent and the separation of unbound magnetically responsive reagent or the mobile solid phase reagent or (b) both reagents by movement in a capillary channel;

(4) a Hall Effect Transducer or other device for measuring the extent of complex formation by measuring perturbation of a magnetic field caused by changes in the distribution of the complexes during or following magnetic separation of the complexes;

(5) an optical device for measuring the extent of complex formation by measuring the variation in the optical density of the reaction mixture during or following magnetic separation of the complexes;

(6) an optical device for measuring the extent of complex formation by measuring the change in reflectivity of an optically reflective surface due to the force exerted upon it by magnetically captured complexes during or following magnetic separation of the complexes.

In an embodiment of a self-performing immunoassay device that can be used to replace a conventional strip device for performing immunoassays, specific binding members similar to those fixed to the porous matrix of a conventional self-performing immunoassay device are fixed to particles of magnetically responsive material, e. g., superparamagnetic particles, and the resulting magnetically responsive reagent is included in a mixture of reagents. The test sample is allowed to contact the mixture of reagents to form a test mixture, which is allowed to flow through a channel rather than through a porous matrix. Binding that would normally occur between visible indicator particles and the specific binding members non-diffusively attached to the porous matrix in the reaction zone of a conventional device can occur instead between magnetically responsive reagent and visible, diamagnetic indicator reagent. The placement of a magnet at a specified location along the channel attracts the magnetically responsive reagent bound to the diamagnetic indicator reagent. The presence of bound diamagnetic indicator reagent attracted to the magnet can be detected visually or by an optical device and indicates the presence or amount of analyte in the sample. It should also be noted that assays utilizing the principles of this invention can also be conveniently carried out in conventional reaction vessels, e. g., cuvettes, wells, tubes, and the like. It should further be noted that the magnetically responsive reagent can be visible and the diamagnetic reagent can be transparent, i. e., non-visible, whereby the presence or amount of analyte can be detected visually or by an optical device by viewing the accumulated magnetically responsive reagent only. In addition, both the magnetically responsive reagent can be visible and the diamagnetic reagent can be visible, whereby the presence or amount of analyte can be detected visually or by an optical device by viewing the accumulated magnetically responsive reagent and the visible diamagnetic reagent.

A particular advantage of this invention is the ease with which an immunoassay may be performed by means of a hand-held, self-contained device. The magnetic field of ordinary magnetic recording tape or credit card magnetic strips is sufficient to cause the separation of complexes containing magnetically responsive reagent from diamagnetic mobile solid phase reagent. The presence of these complexes may easily and reliably be observed visually on account of the presence of the diamagnetic solid phase material within the complexes. Another particular advantage of this invention is the ability to create a magnetic capture zone that will be matched to the magnetically responsive reagents and mobile solid phase reagents employed. The magnetic field and its gradient can be defined so as to provide optimal attraction of the magnetically responsive reagent. The magnetic capture site(s) can be used to provide semi-quantitative readings by visual means in self-performing assays. The magnetic capture site(s) can be controlled to provide means to compensate for lot-to-lot variations in assay reagents. As stated previously, the reagents used in conventional binding assays are usually complex biologic mixtures and tend to vary from one lot to another because of manufacturing processes. For sandwich assay formats, where particles of the magnetically responsive reagent may be very small relative to the particles of the mobile solid phase reagent, it is possible to control the magnetic behavior of the magnetically responsive reagent by controlling the strength and gradient of the magnetic field. It is also possible to control the capture of the particles of the mobile solid phase reagent that may be large relative to the particles of the magnetically responsive reagent. In order to most efficiently capture the complexes comprising particles of mobile solid phase reagent and particles of magnetically responsive reagent without capturing the unbound particles of magnetically responsive reagent, it is possible to provide a field gradient that changes with distance comparable to the dimension of the particles of mobile solid phase reagent. Such a field can be encoded into a magnetically susceptible material during manufacture.

BRIEF DESCRIPTION OF THE DRAWINGS

FIG. 17 is a schematic view of an apparatus utilizing a microbalance and test mixture positioning device for the magnetically assisted detection of complexes containing a magnetically responsive reagent.

FIG. 21 is a graph illustrating the results of magnetic separation as detected by the apparatus shown in FIGS. 4, 5, and 17 after incubation of anti-biotin coated polypyrrole with different amounts of biotin-bovine serum albumin coated ferrofluid.

FIG. 23 is a graph illustrating the rate and extent of apparent weight change of a magnet resulting from operation of the apparatus of FIG. 17 to measure the effect of varying the concentration of diluted solutions of biotinylated BSA coated ferrofluid.

FIG. 25A is a perspective view of a self-performing immunoassay device for the magnetically assisted detection of complexes containing a magnetically responsive reagent.

FIG. 25C is a side view in elevation of the self-performing immunoassay device of FIG. 25A.

DETAILED DESCRIPTION OF THE INVENTION

Figure 1:
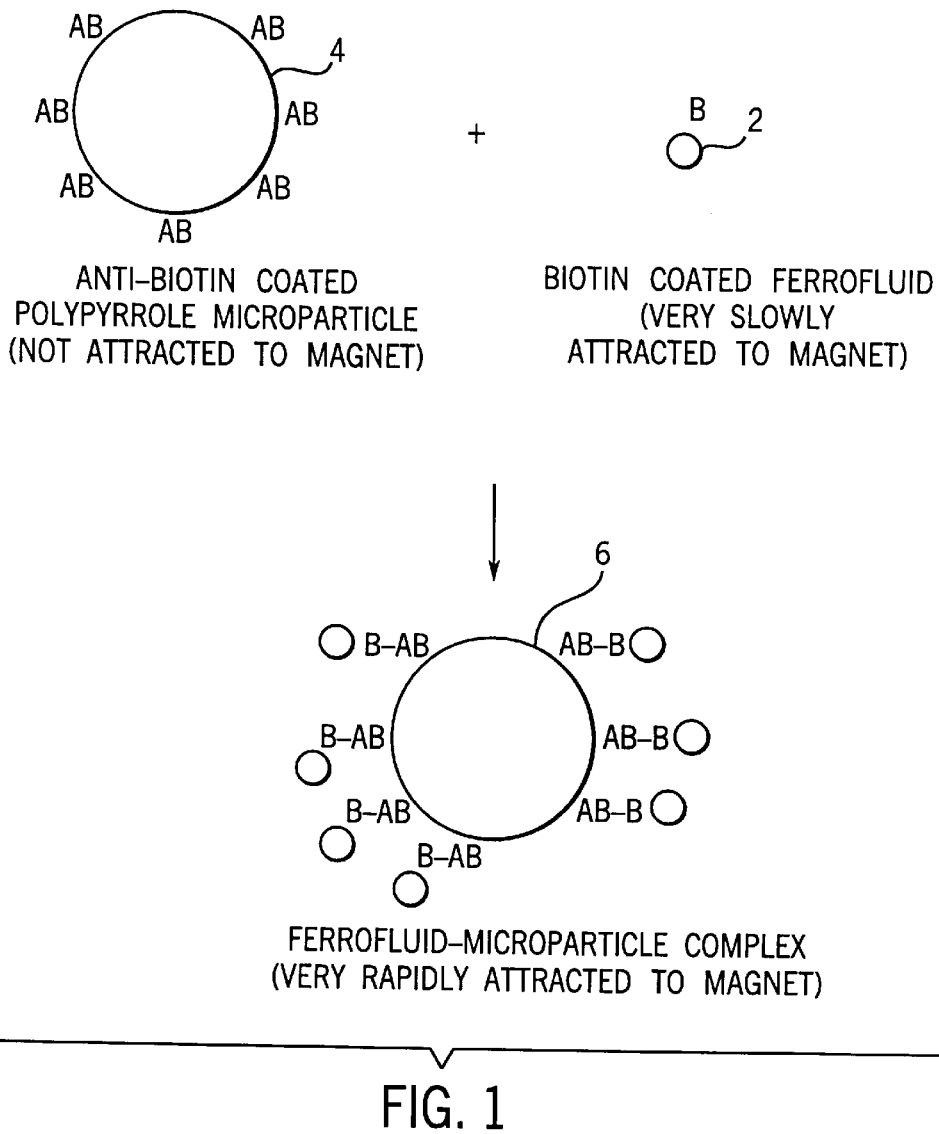
FIG. 1 is a schematic view of a specific binding reaction that is utilized in this invention.

The following definitions are applicable to the invention:

The expression "test sample", as used herein, refers to a material suspected of containing the analyte. The test sample can be used directly as obtained from the source or following a pre-treatment to modify the character of the sample. The test sample can be derived from any biological source, such as a physiological fluid including, but not intended to be limited to, blood, saliva, ocular lens fluid, cerebral spinal fluid, sweat, urine, milk, ascites fluid, mucous, synovial fluid, peritoneal fluid, amniotic fluid and the like; fermentation broths; cell cultures; chemical reaction mixtures and the like. The test sample can be pretreated prior to use, such as preparing plasma from blood, diluting viscous fluids, and the like. Methods of treatment can involve filtration, distillation, concentration, inactivation of interfering components, and the addition of reagents. In addition to biological or physiological fluids, other liquid samples can be used such as water, food products and the like for the performance of environmental or food production assays. In addition, a solid material suspected of containing the analyte can be used as the test sample. In some instances, it may be beneficial to modify a solid test sample to form a liquid medium or to release the analyte.

The expression "specific binding member", as used herein, refers to a member of a binding pair, i.e., two different molecules wherein one of the molecules specifically binds to the second molecule through chemical or physical means. In addition to the well-known antigen and antibody binding pair members, other binding pairs include, but are not intended to be limited to, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), sugar and boronic acid, and similar molecules having an affinity which permits their association in a binding assay. Furthermore, binding pairs can include members that are analogs of the original binding member, for example an analyte-analog or a binding member made by recombinant techniques or molecular engineering. If the binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other binding members. The details of the preparation of such antibodies, peptides and nucleotides and their suitability for use as binding members in a binding assay are well-known to those skilled-in-the-art.

The term "analyte" or "analyte of interest", as used herein, refers to the compound or composition to be detected or measured and which has at least one epitope or binding site. The analyte can be any substance for which there exists a naturally occurring binding member or for which a binding member can be prepared. Analytes include, but are not intended to be limited to, toxins, organic compounds, proteins, peptides, microorganisms, amino acids, carbohydrates, nucleic acids, hormones, steroids, vitamins, drugs (including those administered for therapeutic purposes as well as those administered for illicit purposes), virus particles and metabolites of or antibodies to any of the above substances. For example, such analytes include, but are not intended to be limited to, ferritin; creatinine kinase MIB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetylprocainamide (NAPA); procainamide; antibodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti hepatitis B core antigen IgG and IgM (Anti-HBC); human immune deficiency virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryonic antigen (CEA); and alpha fetal protein (AFP); and drugs of abuse and controlled substances, including but not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methaqualone; opiates such as heroin, morphine, codeine, hydromorphone, hydrocodone, methadone, oxycodone, oxymorphone and opium; phencyclidine; and propoxyphene. The term "analyte" also includes any antigenic substances, haptens, antibodies, macromolecules and combinations thereof.

The term "analyte-analogue", as used herein, refers to a substance which cross-reacts with an analyte-specific binding member, although it may do so to a greater or a lesser extent than does the analyte itself. The analyte-analog can include a modified analyte as well as a fragmented or synthetic portion of the analyte molecule, so long as the analyte-analogue has at least one epitopic site in common with the analyte of interest. An example of an analyte-analogue is a synthetic peptide sequence which duplicates at least one epitope of the whole-molecule analyte so that the analyte-analogue can bind to an analyte-specific binding member.

The term "magnetic", as used herein, pertains to a substance that has the capability of becoming magnetized when it is in a magnetic field.

The term "paramagnetic", as used herein, pertains to a substance in which an induced magnetic field is in the same direction as the magnetizing field, but much weaker than in ferromagnetic materials. Ferromagnetic materials, such as iron, nickel, or cobalt, exhibit high magnetic permeability, the ability to acquire high magnetization in relatively weak magnetic fields, a characteristic saturation point, and magnetic hysteresis. The term "paramagnetic" pertains to a substance for which the magnetic susceptibility is positive.

The term "diamagnetic", as used herein, pertains to a substance in which an induced magnetic field is in the opposite direction to the magnetizing field. The term "diamagnetic" pertains to a substance for which the magnetic susceptibility is negative.

Magnetism in a material arises from the intrinsic electron spins of the atoms comprising it. The spins of unpaired electrons in elements such as iron impart a spin to the entire atom. When a magnetic field is applied to such material, the spins of the individual atoms will tend to align with the field to minimize their energy, creating a net magnetic moment. If the responsive atoms are packed closely together, as in ferromagnetic materials, they influence one another to form long range magnetic order. As the intensity of the applied field increases, the magnetization of a ferromagnetic material will increase until virtually all of the responding atoms are aligned, after which no further increase in magnetization will be observed and the material is said to be saturated. During a subsequent decrease in the strength of the applied field, ferromagnetic materials will demonstrate marked hysteresis, and after total removal of the applied field the material will preserve some of its long-range magnetic order and be permanently magnetized.

In some materials, which are referred to as paramagnetic, individual atoms that exhibit high magnetic responsiveness are surrounded by atoms of other elements that exhibit low magnetic responsiveness. When subjected to an applied magnetic field, the atoms exhibiting high magnetic responsiveness will align with the field, but they will not influence one another and will be incapable of forming long-range magnetic order. No pronounced saturation will be observed, and when the magnetic field is removed, no hysteresis will be demonstrated, as the spins of the individual atoms revert to random orientations and all residual magnetic moment is lost.

Superparamagnetic materials exhibit characteristics of paramagnetism and ferromagnetism. If small particles of ferromagnetic material are dispersed in a matrix that exhibits low magnetic responsiveness, the atoms within a single particle align and influence one another when in a field. They do not, however, influence the atoms of a neighboring particle, with the result that long-range magnetic order is not formed. Although superparamagnetic materials are capable of becoming more highly magnetized than paramagnetic materials when subjected to a magnetic field, superparamagnetic particles also show little residual magnetism after the magnetic field is removed.

Additional details concerning magnetism, ferromagnetism, paramagnetism, superparamagnetism, and diamagnetism can be found in Jiles, *Introduction to Magnetism and Magnetic Materials*, Chapman & Hall (London: 1991), incorporated herein by reference.

The expression "magnetically responsive reagent", as used herein, refers to a substance involving a magnetically responsive material attached to a specific binding member. The attachment may be effected by covalent or non-covalent binding means, linking arms, and the like. However, the method of attachment is not critical to the present invention. As used herein, a "magnetically responsive material" is a substance which, upon the application of a magnetic field, allows the magnetically responsive reagent to produce a detectable response that will be directly or indirectly related to the amount of analyte in the test sample. The specific binding member component of the reagent may be selected to directly bind the analyte or to indirectly bind the analyte by means of an ancillary specific binding member, which is described in greater detail hereinafter. Magnetically responsive reagents may be attached to ancillary specific binding members before, during or after contacting the magnetically responsive reagent with the test sample and/or other assay reagents. The expressions "specific binding member attached to a magnetically responsive particle", "specific binding member attached to a magnetically responsive material", "specific binding member attached to a magnetically responsive reagent", and similar terms are used to refer to the main characteristic of the magnetically responsive reagents of the present invention, i. e., the reagent produces a detectable response when subjected to a magnetic field.

The expression "solid phase", as used herein, refers to any material to which analyte, analyte complexes, or assay reagents become bound and from which unreacted assay reagents, test sample, or test solutions can be separated. The solid phase generally has a specific binding member attached to its surface to form a "solid phase reagent", that allows the attachment of the analyte, the magnetically responsive reagent, or another assay reagent. Specific binding members that are attached to the solid phase may be selected to directly bind the analyte or to indirectly bind the analyte by means of an ancillary specific binding member, which can be attached to the solid phase reagent before, during, or after contacting the solid phase reagent with the test sample and/or other assay reagents.

It will be understood, of course, that the solid phase may comprise multiple components and that the immobilized specific binding member can be bound directly to any or all components of the solid phase. For example, a multiple component solid phase can include a solid phase reagent that is physically entrapped or retained and immobilized within a second or supplementary component of the solid phase by a physical, chemical, or biochemical means. As a further example, an analyte-specific binding member can be attached to insoluble microparticles, which are subsequently retained by a porous material. By "retained" it is meant that the microparticles, once on the porous material, are not capable of substantial movement to positions elsewhere within the porous material. A first solid phase component, which itself can be a solid phase reagent, can be retained by a supplementary component of the solid phase before, during, or after contacting the first solid phase component with the test sample and/or other assay reagents. In most embodiments, however, the specific binding member is bound or attached to a single solid phase component prior to contacting the thus formed mobile solid phase reagent with the test sample or other assay reagents. The solid phase reagents of this invention exhibit an insubstantial level of magnetic responsiveness.

The term "complex", as used herein, refers to the substance formed by the joining of one or more materials to another material by means of one or more specific binding reactions. Representative examples of complexes include, but are not limited to, (a) complexes formed by the specific binding reaction of a magnetically responsive reagent with a mobile solid phase reagent, (b) complexes formed by the specific binding reaction of an analyte with both a magnetically responsive reagent and a mobile solid phase reagent, (c) complexes formed by the specific binding reaction of an analyte with a magnetically responsive reagent, and (d) complexes formed by the specific binding reaction of an analyte with a mobile solid phase reagent.

The expression "ancillary binding member", as used herein, refers to any member of a binding pair which is used in the assay in addition to the specific binding members of the magnetically responsive reagent or mobile solid phase reagent. For example, in instances where the analyte itself cannot directly attach to the magnetically responsive reagent, an ancillary binding member can be capable of binding the magnetically responsive reagent to the analyte of interest. As it will be understood, of course, one or more ancillary binding members can be used in an assay and such ancillary binding member(s) can be attached to the magnetically responsive reagent or mobile solid phase reagent either before, during, or after the magnetically responsive reagent or mobile solid phase reagent is contacted with a test sample or other assay reagent. The ancillary binding member can be incorporated into the assay device or it can be added to the device as a separate reagent solution.

Description of the Invention

When a material is placed under the influence of a magnetic field, a force will act upon it, which force is directed towards or away from the source of the magnetic field. For example, the force acting on a strongly magnetically responsive ferromagnetic material, such as magnetite, will be directed toward the source of the magnetic field. In the same field, the much weaker force acting on a diamagnetic material, such as polystyrene, will be directed away from the source of the magnetic field. The extent of the response of magnetically responsive materials can be used as a measure of the amount of magnetically responsive material present. The present invention results from the unexpected and surprising discovery that, when a magnetically responsive material is used as a component of a magnetically responsive reagent in a binding assay, it is possible to detect the presence or amount of either or both of the free magnetically responsive material or magnetically responsive material incorporated into a complex by measuring the extent of the response resulting from the interaction of the magnetically responsive reagent with an applied magnetic field. The response of the magnetically responsive reagent to a magnetic field can manifest itself in ways such as, for example, a detectable movement of the magnetically responsive material or a detectable resultant force exerted by or upon the magnetically responsive material. Furthermore, the strength of the force or the extent of movement bears a definite relationship to the amount of the magnetically responsive material bound to a solid phase material, thereby permitting a determination of the presence or amount of an analyte in a test sample. For example, the force exerted by a magnetic field on individual particles of a ferromagnetic material suspended in a fluid (e. g., a ferrofluid) is relatively small, and consequently, difficult to detect. However, when a plurality or multiplicity of these individual ferromagnetic particles become attached to a diamagnetic solid phase material, e. g., by specific binding either directly via specific binding members or indirectly by simultaneously specifically binding to an analyte via specific binding members, the force exerted by a magnetic field on the individual complexes suspended in the fluid is relatively high, and consequently, much more readily detectable. The separation of individual particles from complexes and movement of complexes in a magnetic field forms the basis for the method and apparatus of this invention.

Assay Reagents

The selection of a particular composition of magnetically responsive material is not critical to the present invention. Preferably, the magnetically responsive material can be attached to or can be modified so as to be capable of being attached to a specific binding member that will in turn bind another assay reagent or a component present in a test sample. It is also preferred that the magnetically responsive material be magnetically responsive to an extent that permits partitioning of the bound magnetically responsive reagent and the unbound magnetically responsive reagent and the production of a detectable response upon being subjected to a magnetic field. For the purposes of the present invention, a material is magnetically responsive if it is influenced by the application of a magnetic field, such as, for example, if it is attracted to the source of the magnetic field or has a detectable magnetic susceptibility. A variety of different magnetically responsive reagents can be formed by varying either the magnetically responsive component or the specific binding member component of the reagent. It will be understood, of course, that the choice involves consideration of the analyte to be detected and the desired optimization of the assay technique.

A wide variety of magnetically responsive materials that are suitable for use in magnetically responsive reagents are commercially available or the production techniques therefor are well-known in the art. Preferred characteristics of magnetically responsive materials can be achieved by a wide variety of magnetic materials. Magnetically responsive materials suitable for use in this invention include, but are not limited to, ferromagnetic, ferrimagnetic, paramagnetic, superparamagnetic materials, and the like. The term "ferromagnetic" is generally used to describe materials that are attracted to a magnet and that typically become permanently magnetized upon exposure to a magnetic field. Ferromagnetic materials may also be reduced in particle size such that each of the particles is a single magnetic domain. These particles can be dispersed in a matrix to create a microparticle or a ferrofluid particle. In this state of subdivision, the material may be referred to as "superparamagnetic", and is characterized by the absence of any significant permanent measurable magnetization. Materials suitable for use as a matrix in this invention include, but are not limited to, materials such as, for example, organic polymers, including polystyrene, and the like.

Suitable ferromagnetic, ferrimagnetic, paramagnetic, and superparamagnetic materials include, but are not limited to, metals, such as iron, nickel, cobalt, chromium, manganese, and the like; lanthanide series elements, such as neodymium, erbium, and the like; alloys, such as magnetic alloys of aluminum, nickel, cobalt, copper, and the like; oxides, such as ferric oxide ($Fe_3O_4$), g-ferric oxide ($g-Fe_3O_4$), chromium oxide ($CrO_2$), cobalt oxide (CoO), nickel oxide ($NiO_2$), manganese oxide ($Mn_2O_3$), and the like; composite materials, such as ferrites and the like; and solid solutions, such as magnetite with ferric oxide and the like. Preferred magnetically responsive materials for use in this invention are magnetite, ferric oxide ($Fe_3O_4$), and ferrous oxide ($Fe_2O_3$).

Solid particles can be made of iron, iron oxide, a core of magnetically responsive material coated with a metal oxide, or a colloidal magnetic particle containing magnetite or hematite. Solid particles typically have a specific gravity of up to 8 and an average size, e. g., diameter, of up to 800 nanometers.

Layered particles can comprise a core of magnetically responsive material having a magnetically non-responsive coating. For example, a layered particle can comprise a core of magnetic metal oxide that is generally surrounded by a polymeric silane coat; a layered particle can comprise a water-insoluble metallic substrate coated with a condensation product of an aminobenzoic acid with an aldehyde, suitable for coupling to a compound having biological affinity. A layered particle can comprise a core formed of a single particle of a magnetically responsive material having a coating of a water-insoluble, cross-linked polymeric material that has reactive groups at the surface thereof. A layered particle can comprise a core of a non-magnetic material having a coating of a magnetically responsive material. A layered particle can comprise an organic polymeric particle having a ferrite coating; a layered particle can comprise a core of thermoplastic material having a coating of a magnetically responsive material (on at least a portion of the surface of the core); a layered particle can comprise a metal-coated polyaldehyde microsphere; a layered particle can comprise a core of a polymeric particle (e.g., polystyrene) having a magnetically responsive metal oxide/polymeric coating uniformly covering the core. A layered particle can comprise a core of a magnetically non-responsive material having a layer of a magnetically responsive material and a magnetically non-responsive coating. For example, a layered particle can comprise an agarose-encapsulated metal-coated polyaldehyde microsphere, a thermoplastic resin bead (e.g., polystyrene, polyvinyl chloride, polyacrylate, nylon, etc.) having from 1–25% by weight of a magnetically responsive powder bound on the surface of the bead, and a polymer coated thereon, the coated polymer having functional groups to bind a biologically active component.

Composite particles can comprise a magnetically responsive material embedded within a magnetically non-responsive material. Representative examples of composite particles include: (a) iron-containing magnetic crystals (<1000 Å) incorporated within a glass and/or crystal structure; (b) a copolymer matrix formed from at least one monoethylenic monomer (30–99% by weight) that does not coordinate with a metal complex, at least one crosslinkable polyethylenic monomer (0.5–50% by weight) that does not coordinate with a metal complex, and at least one nucleophilic monomer (0.5–30% by weight) that can be coordinated with a metal complex, with encapsulated crystallites of a metal; (c) magnetizable particles having an average size (e. g., diameter) less than 300 Å, encapsulated in an organpolysiloxane matrix; (d) a particulate reaction product of a water-soluble form of iron and a water-soluble polymer having available coordination sites (free electron pair for a coordinate bond with a transition metal atom); (e) an organic, inorganic, or synthetic polymeric matrix containing a magnetically responsive material; (f) a continuous phase of a water-insoluble polymeric matrix having dispersed (embedded) therein: a magnetically responsive material, and a particulate absorbent material (selected from charcoal, talc, ion exchange resins, Fuller's earth, silicon dioxide, oxides of zirconium or aluminum or titanium, porous glass, zeolites, natural or synthetic polymers, polymerized first or second antibodies or polymerized enzymes, cell surface antigens or receptors in a particulate form, subcellular particles and bacterial cells); (g) particles made by polymerizing one or more monomers in the presence of magnetically responsive solids to form directly a synthetic water-insoluble polymeric matrix having the solids uniformly embedded therein; (h) particles of cross-linked protein or polypeptide and a magnetically responsive material made by combining: an organic solvent solution of a high molecular weight polymer (e.g., polystyrene), a particulate magnetically responsive material, and a polyfunctional cross-linking agent (e.g., polyaldehyde); (i) hydrophobic vinyl aromatic polymeric particles having a mean diameter of from 0.03 to 5 micrometers and a magnetically responsive material in an amount from 0.5 to 50% by weight with respect to the polymeric portion of the particles, the magnetically responsive material being dispersed within the polymeric particles; (j) a filler selected from the group consisting of a metal, metal alloy, metal oxide, metal salt, metal sulfide, pigment and metallic chelate compound, and an oleophilic surface layer upon the filler, and a layer of polymeric material upon the oleophilic surface covering the filler.

Magnetically responsive reagents formed as matrix or composite particles may optionally include additional coatings or layers of magnetically responsive materials or magnetically non-responsive materials or mixtures thereof. Matrix compositions can be made by any of a variety of methods including, but not limited to, (1) polymerization of the magnetically responsive material with the selected monomer, (2) swelling of the matrix material with the introduction of the magnetically responsive material into pores within the matrix, and the like. The matrix can include organic and inorganic materials, such as, for example, glass, cellulose, synthetic polymeric materials, agarose, and the like. Polymeric materials suitable for this invention include, but are not limited to, polymers of styrene; substituted polystyrenes; polynaphthalene derivatives; polyacrylic and polymethacrylic acids; polyacrylamide and polymethacrylamide; polycarbonate; polyesters; polyamides; polypyrrole; polyaminoaromatic acids; polyaldehydes; proteinaceous materials, such as gelatin, albumin, and the like; polysaccharides, such as starch, dextran, and the like; and copolymers of polymeric materials. The polymer may also be used in an admixture with an inert filler or may include an absorbent material.

Preferably, particles of magnetically responsive material suitable for use in the present invention are substantially spherical in shape, although other shapes are suitable and may be advantageous in some circumstances. Other possible shapes include, but are not limited to, plates, rods, bars, and irregular shapes. The diameter of particles of magnetically responsive material preferably ranges from about 0.01 micron ($\mu$m) to about 1,000 $\mu$m, more preferably from about 0.01 $\mu$m to about 100 $\mu$m, and most preferably from about 0.01 $\mu$m to about 10 $\mu$m. As it will be appreciated by those skilled in the art, the composition, shape, size, and density of magnetically responsive material may vary widely and a magnetically responsive material can be selected based upon such factors as the analyte of interest and the desired assay protocol.

According to one embodiment of the present invention, particles of magnetically responsive material can be selected to have a specific gravity so as to remain suspended within the reaction mixture, thereby enhancing the reactivity of the specific binding member. Generally, small magnetically responsive particles having a mean diameter of less than about 0.03 $\mu$m (300 Å) can remain suspended in solution by thermal agitation without spontaneously settling. In alternative embodiments, particles of magnetically responsive material can be selected to have a specific gravity so as to settle in the reaction mixture, thereby enhancing the reactivity of the specific binding member with an immobilized reagent on a solid phase. Generally, large particles of magnetically responsive material, e. g., those having a mean diameter greater than about 10 $\mu$m, can respond to weak magnetic fields. Although large or dense particles of magnetically responsive material may be used, such particles may require that the reaction mixture be stirred or agitated during the incubation steps to inhibit settling of the particles. In another embodiment, particles of magnetically responsive material can be selected to remain dispersed in the reaction mixture for a time sufficient to permit the required binding reactions, without the need for stirring or mixing.

In forming the magnetically responsive reagent, the attachment of the binding member to the magnetically responsive material can be achieved by any suitable attachment or coupling mechanism, including, but not limited to, adsorption, covalent bonding, cross-linking (chemically or through binding members), a combination of such attachment mechanisms, and the like. Typically, coupling groups and coupling or linking agents are selected so that the binding activity of the specific binding member is not substantially modified or destroyed upon attachment to the magnetically responsive material. The quantity of binding member that can be attached to the magnetically responsive material is largely dependent upon its concentration, the conditions used, and the amount of and nature of the available functional groups on the magnetically responsive material or coupling agent.

Preferably, the specific binding member is covalently bonded to the magnetically responsive material, and the covalent bond may be formed between one component and a chemically active form of the other component. For example, an active ester such as N-hydroxysuccinimide can be introduced into one component and allowed to react with a free amine on the other component to form a covalent coupling of the two. Other examples include, but are not limited to, the introduction of maleimide to one component, which is then allowed to react with endogenous or introduced sulfhydryl moieties on the other component; the oxidation of endogenous or introduced carbohydrate groups on one component to form aldehydes, which can react with free amines or hydrazides on the other component. Where the magnetically-attractable label includes a polymeric coating or matrix, the polymer may be selected so that it contains, or can be provided with, suitable reactive groups such as, for example, azide, bromoacetyl, amino, hydroxyl, sulfhydryl, epoxide, carboxylic, or other groups to facilitate the attachment of the specific binding member. Suitable reagents, as well as conjugation techniques for synthesizing the magnetically responsive reagent, are well-known to those of ordinary skill in the art. It will be understood, of course, that the methods of synthesizing a magnetically responsive reagent are not intended to limit the invention.

The solid phase material and mobile solid phase reagents can generally comprise materials including, but not limited to, polymers, such as, for example, polymers of styrene; substituted polystyrene; polynaphthalene derivatives; polyacrylic and polymethacrylic acids; polyacrylamide and polymethacrylamide; polycarbonate; polyesters; polyamides; polypyrrole; polypropylene; latex; polytetrafluoroethylene; polyacrylonitrile; polycarbonate; glass or other vitreous materials; polyaminoaromatic acids; polyaldehydes; proteinaceous materials, such as gelatin, albumin, and the like; polysaccharides, such as starch, dextran, and the like; and copolymers of polymeric materials.

As further examples, natural, synthetic, or naturally occurring materials that are synthetically modified, can be used as a solid phase material. Examples of such materials include, but are not limited to, polysaccharides, such as cellulosic materials, including paper and the like, and derivatives of cellulose, such as cellulose acetate and nitrocellulose; silica; silicon particles; inorganic materials, such as deactivated alumina, or other inorganic finely divided material uniformly dispersed in a porous, polymeric matrix. The polymeric matrix can comprise polymers, such as polymers of vinyl chloride, copolymers of vinyl chloride and propylene, and copolymers of vinyl chloride polymer and vinyl acetate; naturally occurring and synthetic textiles, such as cotton, nylon, and the like; porous gels, such as silica gel, agarose, dextran, gelatin, and the like; polymeric films, such as polyacrylates and the like; protein binding membranes; and the like. The solid phase may also comprise microparticles, which can be selected from any suitable type of material including, but not limited to, polystyrene, polymethylacrylate, polyacrylamide, polypropylene, latex, polytetrafluoroethylene, polyacrylonitrile, polycarbonate, glass, and the like.

While the solid phase material preferably has a reasonable strength, or such strength can be provided by means of a support, the solid phase material preferably does not interfere with the production of a detectable signal. It will be understood, of course, that the solid phase material is typically exhibits relatively lower magnetic responsiveness than the magnetically responsive material and that its magnetic contribution to the assay is correctable by, for example, positioning such material in a manner where it is not substantially affected by a magnetic field. Alternatively, the effect of the solid phase material can be differentiated from that of the magnetically responsive material. As another alternative, such material can be demagnetized.

The means of attaching a specific binding member to a solid phase to thereby form a mobile solid phase reagent encompasses both covalent attachment and non-covalent attachment, which have been outlined previously with regard to synthesizing a magnetically responsive reagent. It is generally preferred that the specific binding member be attached to the solid phase by covalent attachment.

Assay Methods and Devices

The methods and devices of the present invention may be applied to any suitable assay format involving specific binding pair members including, but not limited to, those binding pair members previously described. The assay methods of the present invention utilize the response of a magnetically responsive reagent to the influence of a magnetic field to qualitatively or quantitatively measure binding between specific binding pair members. According to the present invention, the presence of an analyte mediates the extent to which the magnetically responsive reagent binds to a mobile solid phase reagent. The extent of binding will modulate the response of the magnetically responsive reagent or that of the mobile solid phase reagent, or both, to the influence of a magnetic field. Hence, by measuring the response of the magnetically responsive reagent, or that of the mobile solid phase reagent, or both, to the magnetic field, the presence or amount of analyte contained in a test sample can be accurately determined.

The magnetically responsive reagents and devices of the present invention can be used in a variety of immunoassay formats. The present invention, however, is not limited to immunoassays. In general, any assay configuration using specific binding pair members and a magnetically responsive reagent, such as, for example, the superparamagnetic microparticles used in the present invention, can be performed. Immunoassay formats are well-known to those of ordinary skill in the art, and are described, for example, in U.S. Pat. No. 5,252,459, all of which is incorporated herein by reference. Immunoassay formats are particularly well-described in column 5, line 55 through column 9, line 62 of U.S. Pat. No. 5,252,459.

The present invention is applicable to various competitive assay formats and sandwich assay formats that are well known in the art. Numerous competitive, inhibition, and sandwich assay formats have been described whereby a labeled reagent is partitioned between a liquid phase and a solid phase in relation to the presence of the analyte in the test sample.

According to a competitive assay format, a magnetically responsive reagent can comprise a first binding member (e. g., an analyte analogue) attached to a magnetically responsive material, to thereby form a magnetically responsive reagent. A mobile solid phase reagent can comprise a mobile solid phase material, such as a polymeric latex or microparticle, to which is attached a second binding member, which second binding member specifically binds the analyte and the first binding member, which is attached to the magnetically responsive reagent. During the course of the assay, an analyte in the test sample and the magnetically responsive reagent compete for binding sites on the mobile solid phase reagent. Alternatively, the specific binding member attached to the solid phase may be an analyte analogue selected to compete with the analyte for binding to a specific binding pair member attached to a magnetically responsive material. Hence, the quantity of magnetically responsive reagent that becomes bound to the solid phase is inversely proportional to the amount of analyte in the test sample.

According to a sandwich assay format, a first specific binding member is attached to a magnetically responsive material to form a magnetically responsive reagent and a second specific binding member is attached to a mobile solid phase to form a mobile solid phase reagent. The specific binding members are selected to directly or indirectly bind the analyte of interest. During the course of the assay, both the magnetically responsive reagent and the mobile solid phase reagent bind to the analyte to form a complex. Thus, the quantity of magnetically responsive reagent that forms a complex with the mobile solid phase reagent by binding to the analyte is proportional to the amount of analyte in the test sample.

According to the present invention, assay protocols may optionally comprise the use of ancillary binding members to indirectly bind the analyte or analyte analogue to the magnetically responsive reagent or to the mobile solid phase reagent. The ancillary binding member can be attached to a mobile solid phase reagent or to a magnetically responsive reagent before, during, or after contacting the mobile solid phase reagent or the magnetically responsive reagent with the test sample or other assay reagents.

In addition, the assay protocols may comprise, for example, contacting the assay reagents and test sample simultaneously to form a reaction mixture, or the assay reagents and test sample can be contacted sequentially, and for a time period suitable for binding, to form multiple reaction mixtures. According to such assay protocols, after a period suitable for binding to form complexes, the magnetically responsive reagent that has not undergone a specific binding reaction to form a complex (i. e., the unbound magnetically responsive reagent) can be separated from the magnetically responsive reagent that has undergone a specific binding reaction to form a complex (i. e., the bound magnetically responsive reagent) due to their different behavior in an applied magnetic field. It will be understood, of course, that the separation of the bound magnetically responsive reagent and the unbound magnetically responsive reagent may involve the complete removal of the unbound magnetically responsive reagent from the reaction mixture and/or from the bound magnetically responsive reagent.

The separation of the bound magnetically responsive reagent and the unbound magnetically responsive reagent may also involve the segregation of the unbound magnetically responsive reagent from the bound magnetically responsive reagent such that the unbound magnetically responsive reagent remains in the reaction mixture but does not adversely affect the detectable response when the bound magnetically responsive reagent is placed in the vicinity of a magnetic field. Alternatively, the unbound magnetically responsive reagent, the bound magnetically responsive reagent, or the mobile solid phase reagent can be observed for a response to a magnetic field. Further, the unbound magnetically responsive reagent, the bound magnetically responsive reagent, or the mobile solid phase reagent can be observed for a response to a magnetic field, whereby a ratio of the partitioning may be observed.

Generally, devices according to the present invention comprise components for performing magnetically assisted binding assays as taught herein. Accordingly, such devices preferably comprise (i) a reaction vessel; (ii) a magnetic field generator for the application of a magnetic field to the magnetically responsive reagent; and (iii) a measurement means to assess the effect of the magnetic field generated by the magnetic field generator on the magnetically responsive reagent or the mobile solid phase reagent, or both, as a measure of the presence or amount of analyte in the test sample.

The reaction vessel can be any device capable of containing the assay reagents disclosed herein and where the unbound magnetically responsive reagent and the bound magnetically responsive reagent can be produced in relation to the amount of an analyte in a test sample.

Separating the bound magnetically responsive reagent from the unbound magnetically responsive reagent can be accomplished by any means suitable for partitioning the unbound magnetically responsive reagent and the bound magnetically responsive reagent, such as, for example, application of a magnetic field.

The magnetic field generator can be any means for generating a magnetic field that elicits a response from the magnetically responsive reagent. Magnetic field generators preferred for this invention include permanent magnets and electromagnets. It will also be understood, of course, that the magnetic field generator may also be used to separate the unbound or free magnetically responsive reagent from the bound or complexed magnetically responsive reagent.

The response of a magnetically responsive reagent to a magnetic field can be manifested in many measurable forms including a resulting force or movement of the reagent such as, for example, an apparent change in force acting on the reagent in the reaction vessel, a displacement of the reagent, and the like. It will be understood, of course, that these manifestations can be measured directly by detecting and measuring the manifestations of the magnetically responsive reagent, or the manifestations can be measured indirectly by detecting and measuring the effect of the magnetically responsive reagent on, for example, the mobile solid phase reagent or the magnetic field generator. The influence of the magnetic field upon a magnetically responsive reagent may be observed or detected and measured by any means suitable for directly or indirectly measuring the response of the magnetically responsive reagent to the magnetic field. For example, (a) a change in the apparent weight can be detected and measured by a balance; (b) a change in apparent mass can be detected and measured by a balance or a resultant change in frequency of an oscillator, such as a quartz crystal; (c) a displacement can be detected and measured by an optical sensor to assess the magnitude of a change from an initial position to a subsequent position assumed by the magnetically responsive reagent, the mobile solid phase reagent, or the complex comprising a mobile solid phase reagent and a magnetically responsive reagent; (d) a movement can be detected and measured by motion detector to assess movement, such as, for example, a piezoelectrical film, or a coil, such as, for example, a susceptometer, which can create a field that is measurably disrupted by the presence and/or movement of magnetic material; and (e) a change in the amount of stress can be detected by incorporating stress sensitive materials into a vessel or solid phase material such that upon the application of a magnetic field, the change in stress will be detectable. It will be understood, of course, that depending upon the particular assay, it may be preferred to detect, directly or indirectly, the response of the unbound magnetically responsive reagent, the response of the bound magnetically responsive reagent, or both the response of the bound magnetically responsive reagent and the unbound magnetically responsive reagent to the magnetic field. It will also be understood, of course, that a wide variety of instruments can be used to detect mass changes, position changes, movements, weight changes, force changes, magnetic susceptibility, induction, optical changes, and the like, all of which result from the interaction between a magnetic field and the magnetically responsive reagent.

The present invention solves the problems of conventional heterogeneous and agglutination assays by allowing the magnetically responsive reagent to associate with like reagents or with other magnetically non-responsive particles, then applying a magnetic field, and measuring the consequences of the magnetic force exerted upon the magnetically responsive reagent to provide qualitative or quantitative assay results. Small levels of force can be readily determined using detectors which include, but are not limited to, electronic balances; optical sensors; piezoelectric pressure sensing devices such as, for example, micromechanical silicon devices or electronic chips; vibrating fiber devices; coils that produce a field which is disrupted by the presence of a magnetically responsive reagent, such as, for example induction coils and the like; and cantilever beam devices including, but not limited to those used to sense force changes in an atomic force microscope; and the like. These detectors enable performance of very sensitive assays and obviate the need for amplification of the label, as is required in many conventional assays.

Conventional heterogeneous binding assays require vigorous washing of the solid phase to separate bound labeled reagent and unbound labeled reagent and to suppress the nonspecific binding of materials to the solid phase. Such wash steps complicate the assay protocol and restrict the assay to the use of specific binding pair members having high affinity, i.e., a binding strength that will withstand such physical manipulation. In conventional particle agglutination assays, binding members of low affinity can be used because several binding sites on each member can cooperate to give high avidities, and the absence of wash steps allows weak associations to be maintained while simplifying the assay format. Signal amplification results because the interaction of a few binding sites can cause the aggregation of complexes several orders of magnitude greater in size and mass than the original binding members, and thereby provide a macroscopic change, which can be interpreted visually. However, particle agglutination assays are often difficult to interpret, do not yield quantitative results, and are not readily amenable to automation.

According to the present invention, the intensity of the magnetic field can be precisely manipulated, for example, by means of an electromagnet, a movable permanent magnet, or by encoding magnetic fields of specific strengths or gradients or both onto magnetically responsive materials. A field intensity or gradient or both that is optimal for a particular assay and particular binding reagents can be chosen, thereby allowing for correction of lot-to-lot variations in other reagents, or in the selective binding of certain subsets of reagents or complexes so as to obtain more precise assay results. It is to be understood that the aforementioned advantages permit the assays to be readily adapted to control by computer.

While various devices and assay protocols are contemplated by the present invention, the following protocols represent examples, and are not limited to, a sandwich assay format and an indirect/competitive assay format using magnetically assisted detection of a magnetically responsive reagent. In this regard, the following protocols, and protocols contemplated by the present invention, can be performed in any order of steps or, alternatively, in a simultaneous manner.

Protocol A

1) A first specific binding member having a binding site capable of binding to a first binding site on the analyte of interest is attached to a magnetically responsive material to form a magnetically responsive reagent;
2) a second specific binding member having a binding site capable of binding to a second binding site on the analyte of interest is attached to a mobile solid phase to form a mobile solid phase reagent;
3) a test sample is contacted with the mobile solid phase reagent to form a first reaction mixture, whereby the analyte of interest becomes bound to the mobile solid phase reagent;
4) the first reaction mixture is contacted with the magnetically responsive reagent to form a second reaction mixture, whereby the magnetically responsive reagent forms a complex with the mobile solid phase reagent and the analyte by binding to the bound analyte (the proportion of magnetically responsive reagent that forms a complex with the mobile solid phase reagent and the analyte is directly related to the amount of analyte in the test sample);
5) the second reaction mixture is subjected to a detector;
6) the second reaction mixture is exposed to a magnetic field such that a magnetic force is exerted upon the complex of the magnetically responsive reagent, the mobile solid phase reagent, and the analyte, the influence of this force being manifested by the movement or capture of the magnetically responsive reagent-analyte-mobile solid phase reagent complexes at a different rate from that of the uncomplexed magnetically responsive reagent or from that of the uncomplexed mobile solid phase reagent, and the degree of the manifestation is determined by the detector; and
7) the measurable degree of the manifestation provides a measure of the quantity of the magnetically responsive reagent that has been incorporated into complexes.

Protocol B

1) A first specific binding member having a binding site (first binding site) capable of binding to a binding site on the analyte of interest (second binding site) is attached to a magnetically responsive material to form a magnetically responsive reagent;
2) a second specific binding member having a binding site (third binding site) capable of binding to the first binding site is attached to a mobile solid phase material to form a mobile solid phase reagent;
3) a test sample is contacted with the magnetically responsive reagent to form a first reaction mixture, whereby the analyte becomes bound to the magnetically responsive reagent;
4) the first reaction mixture is contacted with the mobile solid phase reagent to form a second reaction mixture, whereby the magnetically responsive reagent becomes bound to the mobile solid phase reagent by binding to the second specific binding member (the proportion of magnetically responsive reagent that becomes bound to the mobile solid phase reagent is inversely related to the amount of analyte in the test sample);
5) the second reaction mixture is subjected to a detector;
6) the second reaction mixture is exposed to a magnetic field such that a magnetic force is exerted upon the complex of the magnetically responsive reagent bound to the solid phase, the influence of this force being manifested by the movement or capture of the complexes containing the magnetically responsive reagent and the mobile solid phase reagent at a different rate from that of the uncomplexed magnetically responsive reagent or from that of the uncomplexed mobile solid phase reagent, and the degree of the manifestation is determined by the detector; and
7) the degree of the manifestation provides a measure of the quantity of the magnetically responsive reagent that has been incorporated into complexes.

FIG. 1 illustrates the binding reactions of Protocol B. FIG. 1 illustrates schematically the binding of a magnetically responsive reagent 2 (e. g., ferrofluid) to a mobile solid phase reagent 4 (e. g., polypyrrole latex) to produce a complex 6 with altered magnetic properties. A particle of ferrofluid that is not in a complex would not respond as rapidly to an applied magnetic field as would a complex containing a multiplicity of particles of ferrofluid.

In either Protocol A or Protocol B, steps 5 and 6 can be reversed.

The following embodiments exemplify how the method of the present invention can be used to perform immunoassays.

EMBODIMENT 1

Figure 2:
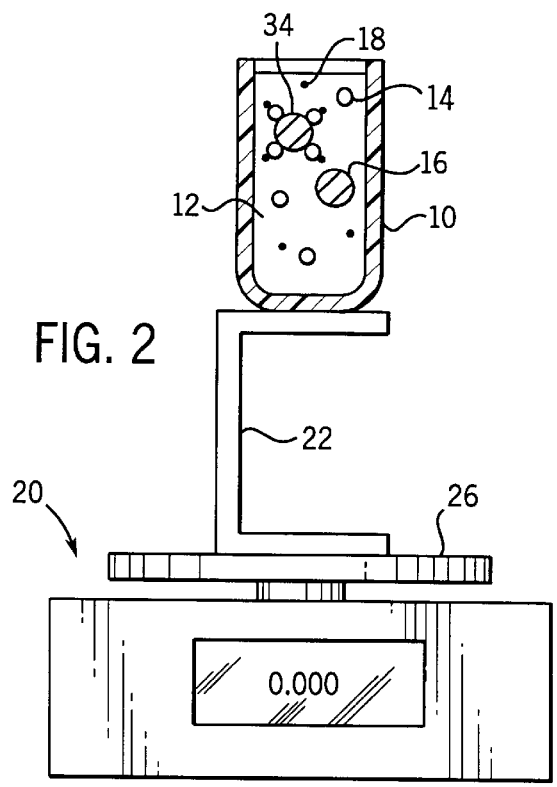
FIG. 2 is a schematic view of an apparatus utilizing a balance for the magnetically assisted detection of complexes containing a magnetically responsive reagent.
Figure 3:
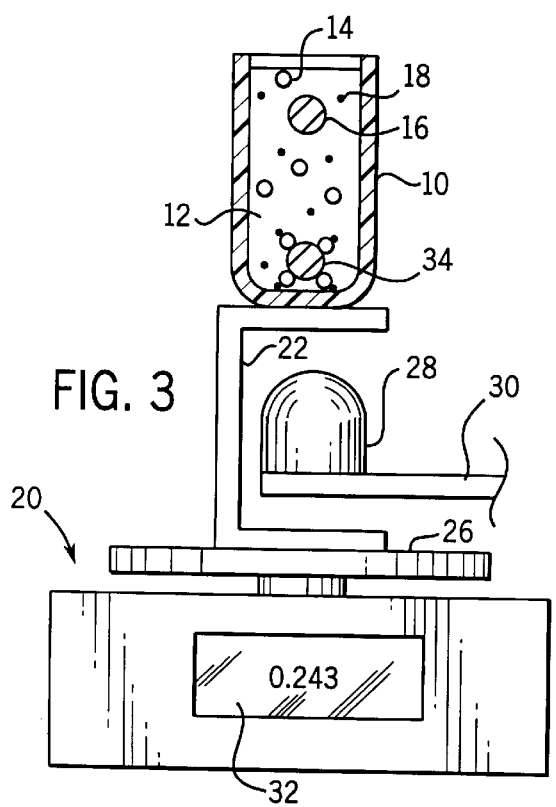
FIG. 3 is a schematic view of the apparatus of FIG. 2 in operation for the magnetically assisted detection of complexes containing a magnetically responsive reagent.

FIGS. 2 and 3 illustrate schematically the magnetically assisted measurement of the binding of a magnetically responsive reagent to a mobile solid phase reagent (by means of the analyte), and substantially follows Protocol A after the reaction mixture has been subjected to a detector (step 6 of Protocol A).

As shown in FIG. 2, reaction vessel 10 contains a reaction mixture 12, which comprises the analyte 14, a suspension of particles of the mobile solid phase reagent 16, and particles of the magnetically responsive reagent 18. The reaction mixture 12 is subjected to the detector 20 by setting the reaction vessel 10 upon or affixing the reaction vessel 10 to a support 22. The support 22 rests upon the detector 20. The detector 20 can be a typical top-loaded microbalance, having a pan 26, which will receive the support 22. Once the pan 26 receives the support 22, and the support 22 receives the reaction vessel 10, the detector 20 can be tared or set to equilibrium (zeroed).

As shown in FIG. 3, a magnet 28 is brought into proximity with the bottom of the reaction vessel 10, whereby the magnetic field exerts a force upon the magnetically responsive reagent in the reaction mixture 12. Generally, the magnet 28 is affixed to an arm 30, which allows precise adjustments of the movement of the magnet 28 toward and away from the reaction vessel 10. The magnetic field may be provided by means of a permanent magnetic or an electromagnet and may be applied intermittently or continuously. An electromagnetic may be used so that the magnetic field can be changed by being turned off and on rather than by moving the magnet 28 or the reaction vessel 10. An electromagnet can also be controlled by a computer, thereby providing for fine adjustments to the strength of the magnetic field. Furthermore, an electromagnet can be used to generate an alternating magnetic field, which can provide the further advantage of causing the mixing of the magnetically responsive reagent in the reaction mixture 12, if such mixing is desired.

The force exerted upon the magnetically responsive reagent in the reaction vessel 10 is manifested as an apparent change in the weight of the reaction vessel, which is registered on the display 32 of the detector 20. The magnetic force which is exerted upon a particle of the mobile solid phase reagent that has more than one particle of the magnetically responsive reagent bound to it (by means of the analyte) is greater than the force exerted upon a particle of the mobile solid phase reagent alone or upon a particle of the magnetically responsive reagent alone. Accordingly, complexes 34 comprising the mobile solid phase reagent, the analyte, and the magnetically responsive reagent move more rapidly in the field than do individual particles of the magnetically responsive reagent. The attractive force between the complexes 34 and the magnet 28 causes a force to be exerted upon the reaction vessel 10 and thus on the support 22 in the same direction as that due to gravity, which is registered on the display 32 of the detector 20 as a increase in apparent weight. As the complexes 34 of the mobile solid phase reagent, the analyte, and the magnetically responsive reagent migrate toward the bottom of the reaction vessel 10, and therefore move closer to the magnet 28, the force between the complexes 34 and the magnet 28 increases, further accelerating movement of the complexes 34. As the complexes 34 reach the bottom of the reaction vessel 10 and accumulate there, they exert their maximum force upon the reaction vessel 10 and its support 22 because of their proximity to the magnet. This phenomenon further increases the apparent weight of the reaction vessel 10 as indicated by the display reading. The rate at which the complexes 34 arrive at the bottom of the reaction vessel 10, and hence the rate of apparent weight change registered by the detector 20, is a measure of the degree of binding between the mobile solid phase reagent, the analyte, and the magnetically responsive reagent, and hence of the amount of analyte present in the reaction mixture. This rate can be recorded as a change of apparent weight as a function of time on a conventional recording device. The change of apparent weight is a measure of the amount of analyte in the test mixture.

EMBODIMENT 2

Figure 4:
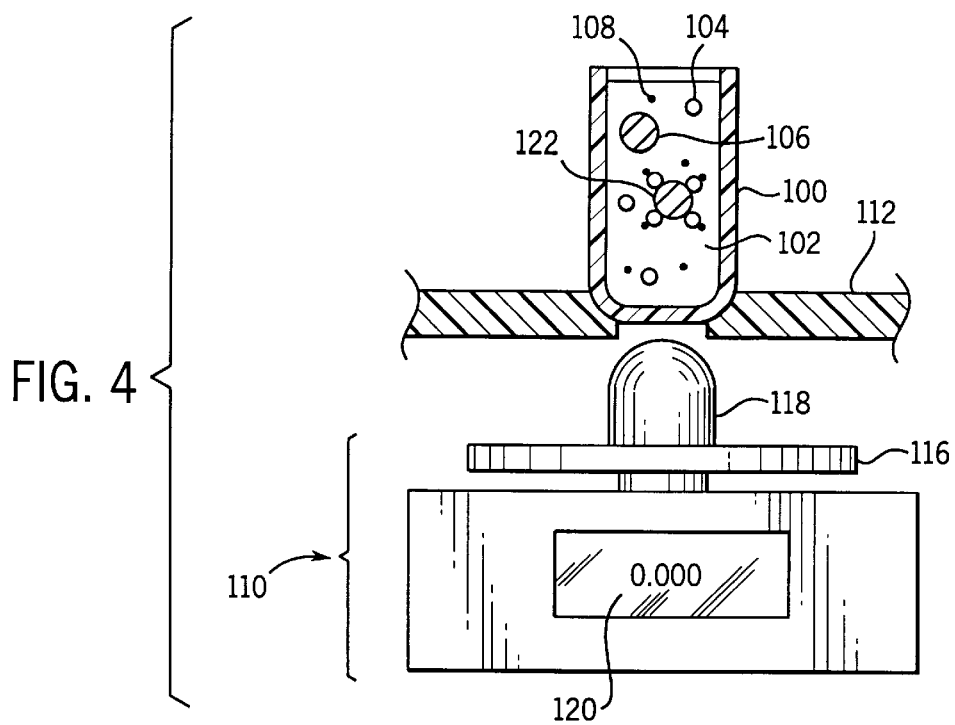
FIG. 4 is a schematic view of an apparatus utilizing a balance for the magnetically assisted detection of complexes containing a magnetically responsive reagent.
Figure 5:
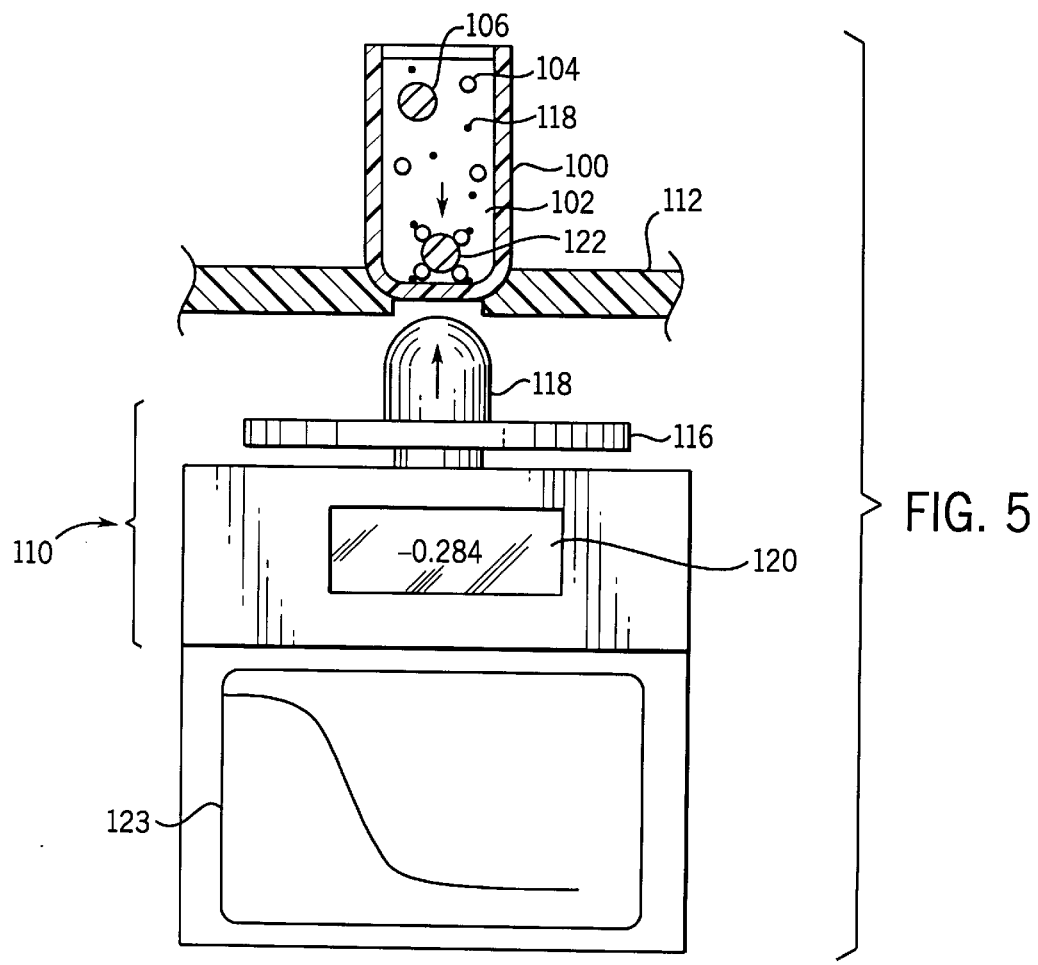
FIG. 5 is a schematic view of the apparatus of FIG. 4 in operation for the magnetically assisted detection of complexes containing a magnetically responsive reagent.

FIGS. 4 and 5 are schematic views of an alternate means for the measurement of the binding of a magnetically responsive reagent to a mobile solid phase reagent (by means of the analyte), and substantially follows Protocol A after the reaction mixture has been placed upon a detector (step 6 of Protocol A).

As shown in FIG. 4, a reaction vessel 100 contains a reaction mixture 102, which comprises the analyte 104, a suspension of particles of a mobile solid phase reagent 106, and particles of a magnetically responsive reagent 108. In FIG. 4, the reaction mixture is subjected to a detector 110 by setting the reaction vessel 100 upon or affixing the reaction vessel 100 to a support 112. The support 112 positions the reaction vessel 100 above the detector 110. A typical top-loaded microbalance with a weight-sensitive pan 116 can be used as the detector 110. A magnet 118 is positioned on the pan 116 below the position of the reaction vessel 100. Before the reaction vessel 100 is placed in the support 112, or before or just after the reaction mixture is placed in the reaction vessel 100, the detector 110 can be tared or set to equilibrium (zeroed).

FIG. 4 shows the procedure just after the reaction vessel 100 has been placed on the support 112. The magnetic field produced by the magnet 118 exerts a force upon the magnetically responsive reagent in the reaction mixture 102 in the direction of the magnet, and a corresponding force is exerted upon the magnet in the direction of the magnetically responsive reagent. The force exerted upon the magnet tends to counteract the force exerted upon it due to gravity, resulting in a change in the response of the detector 110. This initial detector response is due to the force between the magnet and the magnetically responsive reagent in their initial positions. If the balance is zeroed at this point, this initial response will become part of the tare weight of the balance and the detector 110 will display a zero reading. The response of the detector 110 can be observed on display 120.

The magnetic field produced by the magnet 118 exerts a force upon the magnetically responsive reagent in the reaction mixture 102. The magnetic force that is exerted upon a particle of the mobile solid phase reagent that has more than one particle of the magnetically responsive reagent bound to it (by means of the analyte) is greater than the force exerted upon a particle of the mobile solid phase reagent alone or upon a particle of the magnetically responsive reagent alone. Accordingly, complexes 122 of the mobile solid phase reagent, the analyte, and the magnetically responsive reagent move more rapidly in the magnetic field than do the individual particles of the magnetically responsive reagent. As the complexes 122 of the mobile solid phase reagent, the analyte, and the magnetically responsive reagent migrate toward the bottom of the reaction vessel 100, and therefore move closer to the magnet 118, the force between the complexes 122 and the magnet 118 increases, further accelerating the movement of the complexes. As shown in FIG. 5, as the complexes 122 reach the bottom of the reaction vessel 100 and accumulate there, they exert their maximum force upon the magnet 118, further decreasing the apparent weight of the magnet 118, as indicated by a change in the detector reading. The rate at which the complexes 122 arrive at the bottom of the reaction vessel 100, and hence the rate of apparent weight change registered by the detector 110, is a measure of the degree of binding between the mobile solid phase reagent, the analyte, and the magnetically responsive reagent, and hence of the amount of analyte present in the reaction mixture. This rate can be recorded as a change of apparent weight as a function of time on a recording device. Either the final change in detector response after all the complexes have migrated to the bottom of the reaction vessel 100 or the rate of change of the detector response during migration of the complexes can be used to measure the amount of analyte present in the reaction mixture an thus in the original test mixture. In FIG. 5, the arrows within the figure represent the force between the complexes and the magnet.

EMBODIMENT 3

Figure 6:
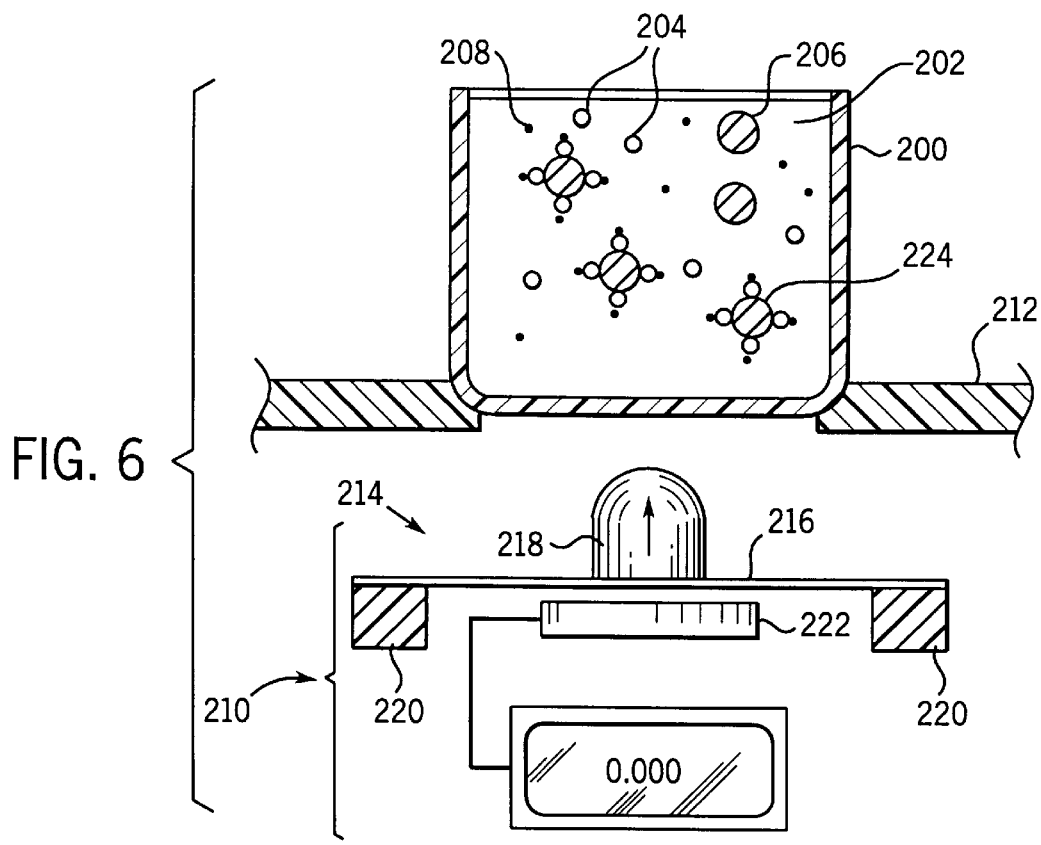
FIG. 6 is a schematic view of an apparatus utilizing a Hall effect transducer for the magnetically assisted detection of complexes containing a magnetically responsive reagent.
Figure 7:
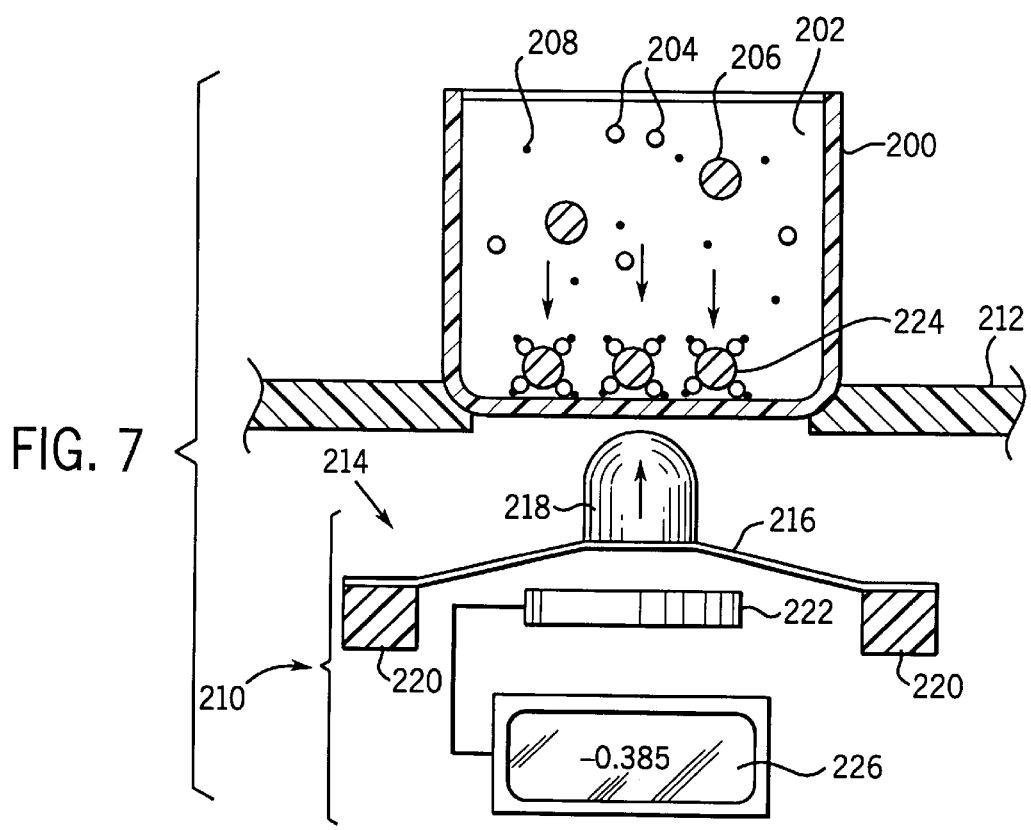
FIG. 7 is a schematic view of the apparatus of FIG. 6 in operation for the magnetically assisted detection of complexes containing a magnetically responsive reagent.

FIG. 6 and FIG. 7 are schematic views of an alternate means for the measurement of the binding of a magnetically responsive reagent to a mobile solid phase reagent (by means of the analyte), and substantially follows Protocol A after the reaction mixture has been placed upon a detector (step 6 of Protocol A).

As shown in FIG. 6, a reaction vessel 200 contains a reaction mixture 202, which comprises the analyte 204, a suspension of particles of a mobile solid phase reagent 206, and particles of a magnetically responsive reagent 208. The reaction mixture is subjected to a detector 210 by setting the reaction vessel 200 upon or affixing the reaction vessel 200 to a support 212. The support 212 positions the reaction vessel 200 above a sensor 214, which comprises a diaphragm of flexible material 216, which has a magnet 218 attached thereon. The diaphragm of flexible material 216 is supported on a foundation 220. The detector 210 comprises a Hall Effect Transducer 222, which is positioned below the diaphragm of flexible material 216. Detection is accomplished by monitoring the output of an electronic circuit connected to the Hall Effect Transducer 222. Changes in force upon the magnet 218 result in changes in its position relative to the Hall Effect Transducer 222, due to flexing of the diaphragm 216. This in turn results in a change in the magnetic field sensed by the Hall Effect Transducer 222, which is manifested by a change in the output of the electronic circuit. FIG. 6 shows the procedure just after the reaction vessel 200 has been placed on the support 212 and the detector zeroed.

The magnet 218 attached to the diaphragm 216 is positioned in proximity to the reaction vessel 200, whereby the magnetic field exerts a force upon the magnetically responsive reagent therein. As a result, complexes 224 of the mobile solid phase reagent, the analyte, and the magnetically responsive reagent move more rapidly in the magnetic field than do the individual particles of the magnetically responsive reagent. As the complexes 224 of the mobile solid phase reagent, the analyte, and the magnetically responsive reagent migrate toward the bottom of the reaction vessel 200, and therefore move closer to the magnet 218, the force between the complexes 224 and the magnet 218 increases, further accelerating the movement of the complexes 224. As is shown in FIG. 7, as the complexes 224 reach the bottom of the reaction vessel 200 and accumulate there, they exert their maximum attractive force upon the magnet 218 . This force is in turn exerted upon the diaphragm 216, causing it to flex and displace the magnet 218 away from the transducer 222. The degree of displacement from the original position of the magnet 218 is dependent upon the amount of the magnetically responsive reagent bound to the mobile solid phase reagent (by means of the analyte) and will be manifested as alteration in the signal produced by the electronic circuit. The rate at which the complexes 224 arrive at the bottom of the vessel 200, and hence the rate of signal change registered by the transducer circuit, is a measure of the degree of binding between the mobile solid phase reagent, the analyte, and the magnetically responsive reagent, and hence of the amount of analyte present in the reaction mixture. This rate can be recorded as a change of apparent weight as a function of time on a recording device. The rate of signal change can be viewed on a display 226. Either the final change in detector response after all the complexes have migrated to the bottom of the reaction vessel 200 or the rate of change of the detector response during migration of the complexes can be used to measure the amount of analyte present in the reaction mixture and thus in the original test mixture. The device of this embodiment can be made to function in any spatial orientation.

Other proximity measuring devices besides the Hall effect transducer 222 can be used. Representatives example of such devices include optical devices where a beam of light is reflected from the bottom of the diaphragm 216 onto a detector, a displacement of the diaphragm causing an alteration in the intensity of the light striking the detector. Optical devices measuring the change in interference patterns of light reflected from the diaphragm as a function of position distance or distortion can also be used. Non-optical methods of determining changes in diaphragm position or shape can also be used, such as the capacitance sensors commonly used as proximity detectors. In place of the diaphragm, other flexible elements, such as, strips, springs, cantilever arms, and the like, can be used. FIG. 7, the arrows within the figure represent the force between the complexes and the magnet.

EMBODIMENT 4

Figure 8:
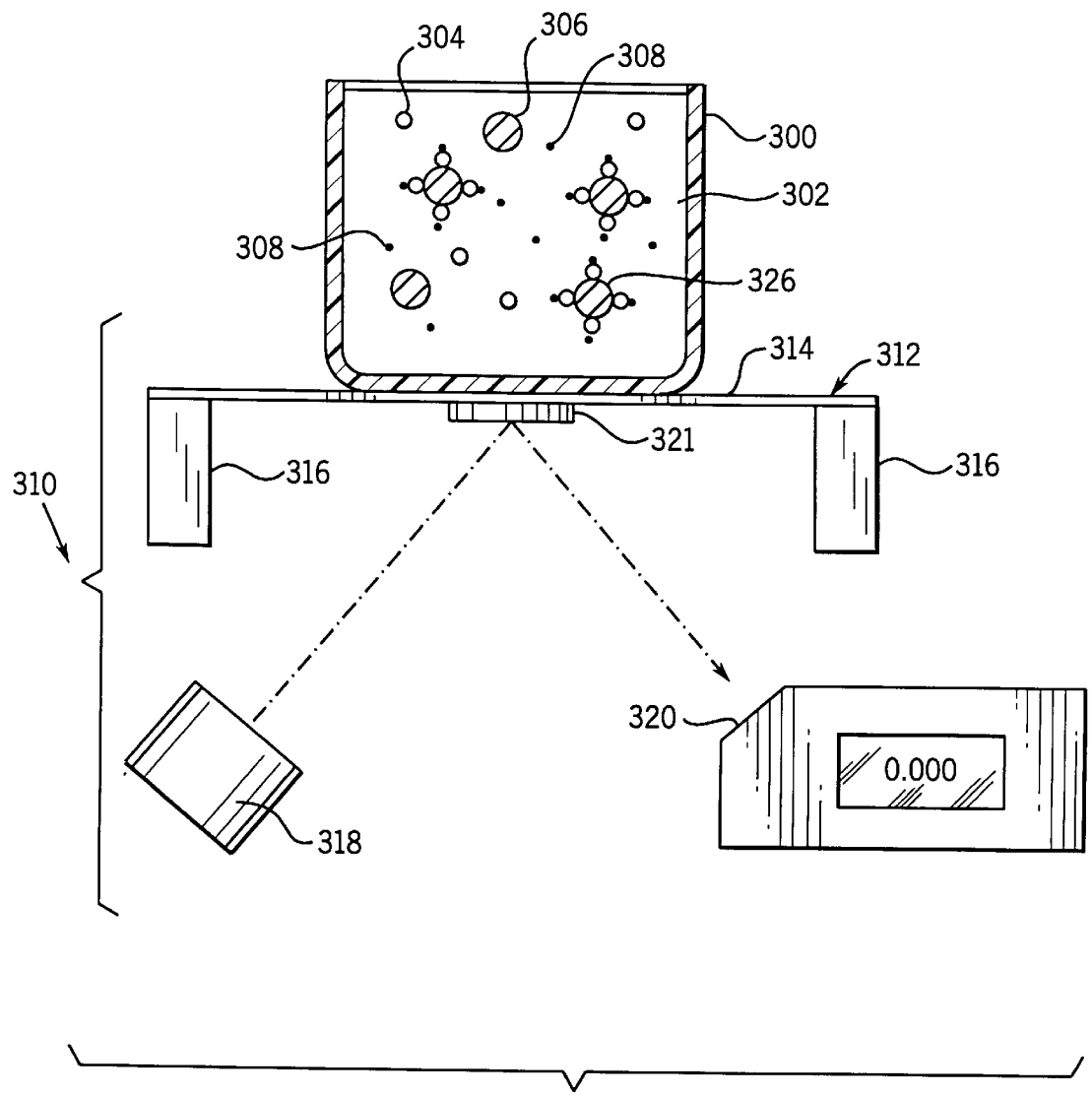
FIG. 8 is a schematic view of an apparatus utilizing an optical sensor for the magnetically assisted detection of complexes containing a magnetically responsive reagent.
Figure 9:
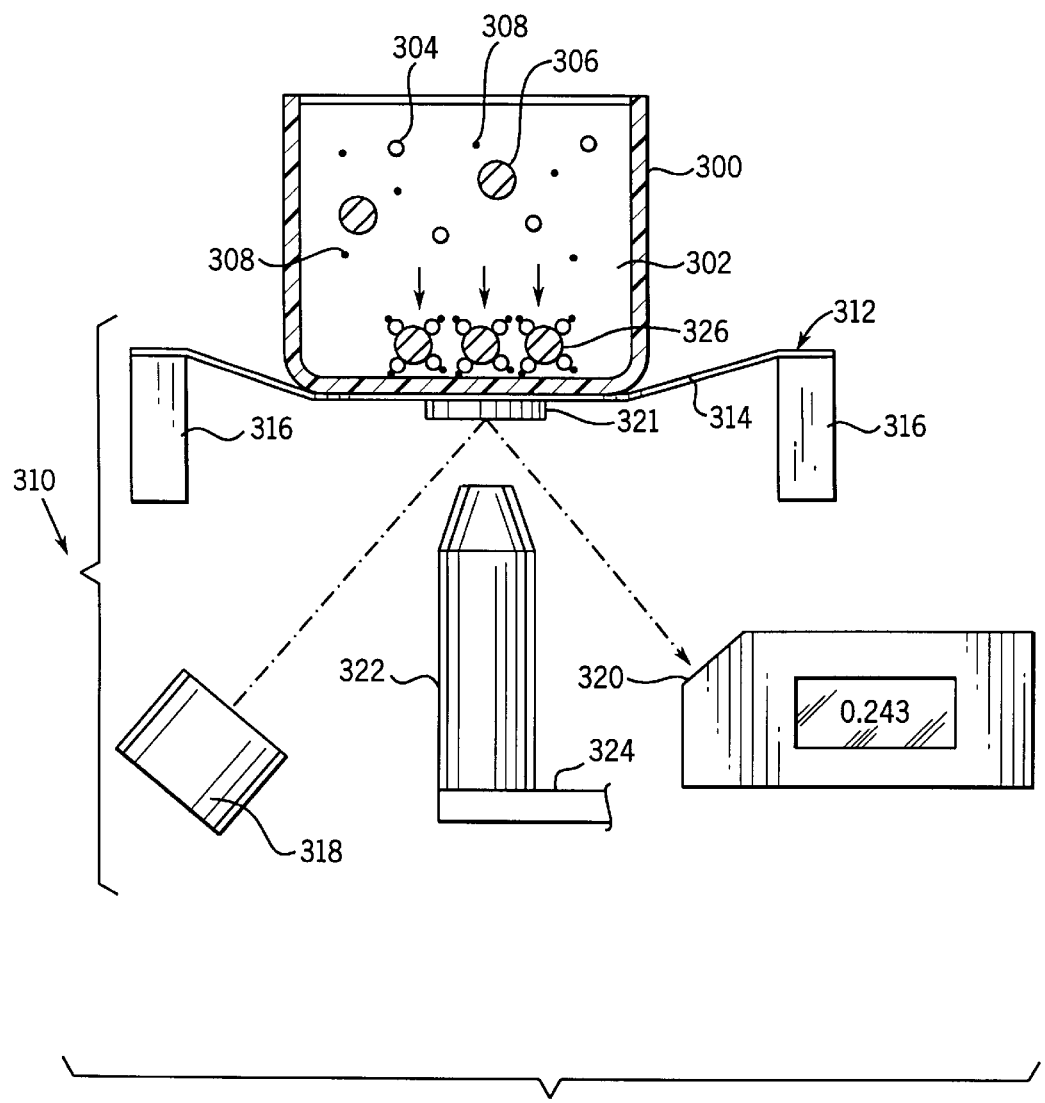
FIG. 9 is a schematic view of the apparatus of FIG. 8 in operation for the magnetically assisted detection of complexes containing a magnetically responsive reagent.

FIG. 8 and FIG. 9 are schematic views of an alternate means for the measurement of the binding of a magnetically responsive reagent to a mobile solid phase reagent (by means of the analyte), and substantially follows Protocol A after the reaction mixture has been placed on the detector (step 6 of Protocol A).

As shown in FIG. 8, a reaction vessel 300 contains a reaction mixture 302, which comprises the analyte 304, a suspension of particles of a mobile solid phase reagent 306, and particles of a magnetically responsive reagent 308. In FIG. 8, the reaction mixture 302 is subjected to a detector 310 by setting the reaction vessel 300 upon or affixing the reaction vessel 300 to a sensor 312. The sensor 312 comprises a diaphragm of flexible material 314. The diaphragm of flexible material 314 is supported on a foundation 316. Detection is accomplished by means of a light source 318 and an optical sensor 320. Light from the light source 318 is reflected from a reflective site 321 on the diaphragm 314 onto the optical sensor 320. Any deviation in the position of the diaphragm 314 results in a shift of position or deflection of the reflected light striking the optical sensor 320, thereby causing a change in the output of the optical sensor 320. It is to be understood that the diaphragm 314 itself can serve as a means for sensing position, light being reflected directly off the lower surface of the diaphragm 314.

As shown in FIG. 9, a magnet 322 is positioned in proximity to the diaphragm 314, whereby the magnetic field exerts a force upon the magnetically responsive reagent in the reaction mixture. As a result, complexes 326 of the mobile solid phase reagent, the analyte, and the magnetically responsive reagent move more rapidly in the magnetic field than do the individual particles of the magnetically responsive reagent. As the complexes 326 of the mobile solid phase reagent, the analyte, and the magnetically responsive reagent migrate toward the bottom of the reaction vessel 300, and therefore move closer to the magnet 322, the force between the complexes 326 and the magnet 322 increases, further accelerating the movement of the complexes 326. As the complexes 326 reach the bottom of the reaction vessel 300 and accumulate there, they exert their maximum attractive force upon the magnet 322. This force is in turn exerted upon the diaphragm 314, thereby causing it to flex. The degree of displacement or distortion from the original position of the diaphragm 314 is largely dependent upon the degree of binding between the magnetically responsive reagent, the analyte, and the mobile solid phase reagent, and hence of the amount of analyte present in the reaction mixture. The degree of binding can be measured by the detector 310. It is to be understood that the reaction vessel 300 can be permanently affixed to the flexible diaphragm 314 and reused by removing and replacing the reaction mixture 302. It is also to be understood that the reaction vessel 300 or the flexible diaphragm 314 can be disposable. It is also to be understood that the flexible support need not be in the form of a diaphragm. Any flexible or displaceable support can be used, such as, for example, cantilever arms, elastic suspenders, springs, or buoyant devices.

It is to be understood that the flexible material itself can serve as the reaction vessel, the reaction mixture being placed directly upon it. It is to be further understood that the flexible material can be of such a shape as to form sites at which the reaction mixture could be contained. It is also to be understood that the flexible material can be a web that can be moved across the sensor. In FIG. 9, the arrows within the figure represent the force between the complexes and the magnet.

EMBODIMENT 5

Figure 10:
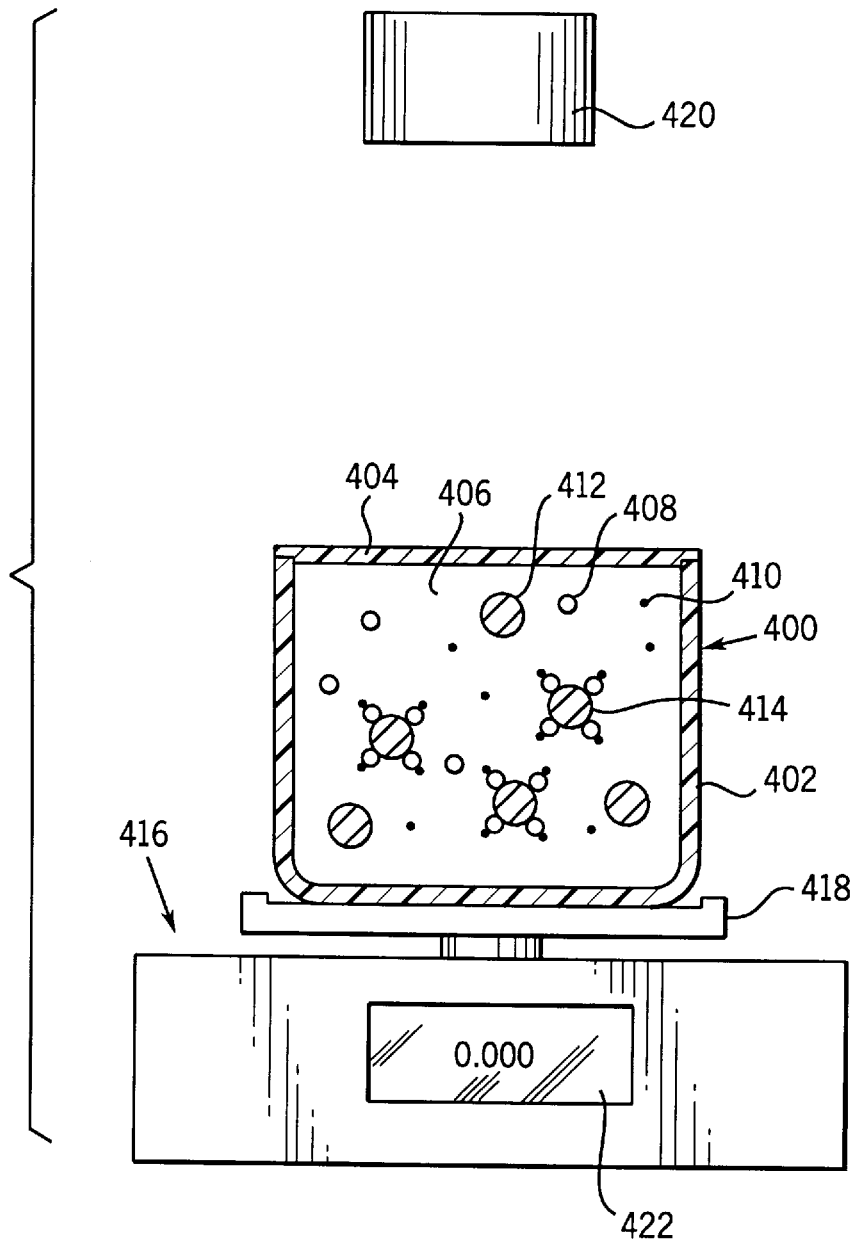
FIG. 10 is a schematic view of an apparatus utilizing a balance for the magnetically assisted detection of complexes containing a magnetically responsive reagent.
Figure 11:
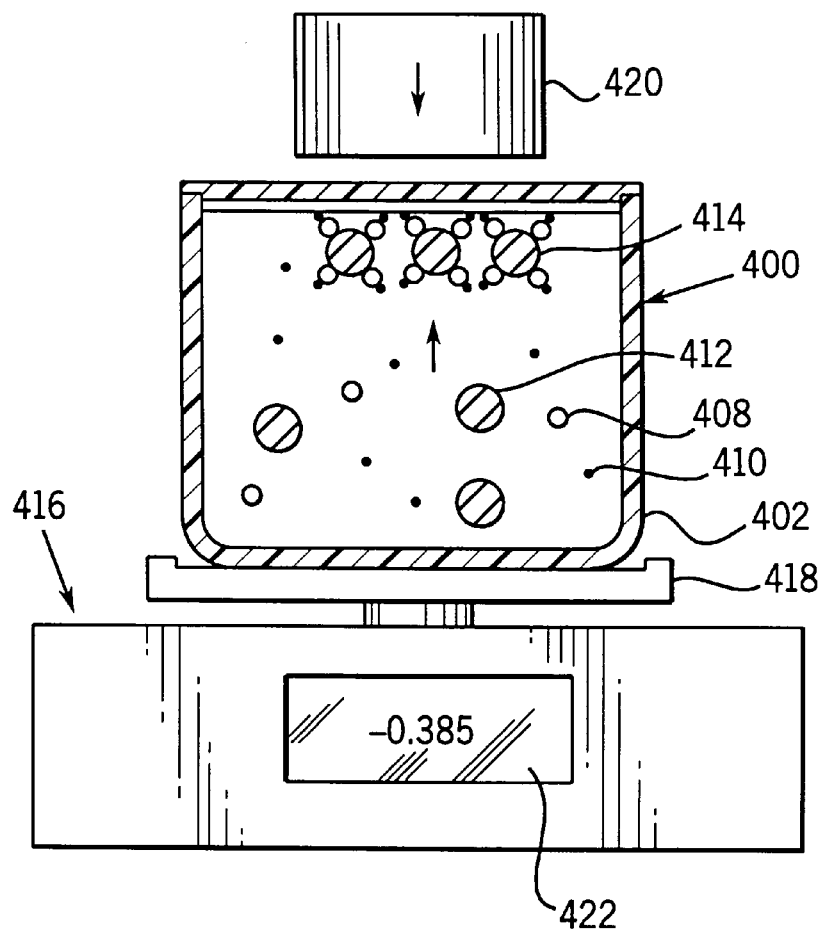
FIG. 11 is a schematic view of the device of FIG. 10 in operation for the magnetically assisted detection of complexes containing a magnetically responsive reagent.

FIG. 10 and FIG. 11 are schematic views of another means for measurement of the binding of a magnetically responsive reagent to a mobile solid phase reagent (by means of the analyte), and substantially follows Protocol A after the reaction mixture has been placed on a detector (step 6 of Protocol A).

As shown in FIG. 10, a reaction vessel 400 comprises a well 402, having a lid 404. The well 402 contains a reaction mixture 406. If analyte 408 is present, a portion of the magnetically responsive reagent 410 binds to the mobile solid phase reagent 412 to form complexes 414 (by means of the analyte). The well 402 is set upon or affixed to a force sensing device, such as a balance 416 having a pan 418, which receives the well 402. Once the balance 416 receives the well 402, the balance 416 can be zeroed.

As shown in FIG. 11, a magnet 420 is brought into proximity to the lid 404, whereby the magnetic field exerts a force upon the magnetically responsive reagent within the well 402. Under the influence of this force, the complexes 414 of the mobile solid phase reagent, the analyte, and the magnetically responsive reagent migrate to the underside of the lid 404 where the magnetic attractive force is more intense due to the closer proximity to the magnet 420. The unbound magnetically responsive reagent 410 moves more slowly under this level of magnetic field intensity than do the complexes 414 and takes longer to reach the underside of the lid 404. As the complexes 414 of the mobile solid phase reagent, the analyte, and the magnetically responsive reagent accumulate on the underside of the lid 404, they produce an upward force against it, counteracting the force of gravity and causing a decrease in the apparent weight of the well 402, which is registered on the display 422 of the balance 416. The rate at which the complexes 414 arrive at the underside of the lid 404, and hence the rate of apparent weight change registered by the balance 416, is also a measure of the degree of binding between the mobile solid phase reagent, the analyte, and the magnetically responsive reagent, and hence is also a measure of the amount of analyte present in the reaction mixture. This rate can be recorded as a change of apparent weight as a function of time on a recording means. This method can also be applied using reaction vessels with open tops, the surface tension of the reaction mixture surface serving the same purpose as the lid. The apparent rate of change of the weight of the well 402 will be rapid at first but will diminish as all the complexes are captured. The total change in weight at this end point can be used to measure the quantity of analyte in the reaction mixture. In FIG. 11, the arrows within the figure represent the force between the complexes and the magnet. Alternatively, the magnet 420 could be attached to a balance such that changes in force exerted on the magnet by the complexes would be measured.

EMBODIMENT 6

Figure 12:
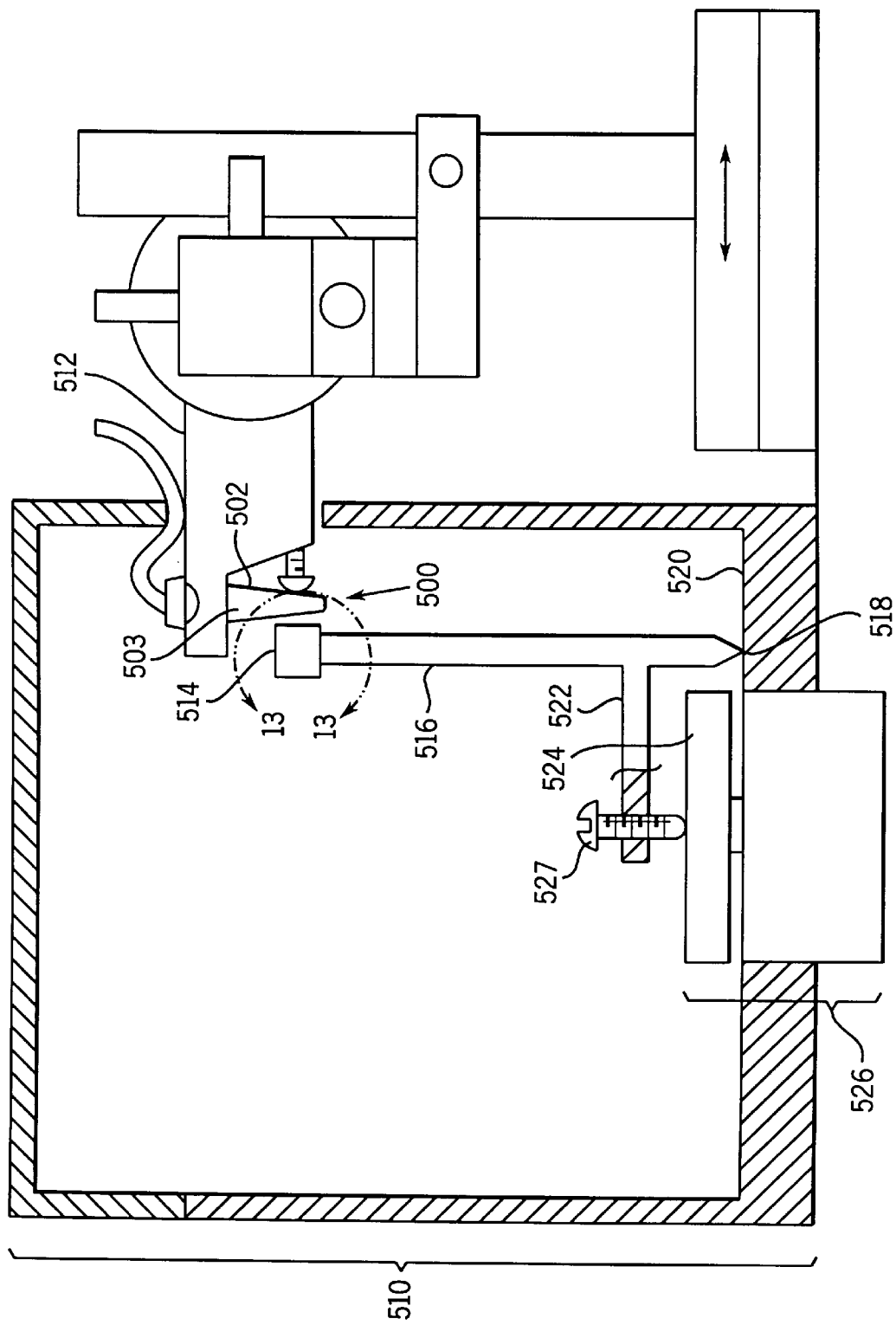
FIG. 12 is a schematic view of an apparatus utilizing a microbalance for the magnetically assisted detection of complexes containing a magnetically responsive reagent.
Figure 13:
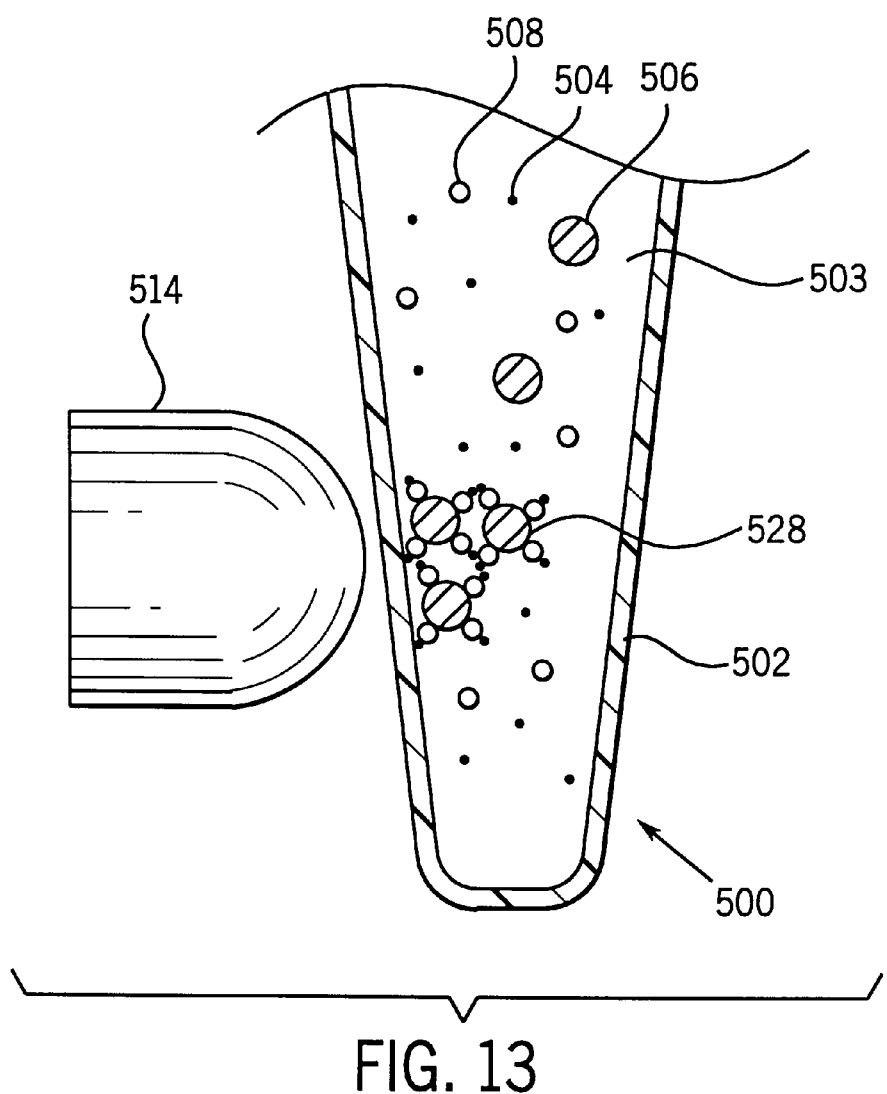
FIG. 13 is a schematic view of a portion of the apparatus of FIG. 12 in operation for the magnetically assisted detection of complexes containing a magnetically responsive reagent.

FIGS. 12 and 13 illustrate an alternate detector for the measurement of the binding of a magnetically responsive reagent to a mobile solid phase reagent (by means of the analyte), and substantially follows Protocol A after the reaction mixture has been placed on detector (step 6 of Protocol A).

As shown in FIG. 12 and in more detail in FIG. 13, a reaction vessel 500 comprises a well 502 that contains a reaction mixture 503 comprising particles of a magnetically responsive reagent 504, a mobile solid phase reagent 506, and, if present, an analyte 508. At least a portion of the magnetically responsive reagent 504 are bound to particles of the mobile solid phase reagent 506 (by means of the analyte 508). The reaction mixture 503 is subjected to a detector 510 by setting the reaction vessel 500 into or affixing the reaction vessel 500 to a first support 512. The support 512 serves to position the reaction vessel 500 near a magnet 514, which is attached to a second support 516. The second support 516 has a knife edge 518 that rests upon a solid surface 520 and a side arm 522 that overlies the pan 524 of a balance 526. The second support 516 is positioned in such a way that is free to pivot on its knife edge 518 and is only held in its vertical position by the bearing of the side arm 522 on the pan 524 of the balance 526 through an adjustment screw 527. Once the supports 512, 516 are positioned, the balance 526 can be tared or set to equilibrium (zeroed).

The well 502 is then set into or affixed to the first support 512, thereby bringing it into proximity of the magnet 514, whereby the magnetic field exerts a force upon the magnetically responsive reagent within the well 502. Under the influence of this force, complexes 528 of the mobile solid phase reagent, the analyte, and the magnetically responsive reagent migrate to the side of the well 502 where the magnetic attraction is more intense, due to the closer proximity of the magnet 514. The unbound magnetically responsive reagent 504 moves more slowly under this level of magnetic field intensity and takes longer to reach the side of the well 502.

The complexes 528 of the mobile solid phase reagent, the analyte, and the magnetically responsive reagent produce a force upon the magnet 514 directed laterally toward the well 502. This force counteracts the force of the side arm 522 of the second support 516 bearing on the pan 524 of the balance 526, resulting in a decrease in the apparent weight of the side arm 522 reported by the balance 526. The force exerted upon the magnet is not sufficient to substantially move the second support 516, but sufficient only to decrease its bearing weight on the balance pan 524. Balance devices that maintain the pan position regardless of the weight bearing upon it are also available. It is to be understood that the concept of this embodiment is not restricted to the use of balances. Any force measuring device can be used, including those described previously, i.e., those using flexible supports and optical or other positioning sensors. The rate at which the complexes 528 arrive at the side of the well 502, and hence the rate of apparent weight change registered by the balance 526, is a measure of the degree of binding between the mobile solid phase reagent, the analyte, and the magnetically responsive reagent, and hence of the amount of analyte present in the reaction mixture. This rate can be recorded as a change of apparent weight as a function of time on a recording means.

EMBODIMENT 7

Figure 14A:
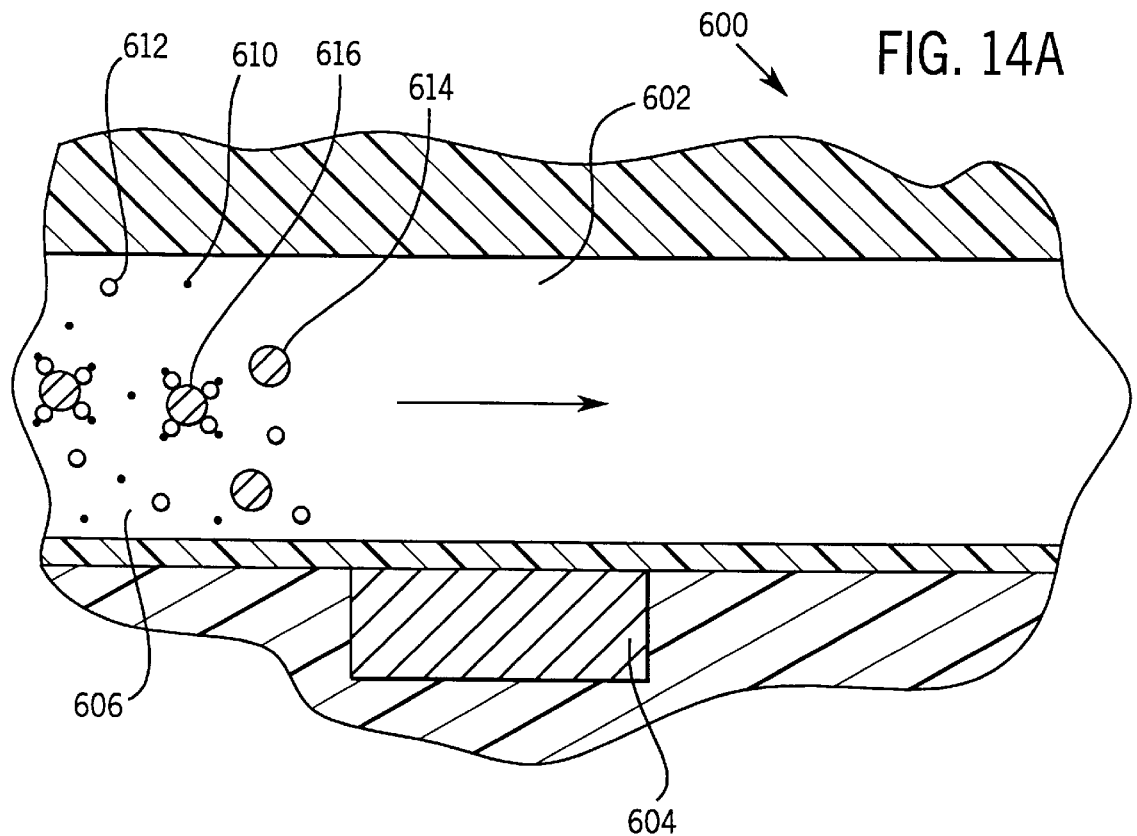
FIG. 14A is a schematic view of one type of self-performing immunoassay device in operation for the magnetically assisted detection of complexes containing a magnetically responsive reagent. The figure depicts the immunoassay before the complex is captured.
Figure 14B:
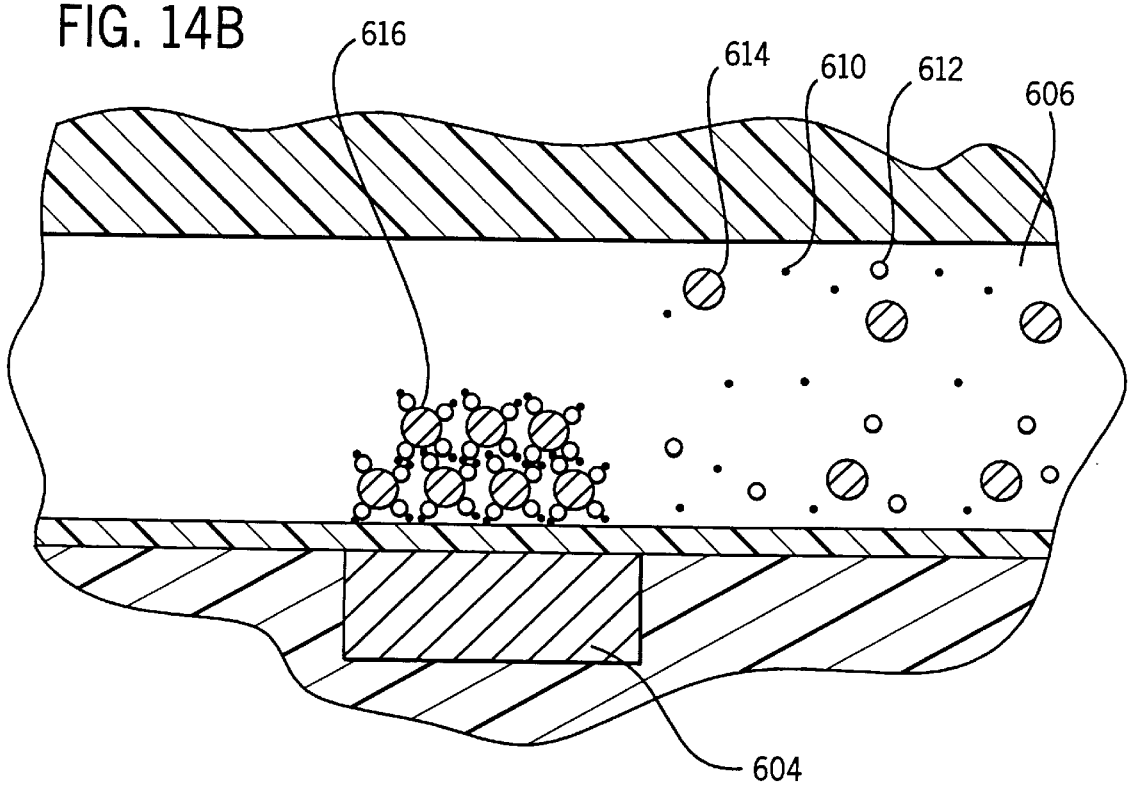
FIG. 14B is a schematic view of the self-performing immunoassay device of FIG. 14A in operation for the magnetically assisted detection of complexes containing a magnetically responsive reagent. The figure depicts the immunoassay after the complex is captured.

As a further embodiment of the present invention, FIGS. 14A and 14B illustrate a self-performing immunoassay device for performing analytical tests. The device 600 comprises a capillary channel 602 having one or more magnetic sites 604. The reaction mixture 606 is drawn down the channel 602 by capillary action. The reaction mixture contains a magnetically responsive reagent 610, the analyte 612, and a mobile solid phase reagent 614. As the reaction mixture 606 flows down the channel 602, it passes over the magnetic site or sites 604, at which position(s) complexes 616 of the mobile solid phase reagent 614, the analyte 612, and the magnetically responsive reagent 610 preferentially accumulate against the wall of the channel 602. In some applications, it may be advantageous to choose the intensity or gradient of the magnetic field at the magnetic site(s), or the size and composition of the magnetically responsive reagent, so that the magnetically responsive reagent will accumulate whether it is unbound or formed into a complex with the mobile solid phase reagent. The presence or extent of this accumulation of the mobile solid phase reagent can be measured in a variety of ways.

In a preferred embodiment of this invention, particles of the mobile solid phase reagent 614 or particles of the magnetically responsive reagent 610 are fabricated so that accumulation of the complexes 616 of the mobile solid phase reagent 614, the analyte 612, and the magnetically responsive reagent 610 at the magnetic site or sites 604, causes visible results to be formed. However, it is to be understood that the accumulation of the complexes 616 can be detected or measured by fluorescence emission, reflectivity, densitometry, enzyme activity, or any of the methods of the other embodiments described herein or by other means.

In a particularly preferred embodiment, the magnet site 604 can be a magnetic recording tape or a magnetic strip similar to that found on a conventional credit card. The magnetic site 604 can also serve as an interior surface of the capillary channel 602. The magnetic site(s) 604 can be single or multiple, of various shapes, and of differing field strengths or gradients, so that complexes of the mobile solid phase reagent, the analyte, and the magnetically responsive reagent having different ratios of mobile solid phase reagent and magnetically responsive reagent are captured at different site(s) 604 as an indication of concentration of analyte in the test sample.

The field intensities, gradients, sizes, and shapes of the magnetic site(s) as well as the size, shape, and composition of the magnetically responsive reagent can be chosen to optimize qualitative, e. g., positive/negative, results or more quantitative, e. g., semi-quantitative, results. For example, a series of identical magnetic capture sites could be encoded along the bottom of the capillary channel illustrated in FIGS. 14A and 14B. Each site could be encoded so as to have a limited capacity to bind the complexes comprising the magnetically responsive reagent and the mobile solid phase reagent. As the reaction mixture progresses downstream along the channel, the complexes would first encounter the most upstream of the magnetic capture sites of the series and be accumulated there. In a reaction mixture containing few complexes, only the most upstream of the magnetic capture sites would display accumulation of complexes. If, however there were sufficient complexes to saturate the most upstream of the magnetic capture sites, additional complexes would flow past that site to be accumulated at the next most upstream of the magnetic capture sites, and so on. The number of magnetic capture sites displaying accumulation of complexes would then serve as a measure of the extent of complex formation in the reaction mixture, and hence of the concentration of analyte in the test sample.

Alternatively, in certain assay formats, the concentration of the analyte in the reaction mixture can be manifested by the number of particles of magnetically responsive reagent bound to each particle of mobile solid phase reagent rather than by the extent of complex formation. In these cases, multiple magnetic capture sites, which differ in magnetic field strength or gradient or both, can be encoded on the bottom of the capillary channel. Each field strength/gradient combination would show a preference for attracting complexes with a particular ratio of magnetically responsive reagent to mobile solid phase reagent. For example, as the reaction mixture progressed downstream along the channel, the complexes could first encounter the magnetic capture site having the weakest field intensity. This site would only capture those complexes having a high ratio of magnetically responsive reagent to mobile solid phase reagent. Subsequent magnetic capture sites would progressively increase in field intensity, thereby being capable of capturing complexes having lower and lower ratios of magnetic responsive reagent to mobile solid phase reagent. In this case, which magnetic capture site(s) of the series display accumulation of complexes will be an indication of how extensive the accumulation of the magnetically responsive reagent has been, and consequently, how much analyte was present in the test sample. It is to be understood that the accumulation of the complexes can be detected or measured visually or by fluorescence emission, reflectivity, densitometry, enzyme activity, or any of the methods of the other embodiments described herein or by other means. This embodiment provides a small, portable, potentially disposable analytical device that requires no electrical power.

In another embodiment of the present invention, which employs a device as illustrated in FIGS. 14A and 14B, the floor of the capillary channel is fabricated from optically absorbing material. The mobile solid phase reagent displays optical properties (reflectance, color, fluorescence, chemiluminescence, or the like) that provide contrast to the optically absorbing capillary channel floor in proportion to the extent of accumulation of the mobile solid phase reagent. In this way, the optical properties of the magnetically responsive reagent can be masked, which is a property especially useful in formats where the magnetically responsive reagent is always captured at the magnetic capture site.

EMBODIMENT 8

Figure 15A:
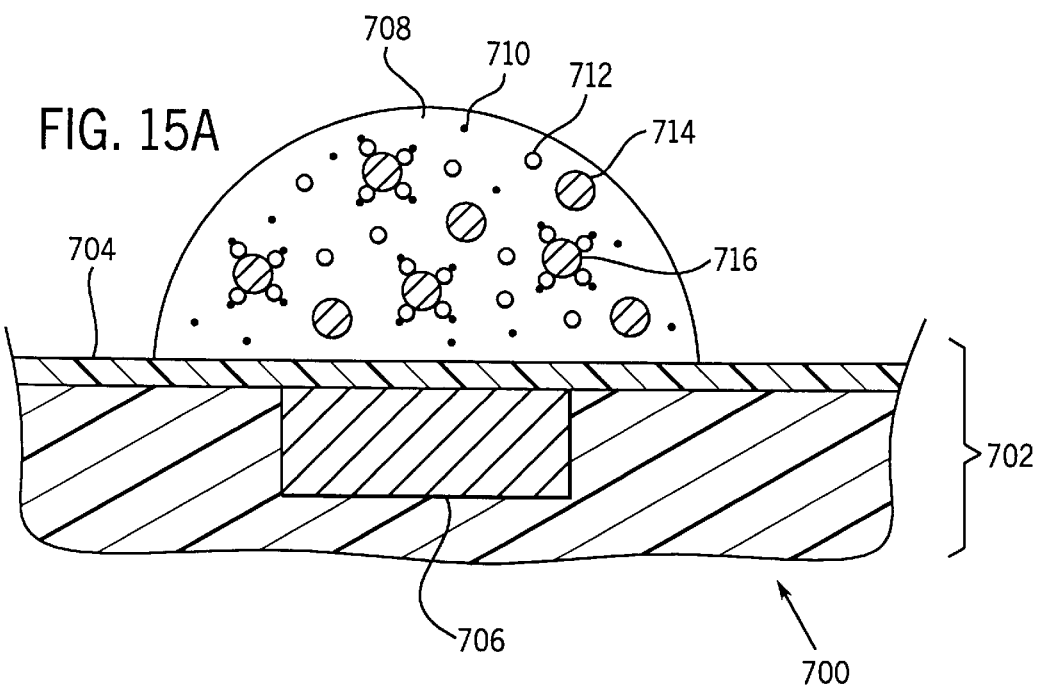
FIG. 15A is a schematic view of another type of self-performing immunoassay device for the magnetically assisted detection of complexes containing a magnetically responsive reagent. The figure depicts the immunoassay before the complex is captured.
Figure 15B:
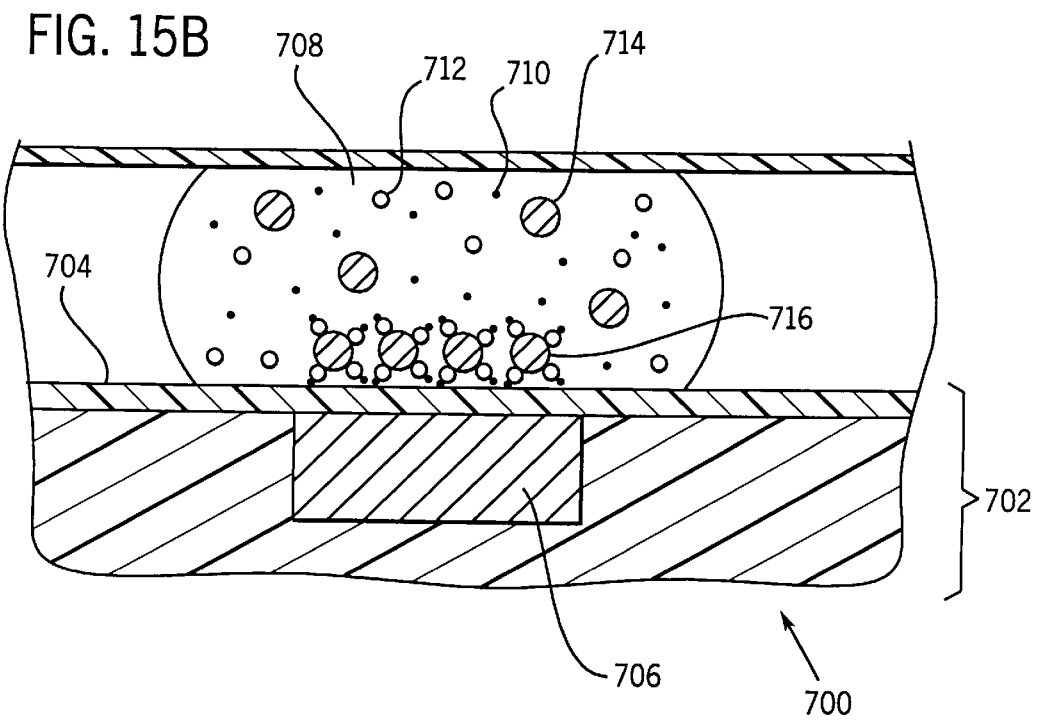
FIG. 15B is a schematic view of the self-performing immunoassay device of FIG. 15A in operation for the magnetically assisted detection of complexes containing a magnetically responsive reagent. The figure depicts the immunoassay after the complex is captured.

In another embodiment of the present invention, FIGS. 15A and 15B illustrate a self-performing immunoassay device for performing analytical tests. The device 700 comprises an element 702 having a flat surface 704 containing one or more magnetic sites 706. A reaction mixture 708 is brought in contact with the surface 704 or with a layer of material covering the surface 704. The reaction mixture 708 contains a magnetically responsive reagent 710, the analyte 712, and a mobile solid phase reagent 714. Complexes 716 of the mobile solid phase reagent 714, the analyte 712, and the magnetically responsive reagent 710 preferentially migrate to and accumulate at the magnetic sites 706. In some applications, it may be advantageous to choose the intensity or gradient of the magnetic field at the magnetic capture site(s), or the size and composition of the magnetically responsive reagent, so that the magnetically responsive reagent accumulates whether it is unbound or formed into a complex the mobile solid phase reagent. The presence or extent of this accumulation of the mobile solid phase reagent can be measured in a variety of ways.

In a preferred embodiment of this invention, particles of the mobile solid phase reagent 714 or particles of the magnetically responsive reagent 710 are fabricated so that when complexes 716 of the mobile solid phase reagent 714, the analyte 712, and the magnetically responsive reagent 710 accumulate at the magnetic site 706, a visible result is formed. The shape, color, density, extent, position, etc. serve as a measure of the presence or amount of analyte in the test mixture. The magnetic sites 706 can be single or multiple, of various shapes, and of differing field strengths or gradients, so that complexes of the mobile solid phase reagent, the analyte, and the magnetically responsive reagent having different ratios of mobile solid phase reagent and magnetically responsive reagent are captured at different sites 706 as an indication of concentration of analyte in the test sample. It is to be understood that the accumulation of the complexes can be detected or measured by fluorescence emission, reflectivity, densitometry, enzyme activity, or any of the methods of the other embodiments described herein or by other means.

In a particularly preferred embodiment, the magnetic site 706 can be a magnetic recording tape or a magnetic strip similar to that found on a conventional credit card. This embodiment provides a small, portable, potentially disposable analytical device that requires no electrical power.

EMBODIMENT 9

In another embodiment of this invention, the procedures described herein can be used to determine the properties of magnetically responsive materials. The size, shape, magnetite content, aggregation state, and other factors will influence the rate at which particles of a magnetically responsive material will move in a fluid in response to an applied magnetic field. Application of the techniques of this invention to samples of magnetically responsive materials can serve as means of controlling the quality of these materials, as well as determining the quantity of these materials in an unknown sample or a sample of unknown concentration.

EMBODIMENT 10

Figure 16A:
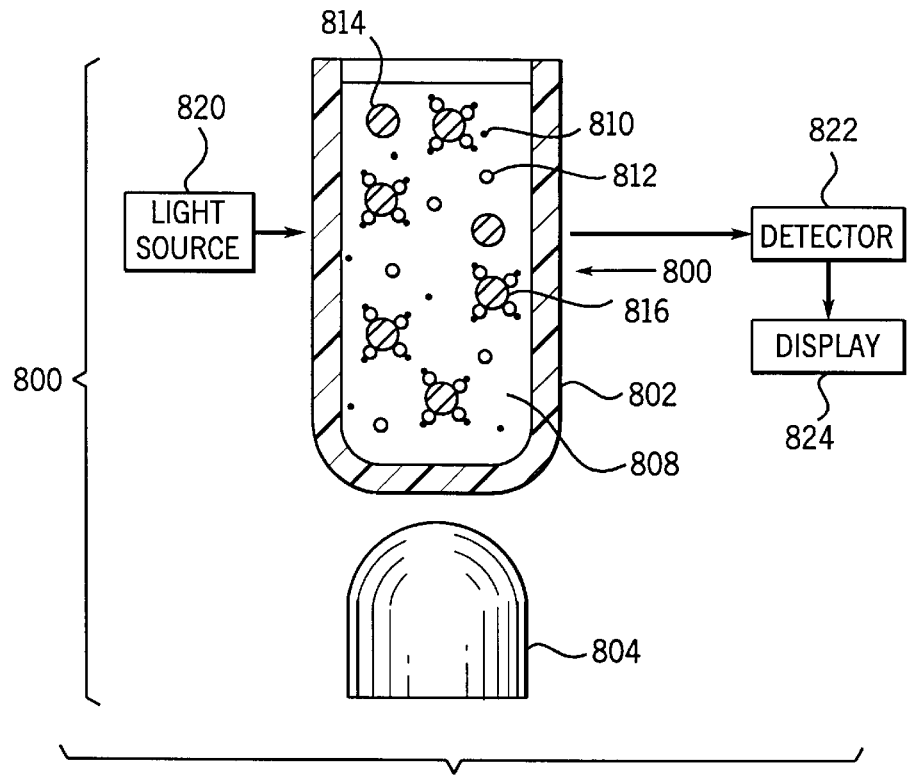
FIG. 16A is a schematic view of an optical density detection device in operation for the magnetically assisted detection of complexes containing a magnetically responsive reagent before a large number of complexes have accumulated at the bottom of the reaction vessel.
Figure 16B:
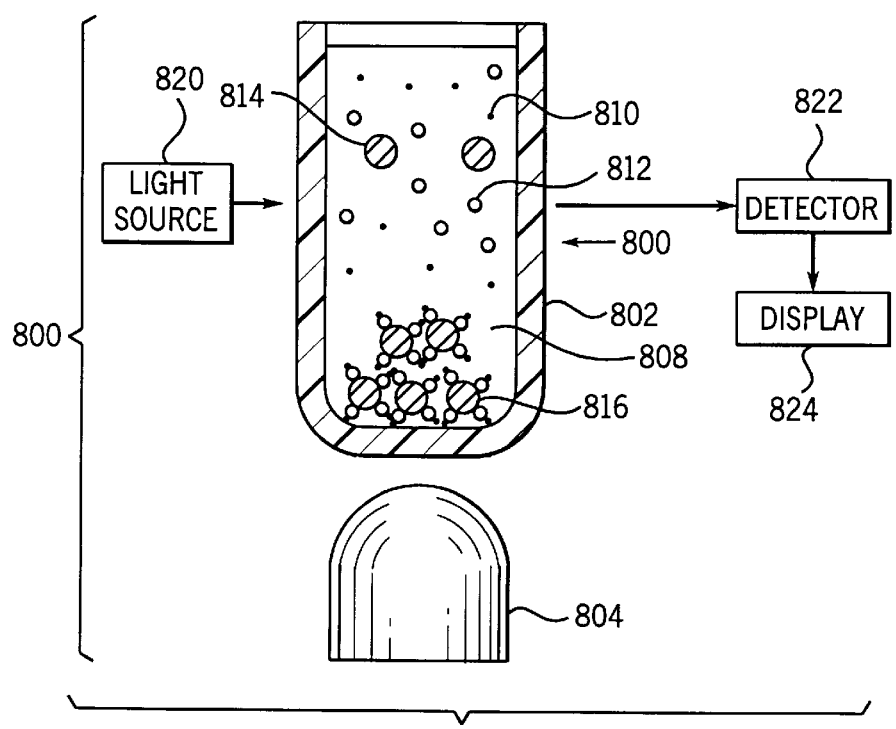
FIG. 16B is a schematic view of the device of FIG. 16A in operation for the magnetically assisted detection of complexes containing a magnetically responsive reagent after a large number of complexes have accumulated at the bottom of the reaction vessel.

In another embodiment of the present invention, FIGS. 16A and 16B illustrate a self-performing immunoassay device for performing analytical tests. The device 800 comprises a reaction vessel 802 supported above a magnet 804. The reaction vessel 802 contains a reaction mixture 808, which comprises particles of a magnetically responsive reagent 810, an analyte 812, if any, and particles of a mobile solid phase reagent 814. If analyte is present, a portion of the magnetically responsive reagent 810 binds to the mobile solid phase reagent 814 (by means of the analyte) to form complexes 816. Because the magnetic force that is exerted upon a particle of the mobile solid phase reagent that has more than one particle of magnetically responsive reagent bound to it (by means of the analyte) is greater than the force exerted upon a particle of a magnetically responsive reagent alone, the complexes 816 of the mobile solid phase reagent 814, the analyte 812, and the magnetically responsive reagent 810 move more rapidly in the magnetic field than do particles of a magnetically responsive reagent alone and are cleared from suspension.

In a preferred embodiment of this invention, particles of the mobile solid phase reagent or particles of the magnetically responsive reagent or both are fabricated so that either one, or both, can be detected when in suspension. The clearance of the complexes from suspension can be detected visually or measured using an optical device such as that shown in FIG. 16. A beam of light from a light source 820 passes through the reaction vessel 802 and the reaction mixture 808 to strike an optical detector 822. The results of the optical density measurements can be seen on a display 824. The quantity of mobile solid phase reagent 814 or magnetically responsive reagent 810 or both are determined by noting changes in optical density, fluorescence emission, light scattering or any of the methods of the other embodiments described herein, or by other means.

It is to be understood that since the present invention involves the assessment of the force, movement, or accumulation manifested by complexes of the mobile solid phase reagent and the magnetically responsive reagent, the various detection methods and reagents described herein are readily adaptable to an automated operation or system. However, such automated operation or system is not meant to exclude the possibility that some assay operations in an automated system may be carried out manually.

The present invention will now be illustrated by the following non-limiting examples.

EXAMPLES

Example 1

Modified Electronic Microbalance for Measurement of Magnetic Force

A device was designed and built to measure and automatically record forces exerted upon magnetically responsive material by applied magnetic fields. A model UMT-2 electronic microbalance 900 was obtained from Mettler-Toledo Inc., Hightstown, N.J. Referring now to FIG. 17, this balance 900 was modified at the factory to accept weights in excess of its normal range. An aluminum stalk 902 was produced to replace the normal balance pan. A circular recess 904 was machined into the top of the stalk 902 to receive a 0.25 inch diameter neodymium-iron-boron cylindrical magnet 906, obtained from Cookston Magnets. One end of the 0.25 inch long cylindrical magnet was rounded to give a slight dome shape in order to modify the shape of the magnetic field produced, so the region of maximum force on magnetically responsive particles would be in the center of the face of the magnet. An aluminum lid 908 for the weighing chamber of the microbalance was fabricated to replace the glass lid normally supplied. The lid 908 consisted of an aluminum outer ring 910 having a large central hole, which supported an aluminum disk 912, which had a diameter smaller than the diameter of the weighing chamber. The disk 912 was penetrated by two unthreaded holes 914, 916 near the edge and a larger, threaded hole 920 at the center. The disk 912 was positioned on the supporting ring 910 such that set screws 924, 926 passed through each unthreaded hole 914, 916 and screwed into threaded holes 928, 929 in the supporting ring 910. The central, threaded hole 920 in the disk 912 accepted a threaded, cylindrical aluminum insert 930 in which a central, flat-bottomed hole 932 had been bored from the top to within 0.001 inch of the bottom, leaving a thin aluminum "window" to form the floor 934 of the hole 932. The central hole 932 of the insert 930 accepted cylindrical aluminum adapters 936 with holes bored through their centers 937 to accommodate test vessels 938 of various shapes and sizes. The force measuring device was assembled by removing the pan from the balance and replacing it with the aluminum stalk 902. The shaped magnet 906 was placed in the recess 904 on the top of the stalk 902 with the rounded end uppermost. The glass top of the weighing chamber of the microbalance was replaced with the aluminum outer ring 910, with the aluminum disk 912 centered on it. The threaded aluminum insert 930 was screwed into the central threaded hole 920 in the disk 912 and a test vessel adapter 936 was inserted in it. The balance itself and all added parts were connected to ground to avoid any buildup of static charge.

Microbalance-Computer Interface for Automated Data Collection

The modified microbalance device was interfaced with the LabVIEW® data acquisition program from National Instruments, Inc., Austin Tex., residing on a Macintosh si computer by means of a cable supplied by Mettler-Toledo, Inc. The program was set up to continuously acquire, record, and display the weight readings sent from the microbalance at a rate of one reading every 0.3 seconds.

Alignment and Testing

The microbalance apparatus 900 was zeroed and data collection was begun on the attached computer. A 20 µl aliquot of a diluted suspension of superparamagnetic microparticles obtained from Nippon Paint was transferred by pipette into a polypropylene microtube, which was then placed in the aluminum test vessel holder atop the microbalance, so the bottom of the tube rested on the flat bottom of the threaded aluminum insert 930. The insert 930 was then rotated in a clockwise direction so as to cause the bottom of the insert 930 to approach the top of the magnet 906. The apparent weight of the magnet 906 reported by the balance 900 was monitored and was found to decrease as the insert 930 approached the magnet 906. This apparent change of weight resulted from the force exerted by the magnet 906 on the superparamagnetic microparticles in the microtube, which counteracted the gravitational force on the magnet 906. As the insert 930 continued to be rotated, a position was reached at which the bottom of the insert 930 made contact with the top of the magnet 906. At this point, the apparent weight of the magnet 906 dramatically increased as the insert 930 exerted downward force on it. The direction of rotation of the insert 930 then was reversed until the apparent weight of the magnet 906 returned to that observed just before contact was made. The insert 930 was then rotated an additional ten degrees in a counterclockwise direction, leaving a very small gap between the bottom of the insert 930 and the top of the magnet 906. The set screws 924, 926 holding the aluminum disk 912 containing the threaded insert 930 against the aluminum ring 910 were loosened and the disk 912 adjusted horizontally until the minimum apparent weight was reported by the balance 900; then the set screws 924, 926 were retightened. The vertical adjustment of the threaded insert 930 described above was then repeated and its position fixed by application of a drop of rubber cement to the threads. The result of these adjustments was to position the superparamagnetic microparticles in the region of the greatest vertical attractive force from the magnet 906 being weighed by the balance 900.

Figure 18:
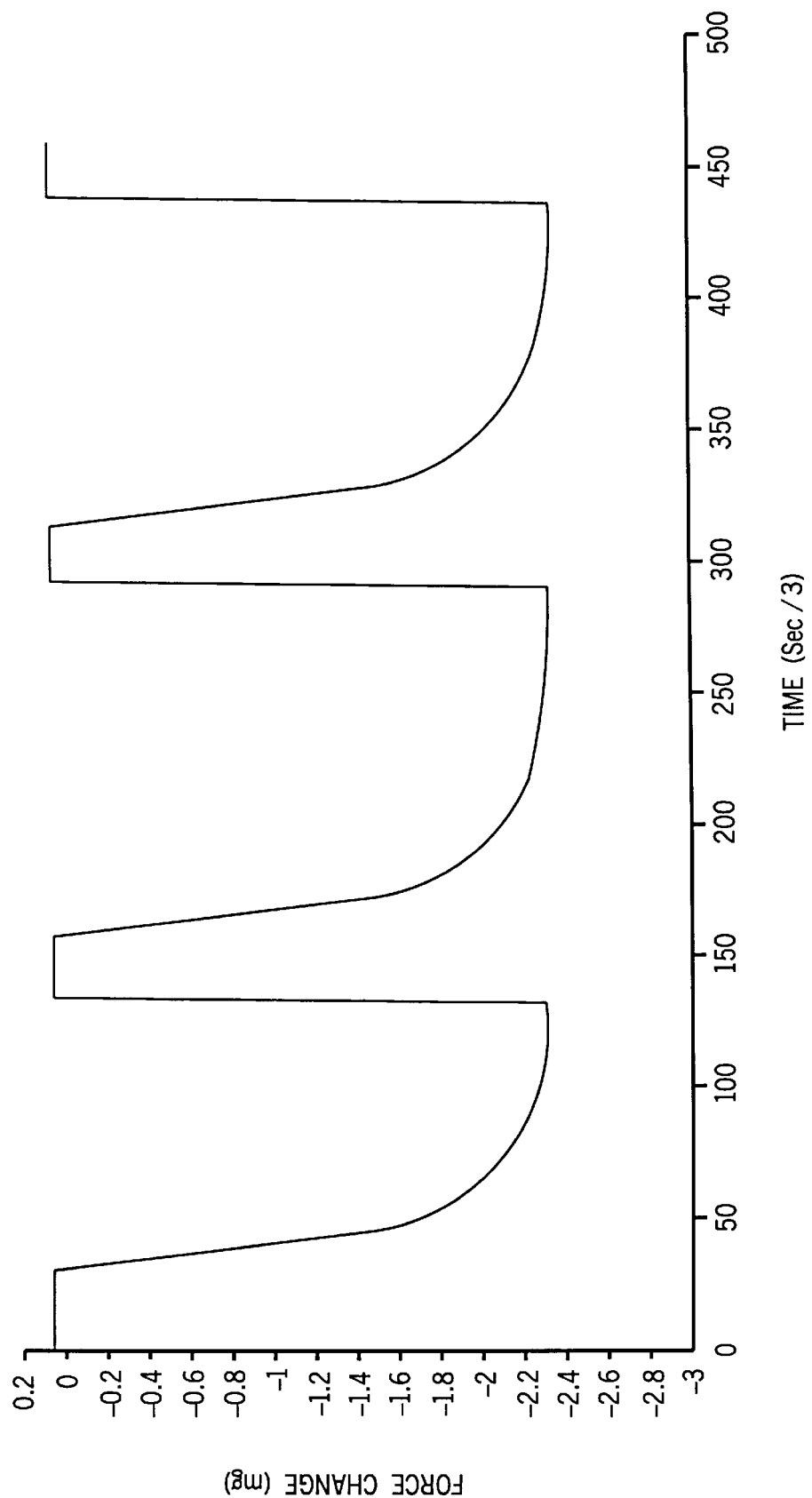
FIG. 18 is a graph illustrating the signal generated by the device illustrated in FIG. 17 during analysis of three samples of superparamagnetic microparticles.

The sensitivity and reproducibility of the balance device was tested using a 0.01% suspension (weight/volume) of superparamagnetic microparticles having a diameter of 0.8 $\mu$m and containing 30% magnetite by particle weight. Aliquots of 20 $\mu$l each were transferred to 0.5 cm×3 cm polypropylene microcentrifuge tubes (Robbins Scientific). The balance device was zeroed and data collection begun. After 10 seconds, the first tube was inserted into the device. Immediately after insertion of the tube the reported apparent weight of the magnet began to drop rapidly (see FIG. 18). About 10 seconds after insertion, the rate of weight change began to decrease until change had nearly stopped after about 30 seconds, the final change of weight being 2.4 mg. Upon removal of the microcentrifuge tube, the apparent weight quickly returned to zero. Repeating the process with two additional samples gave substantially identical results (see FIG. 18).

Example 2

Preparation of Magnetically Responsive Reagent from Aqueous Dispersible Ferrofluid and a Specific Binding Member Properties of the Ferrofluid A ferrofluid capable of forming stable aqueous dispersions was obtained from Xerox Specialty Materials, Pittsford, N.Y. This material is described in U.S. Pat. Nos. 5,322,756 and 5,358,659, incorporated herein by reference. The ferrofluid was supplied as a 60% (weight/volume) aqueous suspension. The particles of the ferrofluid were superparamagnetic and comprised a polymeric matrix, in which were embedded monodomain nanocrystals of $Fe_2O_3$, which made up 27% of the weight of the particle. Particle size varied from particle to particle. The average diameter of particles was approximately 20 nm. The magnetization of the particles was reported as 12.2 EMU/gm at 6 kilogauss.

Figure 19:
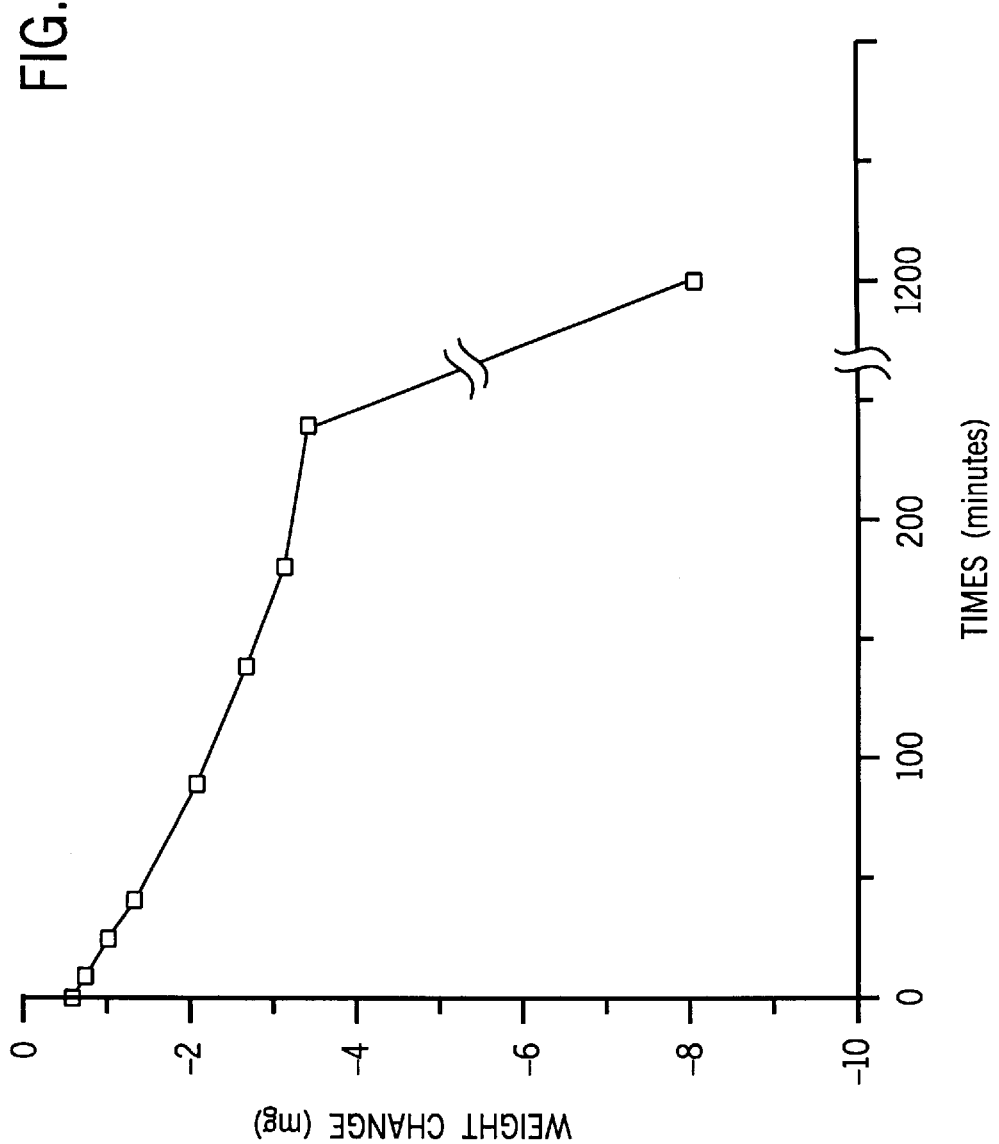
FIG. 19 is a graph illustrating the measurement of the attractive force of unbound or free magnetically responsive particles as a function of time.

The concentrated ferrofluid was diluted 100 times with water, yielding a transparent, brown suspension. A 5 $\mu$l aliquot of the diluted ferrofluid was transferred to a polypropylene microtube and placed in the balance device described in Example 1. A rapid 5.2 mg weight change was observed, equivalent to 104 mg/$\mu$l for the undiluted ferrofluid. The diluted ferrofluid was diluted a further 16 fold (1600-fold total) in water, and a 100 $\mu$l aliquot was analyzed in the balance device as described previously in Example 1. An immediate 0.5 mg weight change was observed, followed by a very slow weight change to a total weight change of 8 mg over a period of 20 hours (see FIG. 19). This result indicated the very weak force exerted upon each individual particle of ferrofluid by the applied field. Although the aggregate attractive force of all the particles in the field is sensed immediately by the balance, migration of the particles to the region of greatest field and gradient was very slow as indicated by the very slow subsequent change in weight.

Figure 20A:
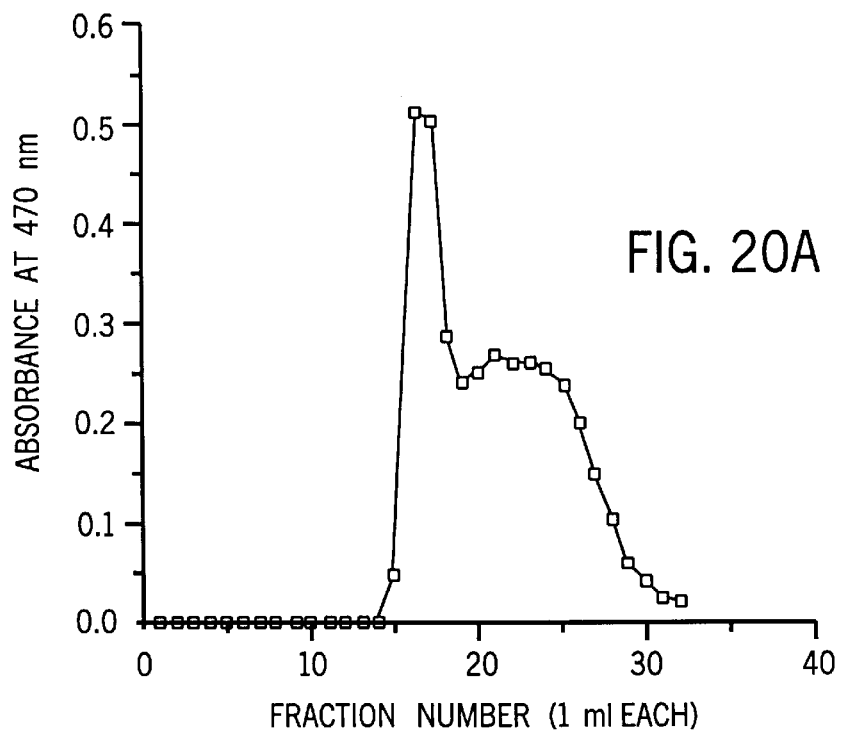
FIG. 20A is a graph illustrating the separation of ferrofluid on a column of "SEPHACRYL S-500" gel filtration media.
Figure 20B:
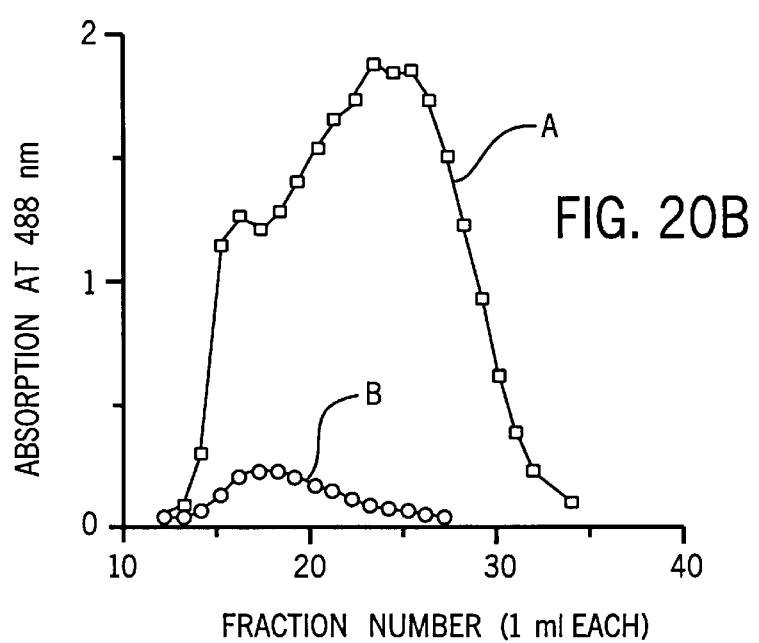
FIG. 20B is a graph illustrating the separation of ferrofluid on a column of "SEPHACRYL S-1000" gel filtration media.
Figure 22A:
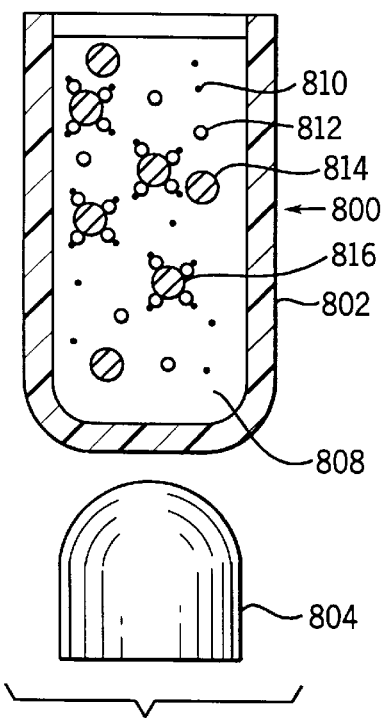
FIGS. 22A, 22B, 22C, and 22D are schematic views illustrating the observable aspects of ferrofluid binding to latex particles in a magnetic field.
Figure 22B:
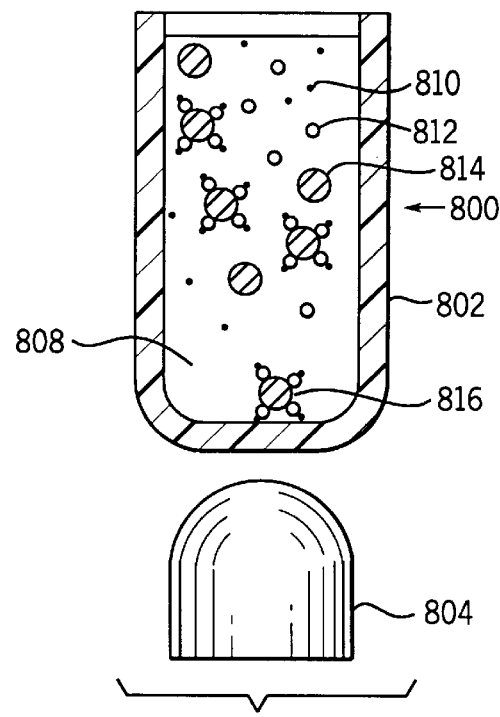
Figure 22C:
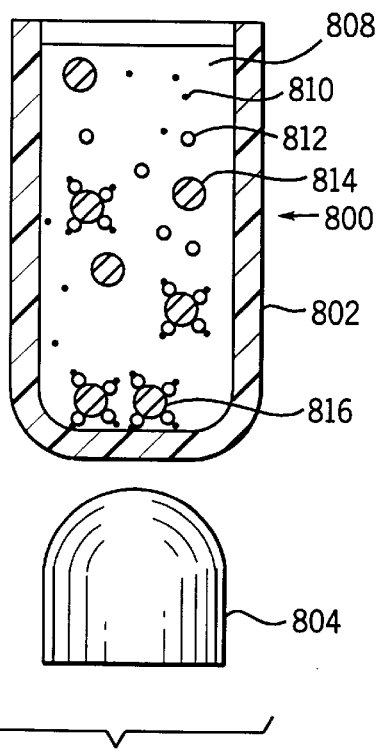
Figure 22D:
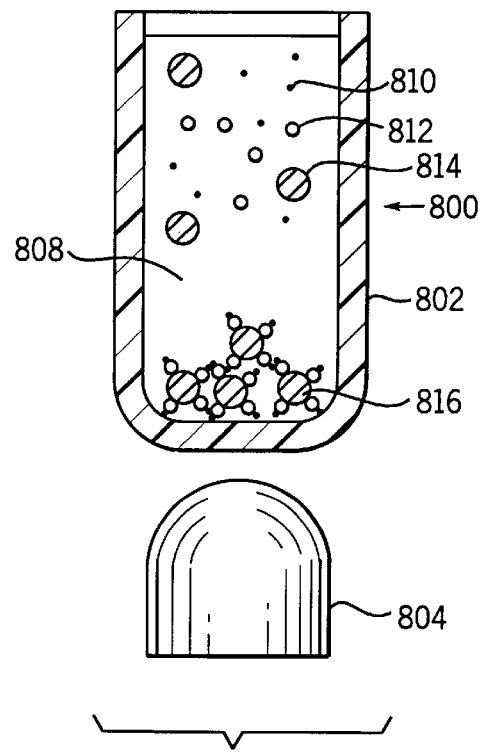

The concentrated ferrofluid was diluted 100 times with phosphate buffered saline (PBS) containing 0.1% bovine serum albumin (BSA) and applied to a 1 cm×40 cm chromatography column packed with "SEPHAROSE S-300" gel filtration media (Pharmacia Bioteck, exclusion limit 1×10$^6$ daltons) previously equilibrated with 0.1% BSA in PBS, and eluted with the same buffer. The ferrofluid eluted as a brown band in the excluded volume of the column. Separation on a column of "SEPHACRYL S-500" gel filtration media (exclusion limit 2×10$^7$ daltons) resulted in the ferrofluid being partially included (see FIG. 20A), whereas separation on a column of "SEPHACRYL S-1000" gel filtration media (exclusion limit >10$^8$ daltons) resulted in most of the particles being included, eluting as a broad band later than reference 30 $\mu$m microparticles (see FIG. 20B). In FIG. 20B, curve A represents magnetically responsive reagent and curve B represents mobile solid phase reagent. The ferrofluid could be subfractionated on the basis of particle size in this manner.

Coating of the Ferrofluid with Biotinylated BSA

In order to evaluate the utility of the ferrofluid in binding assays, the ferrofluid was coated with biotinylated BSA (albumin, bovine-biotinamidocaproyl labeled, Sigma Chemical Co., St. Louis, Mo.). A 100 $\mu$l aliquot of a 10 mg/ml solution of the biotinylated BSA in PBS was mixed with 850 $\mu$l of 1% bicarbonate buffer (pH 9.0) and 50 $\mu$l of the concentrated ferrofluid. The mixture was incubated at a temperature of 37° C. for one hour, then 200 $\mu$l of 1% BSA in PBS was added, and incubation continued for an additional 45 minutes. The mixture was then applied to a 1 cm×40 cm chromatography column packed with "SEPHAROSE S-300" gel filtration media previously equilibrated with 0.1% BSA in PBS, and eluted with the same buffer. Fractions containing the ferrofluid, as indicated by their brown color, eluted at the column void volume. A 5 $\mu$l aliquot of the pooled fractions gave a reading of 5 mg in the balance device. The pooled material was diluted 50 times with PBS for use in binding assays (see Examples 3, 4, 5, 6, 7, and 8 below).

Coating the Ferrofluid with Anti-hCG

An antibody with binding activity against the beta subunit of human chorionic gonadotropin was obtained from Abbott Laboratories and labeled with tritium by periodate oxidation, followed by reduction with $NaCNBH_3(^3H)$. Following application to a 1 cm×40 cm column of "SEPHAROSE S-300" gel filtration media (Pharmacia Bioteck), the label eluted in three peaks in the excluded volume, the partially included volume, and the totally included volume, representing labeled antibody aggregates, free labeled antibody, and free label, respectively. A 10 µl aliquot of the unseparated labeled antibody (340,000 dpm) was mixed with a 20 µl aliquot of ferrofluid in 220 µl of 1% sodium carbonate buffer, pH 9.0. After incubation for two hours at a temperature of 37° C., 800 µl of 0.1% BSA in PBS was added and incubation continued for 45 minutes at a temperature of 37° C. The mixture was then applied to the column of "SEPHAROSE S-300" gel filtration media as described above. The label eluted as two peaks, one eluting with the ferrofluid at the excluded volume and one at the totally included volume. The coating procedure was repeated with unlabeled anti-hCG antibody. The material eluting at the excluded volume was collected and diluted fifty times with PBS for use in immunoassays.

Preparation of Antibody-Coated Poly(pyrrole) Latex Particles

A sample of polypyrrole latex particles coated with an antibody with binding affinity for biotin was prepared as described in U.S. Pat. No. 5,252,459, incorporated herein by reference. These particles were from 0.3 to 0.7 µm in diameter and suspensions of them are intensely black in color.

Example 3

Effect of Ferrofluid Binding to Latex Particles on Behavior in a Magnetic Field

Five aliquots (one ml each) of the fifty-fold diluted biotinylated BSA coated ferrofluid from the column containing "SEPHAROSE S-300" gel filtration media (see Example 2) were transferred to glass vials having a capacity of 4 ml. Aliquots of 0, 2, 5, 10, and 20 µl of a 0.1% suspension of the anti-biotin coated polypyrrole latex were transferred to each vial containing the biotinylated BSA coated ferrofluid, and the contents of each vial incubated at a temperature of 37° C. for 30 minutes. An aliquot (100 µl) from each vial was then transferred to a polypropylene microtube, the microtube placed in the microbalance apparatus described in Example 1, and the apparent weight of the magnet recorded as a function of time.

Both the rate and the extent of the apparatus response reflected the quantity of anti-biotin coated polypyrrole latex present (see FIG. 21). The balance was set to zero and data collection began at 0 seconds (see FIG. 21). The polypropylene microtube containing the aliquot from the incubated mixture with no added anti-biotin coated polypyrrole latex (the zero microliter sample) was inserted into the apparatus after 45 seconds. The reported weight of the magnet rapidly decreased from 0 mg to −0.06 mg, then further decreased at a steady rate to −0.10 mg over a period of three minutes, reflecting the rate of migration of the ferrofluid to the bottom of the microtube (see curve segment A, FIG. 21). The microtube was then withdrawn from the apparatus and the reported weight of the magnet quickly returned to zero.

The polypropylene microtube containing the aliquot from the incubated mixture having two microliters of antibiotin coated polypyrrole latex added was inserted into the apparatus after an additional 30 seconds. The reported weight of the magnet quickly dropped from 0 to −0.06 mg, then further decreased at a steady rate to −0.12 mg over a period of three minutes (see curve segment B, FIG. 21), whereupon it was withdrawn. Analysis of microtubes containing aliquots from the incubated mixtures having 5, 10, and 20 microliters of anti-biotin coated polypyrrole latex added (see curve segments C, D, and E, FIG. 21) showed increasingly greater rates of decrease in reported magnet weight, reflecting the greater rate of migration of the ferrofluid when in ferrofluid-polypyrrole latex complexes than that of the ferrofluid alone (see Table 1).

TABLE 1

| Volume of polypyrrole (µl) | Weight after three minutes (mg) | Rate of change (µg/sec) |
|---|---|---|
| 0 | −0.10 | −0.25 |
| 2 | −0.12 | −0.38 |
| 5 | −0.16 | −0.63 |
| 10 | −0.22 | −1.13 |
| 20 | −0.38 | −2.25 |

The linear rate of the weight changes over the three minute periods of observation indicated that capture of the complexes was not completed in this time. Over longer periods of observation, the more rapid weight change of the samples containing greater concentrations of polypyrrole latex slowed to that of the zero sample, indicating that all the complexes had migrated to the bottom of the microtube. The slow rate of weight change seen with the zero sample was due to aggregation of the ferrofluid particles during the coating procedure with biotinylated bovine serum albumin and can be reduced by prior sonication.

The effect was also observable visually by noting the rate and extent of clearance of the polypyrrole latex from the test sample (see FIGS. 22A, 22B, 22C, and 22D). In all samples containing polypyrrole latex, all of the latex was cleared from the test sample, indicating the presence of an excess of ferrofluid in all samples. In the series of FIGS. 22A, 22B, 22C, and 22D, FIG. 22A precedes FIG. 22B, FIG. 22B precedes FIG. 22C, and FIG. 22C precedes FIG. 22D.

In order to determine the optimal concentration of ferrofluid required to confer magnetic responsiveness upon polypyrrole latex, the biotinylated BSA coated ferrofluid from the column containing "SEPHAROSE S-300" gel filtration media was diluted 50-fold, 100-fold, 200-fold, 400-fold, and 800-fold with PBS. All the diluted solutions were transparent, the 50-fold dilution being straw colored, the 100-fold dilution being light yellow in color, the 200-fold diluted solution being very light yellow in color, and the 400-fold and 800-fold diluted solutions being colorless. For each diluted solution, an aliquot (1 ml) was transferred to a 4 ml vial, and 20 µl of the anti-biotin coated polypyrrole suspension were then added to each vial. After incubation for 30 minutes at a temperature of 37° C., a 100 µl aliquot of each test mixture was transferred to a microtube, and the microtube inserted into the microbalance apparatus described in Example 1. In all test samples containing ferrofluid, all of the polypyrrole latex eventually migrated to the bottom of the microtube, as determined visually. The rate and extent of the apparent weight change of the magnet as reported by the apparatus varied with the concentration of the ferrofluid (see FIG. 23). These results indicate that although the more highly diluted ferrofluid suspensions were capable of binding sufficient numbers of ferrofluid particles to the polypyrrole latex particles to allow the complexes to be captured magnetically, the use of more concentrated ferrofluid suspensions resulted in a higher loading of ferrofluid on the polypyrrole latex.

Example 4

Inhibition Assay for Free Biotinylated BSA

Figure 24:
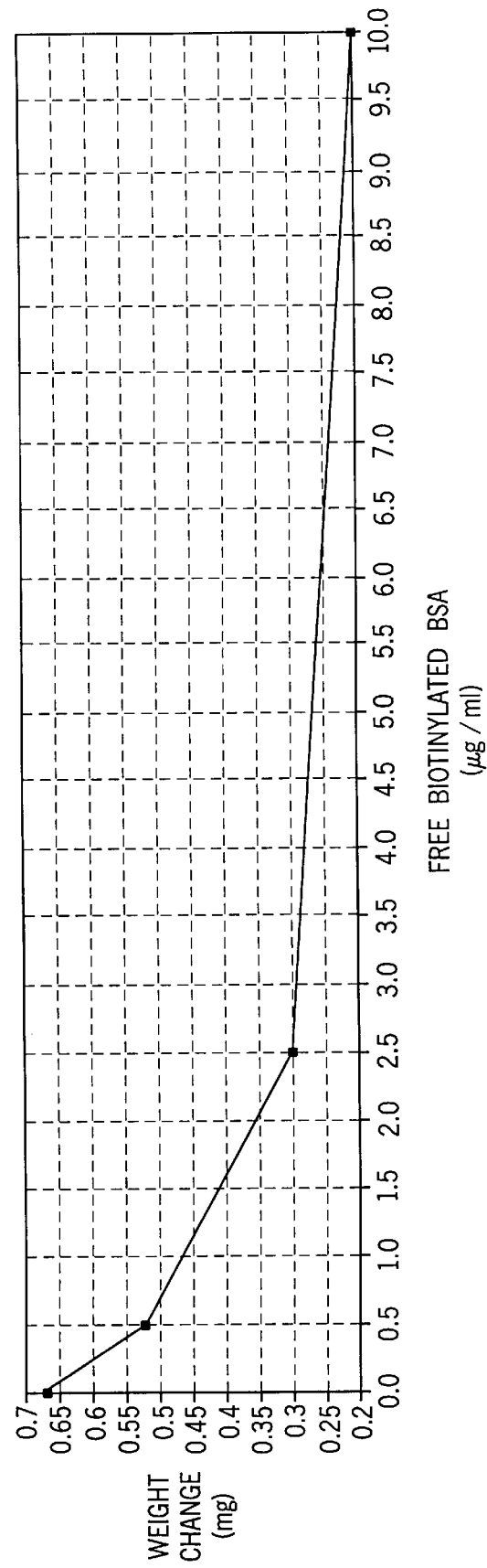
FIG. 24 is a graph illustrating the apparent weight change of a magnet resulting from capture of complexes of polypyrrole and magnetically responsive reagent during an assay for free biotinylated bovine serum albumin.

Diluted solutions of free biotinylated BSA were made with an assay diluent obtained from Abbott Laboratories to give concentrations of 0 µg/ml, 2 µg/ml, 10 µg/ml, and 40 µg/ml. For each diluted solution, an aliquot (20 µl) was placed in a microtube and mixed with 20 µl of the anti-biotin coated polypyrrole latex. After each solution was incubated for one hour at a temperature of 37° C., 40 µl of the biotinylated BSA coated ferrofluid was added to each solution, incubation continued for an additional 30 minutes, then each tube placed in the microbalance apparatus described in Example 1 for analysis. The observed apparent weight change of the magnet with the tubes in place relative to the apparent weight of the magnet when a microtube containing 40 µl of diluent instead of the ferrofluid was in place was noted. As shown in FIG. 24, increasing concentrations of free biotinylated bovine serum albumin inhibits the capture of the ferrofluid by the polypyrrole latex, with the result that fewer complexes are formed and less ferrofluid accumulates at the bottom of the microtube where it can exert its greatest attractive force upon the magnet. The 40 µg/ml sample (10 µg/ml in the incubated mixture) showed a weight change of 0.2 mg, indicating maximum inhibition under these conditions was obtained at biotinylated bovine serum albumin concentrations of 4–5 µg/ml in the incubated mixture.

These results demonstrate that the ferrofluid and the polypyrrole latex are binding to one another because of the specific binding members with which they are coated. The extent of the binding causes a predictable change in the effect of an applied magnetic field upon the test mixture.

Example 5

Figure 25B:
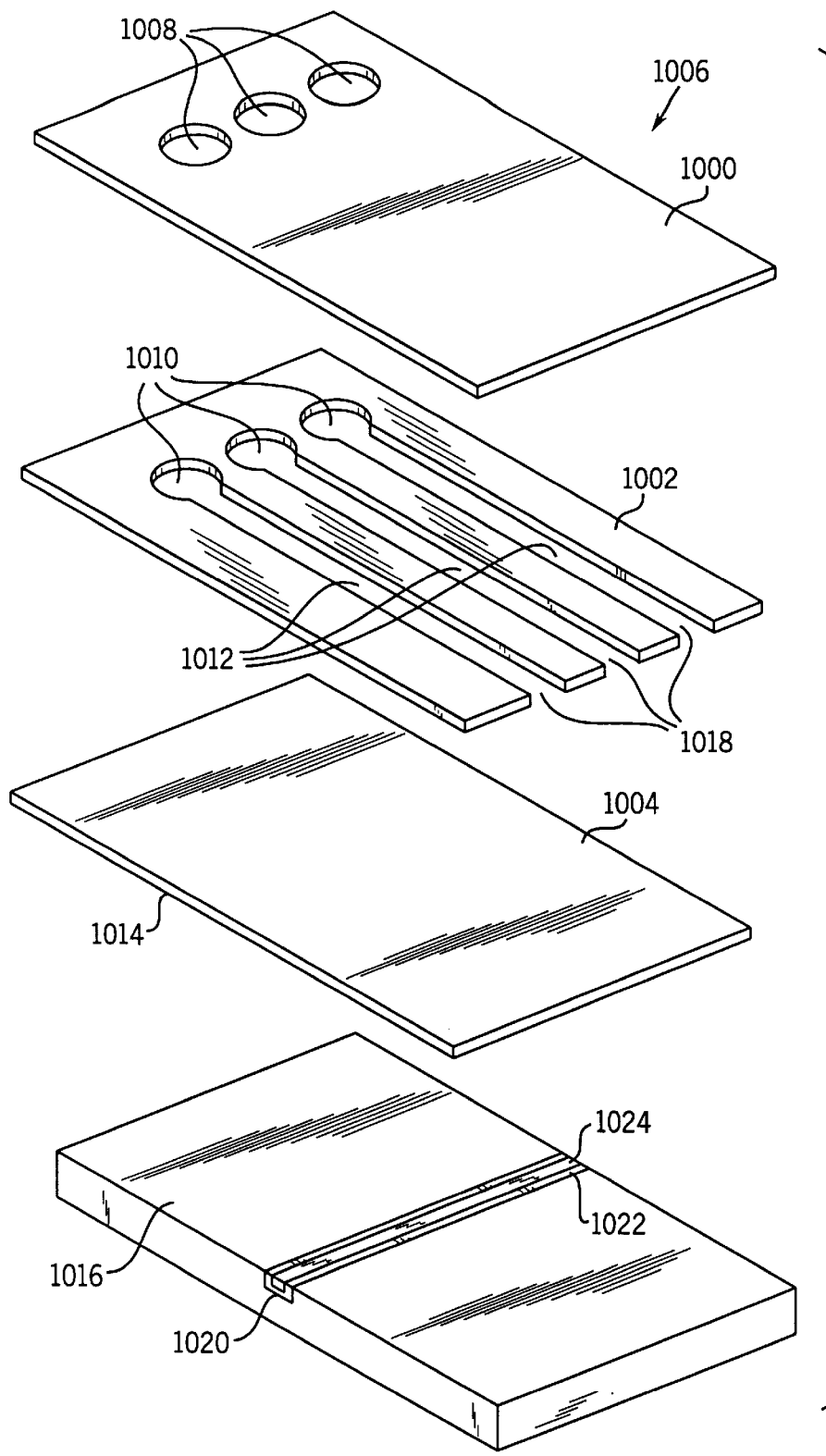
FIG. 25B is an exploded perspective view of the self-performing immunoassay device of FIG. 25A.

Fabrication of Device Having Capillary Channels for Self Performing Immunoassays Referring now to FIGS. 25A, 25B, and 25C, three sheets 1000, 1002, and 1004 of polymeric film were laminated together to create a capillary channel laminate 1006. One or more opening holes 1008 in the top sheet 1000 served as application site(s) for the test sample, allowing it access to the proximal end(s) 1010 of the channel(s) 1012 cut in the middle sheet 1002. The bottom 1014 of the bottom sheet 1004 was coated with adhesive so that it would adhere to a magnetic base plate 1016, which is described below. The test sample was drawn down the channel 1012 by capillary action until it reached the end(s) 1018 of the channel(s) 1012, at which point movement of liquid down the channel would cease. A porous wicking material (not shown) was sometimes positioned at the end(s) 1018 of the channel(s) 1012 in order to continue drawing the test sample down the channel after the end of the channel had been reached.

While the device in this example is made by adhering three layers of polymeric material together, it is within the scope of this invention to make devices having capillary channels with a single layer, two layers, or four or more layers of polymeric or equivalent material, such as, for example, glass or metal foils. Means of adhering two or more layers of polymeric or equivalent material are well-known to one or ordinary skill in the art, such as, for example, adhesives, heat-sealing, fasteners, and the like.

Fabrication of A Magnetic Base Plate to Support the Capillary Channels

A 20 cm×20 cm base plate was machined from ½-inch aluminum plate 1016. A channel 1020 (½-inch wide and ¼-inch deep) was machined across the face of the plate, which channel was filled with a "DELRIN" insert 1022. A channel ⅛-inch deep by ¹⁄₃₂-inch wide was cut lengthwise across the center of the insert 1022 and filled with a ⅛-inch×¹⁄₃₂-inch×6-inch strip 1024 of flexible magnetic material.

Example 6

Capture of Polypyrrole Latex at a Magnetic Site in a Capillary Channel as a Result of Complex Formation with Ferrofluid In order to determine the optimal concentration of ferrofluid required to confer magnetic responsiveness upon polypyrrole latex for use in an assay format employing a device having capillary channels, the biotinylated BSA coated ferrofluid from the column containing "SEPHAROSE S-300" gel filtration media was diluted 50-fold, 100-fold, 200-fold, 400-fold, and 800-fold with PBS. For each diluted solution, an aliquot (1 ml) was transferred to a 4 ml vial, and 20 µl of the anti-biotin coated polypyrrole suspension was added to each vial. After incubation for minutes at a temperature of 37° C., a 7 µl aliquot from each vial was then applied to the application site of the capillary channel laminate, which had been attached to the magnetic base plate such that the long axis of the magnetic strip was oriented 90° from the long axis of the channels, and was positioned beneath the channels 0.5 cm distal to the proximal channel opening (see FIGS. 25A and 25B). All channels corresponding to test samples containing the diluted solutions of ferrofluid showed a black band of captured polypyrrole latex at the position of the magnetic strip, the intensity of the band increasing as the concentration of the ferrofluid in the test sample increased. Test samples containing no ferrofluid showed no band of the polypyrrole latex.

Example 7

Qualitative Inhibition Assay for Free Biotinylated BSA Performed Using a Device Having Capillary Channels Four separate solutions containing 0 µg, 5 µg, 20 µg, and 80 µg of the biotinylated BSA described in Example 4 in 1 ml PBS were prepared. An aliquot (20 µl) of the anti-biotin coated polypyrrole latex described in Example 2 was added to each mixture, followed by incubation at a temperature of 37° C. for one hour, whereupon a 20 µl aliquot of the biotinylated BSA coated ferrofluid from Example 2 was added. After incubation at a temperature of 37° C. for 5 minutes or 25 minutes, aliquots were applied to the capillary channel device described in Example 5. The presence of free biotinylated BSA at a concentration of 5 µg/ml or more inhibited the capture of the polypyrrole latex at the magnetic site of the channels.

Example 8

Quantitative Inhibition Assay for Free Biotin Performed Using a Device Having Capillary Channels Diluted solutions of the biotinylated BSA described in Example 4 were made in assay diluent to concentrations of 0 µg/ml, 5 µg/ml, 10 µg/ml, 20 µg/ml, and 80 µg/ml. A 20 µl aliquot of each diluted biotinylated BSA solution was further mixed with 60 µl of diluent and 10 µl of the anti-biotin coated polypyrrole latex described in Example 2. After the mixture was allowed to stand 15 minutes at room temperature, a 10 µl aliquot of the biotinylated BSA coated ferrofluid from Example 2 was added thereto. After further incubation at a temperature of 20° C. for 15 minutes, aliquots (7 µl) of the resulting mixture were applied to the capillary channel device described in Example 5. The presence of free biotinylated BSA at a concentration of 5 µg/ml or more inhibited the capture of polypyrrole latex at the magnetic site of the channels.

Figure 26:
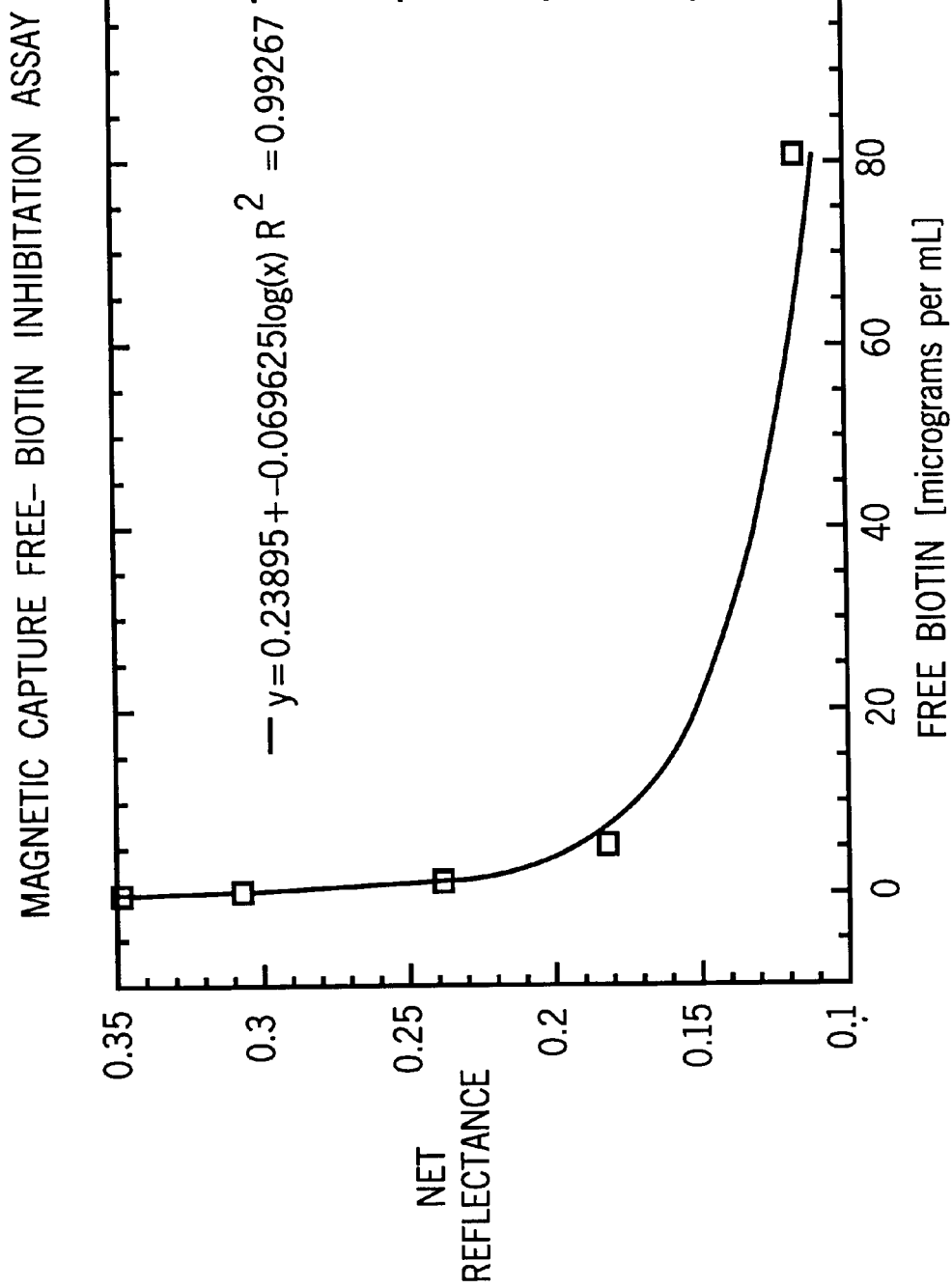
FIG. 26 is a graph illustrating the results obtained from using a device of the type shown in FIGS. 25A, 25B, and 25C by means of a reflectance reader.

Quantitative results could be obtained for this type of assay by measuring the change in reflectance of the magnetic capture site due to the presence of captured polypyrrole latex. The assay was repeated as above, except that biotinylated BSA concentrations of 0.125 µg/ml, 1.0 µg/ml, 5.0 µg/ml, and 80 µg/ml were used. After applications of aliquots (7 µl) of the reaction mixtures to the capillary channels, the channels were scanned using a scanning reflectance reader fabricated at Abbott Laboratories. Reflectance at the magnetic capture site was compared to the reflectance of sites on either side of the magnetic capture site and the net reflectance calculated as the difference between the reflectance at the magnetic capture site and the average of the two neighboring sites. The difference between the reflectance at the magnetic capture site and the neighboring, non-magnetic sites decreased as the concentration of free biotinylated BSA increased, because the free biotinylated BSA inhibited binding between the polypyrrole latex and the ferrofluid (see FIG. 26). The assay response shows the narrow range desirable for a positive/negative assay format.

Example 9

A Self-Performing Spot Immunoassay for Human Chorionic Gonadotropin Coating Ferrofluid with Antibody Ferrofluid was diluted in 20 mM 3-(N-morpholino) propanesulfonic acid (MOPS), which had been adjusted to pH 7.0 with HCl, to a concentration of 1% solids. All further steps with the ferrofluid up to the final assay were performed in this buffer. Soluble material and particles without attached iron were removed from the ferrofluid preparation by applying a layer of 3.3 ml of the 1% suspension onto 10 ml of 20% sucrose in a 15-ml centrifuge tube. The preparation was centrifuged for two hours in a swinging bucket rotor at 170,000×g at a temperature of 4° C. The pellet resulting therefrom was washed twice in 10 ml of buffer, following which, the pellet was centrifuged at 170,000×g for one hour. The final pellet was suspended in MOPS buffer to provide a concentration of 1% solids and then stored at a temperature of 4° C.

A murine monoclonal antibody which bound to the alpha subunit of β hCG was adjusted to a concentration of 4 mg/ml; five ml of this solution were added to an equal volume of the suspension of washed superparamagnetic particles. This suspension was agitated at ambient temperature on a platform shaker at 160 RPM for one hour. The coated particles were washed twice by centrifugation at 170,000×g for 30 minutes at a temperature of 4° C., suspended to form a suspension containing 1% solids, and sonicated in an ice/water bath for 15 seconds. Sodium azide was added to a provide a final concentration of 0.01%; the particles were stored at a temperature of 4° C. For use as a control in some experiments, superparamagnetic particles were similarly coated with bovine serum albumin (BSA).

Coating Latex Particles with Antibody

Blue latex particles, 3 µm in diameter, were obtained from Polysciences, Inc., Warrington, Pa. The particles were diluted to 0.1% solids in 20 mM MOPS buffer containing 0.1M NaCl (MOPS-NaCl). The particles were washed once by centrifugation at 17,000×g for 30 minutes at a temperature of 4° C., and suspended in buffer to a concentration of 0.4% solids. Affinity purified goat IgG reactive with the beta subunit of hCG was adjusted to a concentration of 250 µg/ml in MOPS-NaCl buffer. Equal volumes of latex particles and antibody solution were mixed and agitated on a platform shaker at 160 RPM for one hour at ambient temperature. The coated latex particles were washed twice and suspended in buffer to a concentration of 0.4% solids in MOPS-NaCl buffer containing sodium azide. Latex particles were coated with BSA by the same procedure for use as a control. All coated particles were stored at a temperature of 4° C.

Assay with Clinical Specimens

An assay was run with 10 urine specimens from pregnant women and 10 specimens from women who were not pregnant. The coded specimens were run in a blind experiment. Positive controls containing a hCG at a concentration of 64 ng/ml and negative controls were tested along with the clinical specimens. Independently, all specimens were evaluated in the Abbott Test-Pack Plus assay to confirm the presence or absence of β hCG at quantities consistent with pregnancy.

The assay was performed by mixing: (a) 30 µl of the IgG-coated blue 3 µm latex particles that had been diluted to 0.2% solids in MOPS-NaCl buffer containing 1.0 mg bovine serum albumin per ml (MOPS-NaCl-BSA), (b) 10 µl of monoclonal antibody-coated magnetic particles at 0.0066% solids in MOPS-NaCl-BSA, and (c) 40 µl of undiluted urine specimen. The mixture was allowed to stand for 15 minutes at ambient temperature, after which period 15 µl were spotted on Teflon tape overlying the magnetic strip of the magnetic base plate described in Example 5 and depicted in FIG. 25. A glass cover slip was placed upon two 0.5-mm thick supports on either side of the Teflon tape in order to create a reaction chamber having an optically flat viewing surface (see FIG. 15A and 15B). Results were recorded after 5 minutes and 10 minutes. When the assay was performed with the 10 positive specimens and the positive control, a collection of blue particles conforming in shape to the magnetic field was observed. In contrast, the blue particles remained homogeneously dispersed when the negative specimens and the negative control were tested. Results obtained with the Test-Pack Plus assay were in agreement with those of the assay of the invention.

Example 10

Self-Performing Assay for Soluble Fibrin Utilizing Optical Density Measurements

A self-performing assay for soluble fibrin in human plasma was developed. The assay was based on the rate of optical density change of a suspension of polypyrrole latex coated with a specific binding member and ferrofluid coated with a specific binding member under the influence of an applied magnetic field. Polypyrrole latex (0.2 µm diameter, 2% solids) was produced at Abbott Laboratories (see Example 2). A first antibody having binding affinity for an epitope on human soluble fibrin and a second antibody having binding affinity for a different epitope on human soluble fibrin were obtained from American Biogenetic Sciences (Boston, Mass.). An aliquot of the first antibody (125 µl, 5.58 mg/ml) was mixed with 0.1M borate buffer (187 µl, pH 10.0), 1% "BRIJ 35" surfactant (375 µl), polypyrrole latex (1.87 ml) and water (1.2 ml). After the mixture had been incubated with rocking for two hours at room temperature, 1.25 ml of 4% bovine serum albumin in 0.25M Bis Tris buffer (pH 7.0) and 555 µl of 0.3M periodic acid in 0.5M triethanolamine were added, and the resulting mixture incubated for an additional two hours at room temperature. The mixture was then circulated through a "MICROGON" diafiltration apparatus to exchange the liquid portion of the mixture with 25 mM MOPS-ethanolamine buffer (pH 7.2) containing 0.5% bovine serum albumin and 0.1% "BRIJ 35" surfactant. The antibody coated polypyrrole latex was stored in this solution. A diluent solution containing 0.5% bovine serum albumin, 5% sucrose, 0.1% "TWEEN 20" surfactant and 0.05% "PROCLIN" preservative in phosphate buffered saline was used to dilute the soluble fibrin standard and the stock polypyrrole solution. The stock polypyrrole suspension was diluted twelve fold with diluent for use in the assay.

An aliquot (250 µl) of the ferrofluid described in Example 2 was diluted to a concentration of 3% solids in 0.05M sodium carbonate (pH 9.1) and mixed with a solution of the second antibody (2 µl, 14.7 µg/ml). After the mixture was incubated at 37° C. for one hour, 1% bovine serum albumin (110 µl) was added, and the resulting mixture incubated for an additional 45 minutes at 37° C. The mixture was then applied to a 1 cm×40 cm column packed with "SEPHACRYL S-300" gel permeation media and equilibrated with phosphate buffered saline containing 0.1% bovine serum albumin. The column was eluted with the same buffer and the excluded material was recovered in 3 ml.

The assay reagent mixture was prepared by mixing 1 ml of the diluted antibody coated polypyrrole suspension with 100 µl of the antibody coated ferrofluid suspension.

Assay standards were prepared from human soluble fibrin (obtained from American Biogenetic Sciences) diluted to different concentrations with the diluent solution.

A Cary 3 spectrophotometer was used to determine the optical density of the assay mixture. A 5 mm inside diameter×30 mm fluorometer cuvette was obtained from Wilmad Glass Inc. A hex-head cap screw was screwed into the threaded hole in the bottom of the spectrophotometer's cuvette holder and a 0.25 inch×0.25 inch neodymium-iron-boron magnet placed on top of it. The position of the magnet in the cuvette holder was then adjusted by turning the cap screw until the magnet just began to block the bottom portion of the light beam through the cuvette holder (as judged by a decrease in the apparent optical density reported by the instrument). The top and bottom portion of the light beam was blocked by horizontal strips of electrical tape until a vertical gap of 3 mm remained, the bottom of which aligned with the inside floor of the fluorometer cell when inserted in the cuvette holder until it rested upon the top of the magnet. The reference cuvette holder was similarly blocked. The instrument was zeroed before the assay was begun.

Figure 27:
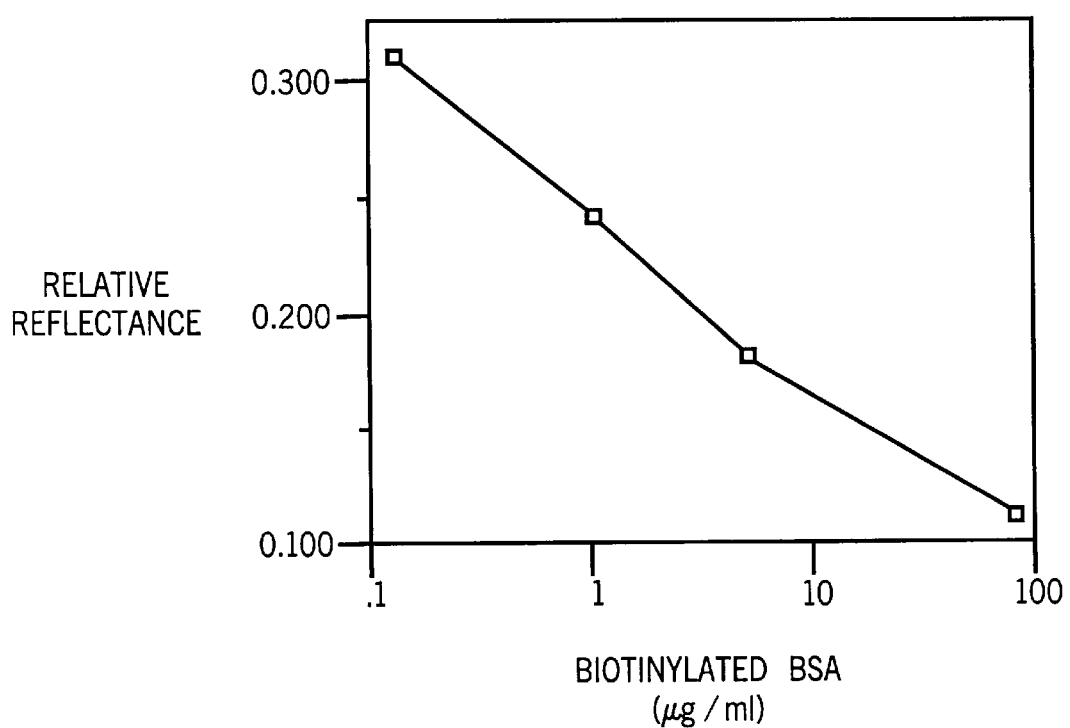
FIG. 27 is a graph illustrating the results obtained from using a self-performing immunoassay device for soluble fibrin by means of an optical density reader.

The assay was performed by first mixing 50 µl of the assay reagent mixture with 50 µl of the test mixture and then transferring the resulting mixture to the cuvette. The cuvette was then inserted into the cuvette holder until its bottom rested upon the magnet, and the continuous collection of optical density data by the spectrophotometer begun immediately. The rate of clearance of the polypyrrole latex from the solution by magnetic capture was reflected in the rate of change of the optical density of the suspension. A plot of the rate of optical density change in the assay mixture as a function of soluble fibrin concentration in the test sample shows a linear relationship (see FIG. 27).

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the presence or amount of an analyte in a test sample, said method comprising the steps of:
   (a) contacting said test sample with both a mobile solid phase reagent and a magnetically responsive reagent to form a reaction mixture, said analyte being capable of specifically binding to both said mobile solid phase reagent and said magnetically responsive reagent to form a complex comprising said mobile solid phase reagent, said magnetically responsive reagent, and said analyte;
   (b) subjecting said reaction mixture to a magnetic field such that a magnetic force is exerted upon said complex if said complex is present in said reaction mixture, the influence of said magnetic force being manifested by the movement or capture of said complex at a different rate from that of said magnetically responsive reagent alone or from that of said mobile solid phase reagent alone; and
   (c) measuring the degree of said manifestation to provide a measure of the presence or amount of said analyte in said test sample.

2. The method of claim 1, wherein said test sample is sequentially contacted with said mobile solid phase reagent and said magnetically responsive reagent.

3. The method of claim 1, wherein said test sample is simultaneously contacted with said mobile solid phase reagent and said magnetically responsive reagent.

4. The method of claim 1, wherein the degree of manifestation is determined by detecting an apparent weight change of said attached magnetically responsive reagent in said magnetic field.

5. The method of claim 4, wherein a balance is used to detect said apparent weight change.

6. The method of claim 1, wherein a visual device is used to determine said degree of manifestation.

7. The method of claim 1, wherein an optical device is used to determine said degree of manifestation.

8. The method of claim 1, wherein a position sensing device is used to determine said degree of manifestation.

9. The method of claim 1, wherein said degree of manifestation is determined visually.

10. The method of claim 1, wherein said magnetically responsive reagent comprises superparamagnetic material attached to a specific binding member.

11. The method of claim 10, wherein said superparamagnetic material is a ferrofluid.

12. A method for determining the presence or amount of an analyte in a test sample, said method comprising the steps of:
   (a) contacting said test sample with a magnetically responsive reagent and a mobile solid phase reagent to form a reaction mixture, said analyte being capable of specifically binding to said magnetically responsive reagent to form a first complex comprising said analyte and said magnetically responsive reagent and said magnetically responsive reagent being capable of specifically binding to said mobile solid phase reagent to form a second complex comprising said magnetically responsive reagent and said mobile solid phase reagent;
   (b) subjecting said reaction mixture to a magnetic field such that a magnetic force is exerted upon said complexes if either of said complexes is present in said reaction mixture, the influence of said magnetic force being manifested by the movement or capture of said second complex at a different rate from that of said magnetically responsive reagent alone or from that of said mobile solid phase reagent alone or said first complex; and (c) measuring the degree of the manifestation to provide a measure of the presence or amount of said analyte in said test sample.

13. The method of claim 12, wherein said test sample is sequentially contacted with said mobile solid phase reagent and said magnetically responsive reagent.

14. The method of claim 12, wherein said test sample is simultaneously contacted with said mobile solid phase reagent and said magnetically responsive reagent.

15. The method of claim 12, wherein the degree of manifestation is determined by detecting an apparent weight change of said attached magnetically responsive reagent in said magnetic field.

16. The method of claim 15, wherein a balance is used to detect said apparent weight change.

17. The method of claim 12, wherein a visual device is used to determine said degree of manifestation.

18. The method of claim 12, wherein an optical device is used to determine said degree of manifestation.

19. The method of claim 12, wherein a position sensing device is used to determine said degree of manifestation.

20. The method of claim 12, wherein said degree of manifestation is determined visually.

21. The method of claim 12, wherein said magnetically responsive reagent comprises superparamagnetic material attached to a specific binding member.

22. The method of claim 21, wherein said superparamagnetic material is a ferrofluid.

23. A method for determining the presence or amount of an analyte in a test sample, said method comprising the steps of:

(a) contacting said test sample with a magnetically responsive reagent and a mobile solid phase reagent to form a reaction mixture, said analyte being capable of specifically binding to said mobile solid phase reagent to form a first complex comprising said analyte and said mobile solid phase reagent and said magnetically responsive reagent being capable of specifically binding to said mobile solid phase reagent to form a second complex comprising said magnetically responsive reagent and said mobile solid phase reagent;

(b) subjecting said reaction mixture to a magnetic field such that a magnetic force is exerted upon said complexes if either of said complexes is present in said reaction mixture, the influence of said magnetic force being manifested by the movement or capture of said second complex at a different rate from that of said magnetically responsive reagent alone or from that of said mobile solid phase reagent alone or said first complex; and (c) measuring the degree of the manifestation to provide a measure of the presence or amount of said analyte in said test sample.

24. The method of claim 23, wherein said test sample is sequentially contacted with said mobile solid phase reagent and said magnetically responsive reagent.

25. The method of claim 23, wherein said test sample is simultaneously contacted with said mobile solid phase reagent and said magnetically responsive reagent.

26. The method of claim 23, wherein the degree of manifestation is determined by detecting an apparent weight change of said attached magnetically responsive reagent in said magnetic field.

27. The method of claim 26, wherein a balance is used to detect said apparent weight change.

28. The method of claim 23, wherein a visual device is used to determine said degree of manifestation.

29. The method of claim 23, wherein an optical device is used to determine said degree of manifestation.

30. The method of claim 23, wherein a position sensing device is used to determine said degree of manifestation.

31. The method of claim 23, wherein said degree of manifestation is determined visually.

32. The method of claim 23, wherein said magnetically responsive reagent comprises superparamagnetic material attached to a specific binding member.

33. The method of claim 32, wherein said superparamagnetic material is derived from a ferrofluid.

34. A method for determining the presence or amount of an analyte in a test sample, said method comprising the steps of:

(a) contacting said test sample with at least two different magnetically responsive reagents to form a reaction mixture, said analyte being capable of specifically binding to said at least two of said different magnetically responsive reagents to form a complex comprising said analyte and said at least two different magnetically responsive reagents;

(b) subjecting said reaction mixture to a magnetic field such that a magnetic force is exerted upon said complex, the influence of said magnetic force being manifested by the movement or capture of said complex at a different rate from that of said different magnetically responsive reagents alone; and (c) measuring the degree of said manifestation to provide a measure of the presence or amount of said analyte in said test sample.

35. The method of claim 34, wherein said test sample is sequentially contacted with said magnetically responsive reagents.

36. The method of claim 34, wherein said test sample is simultaneously contacted with said magnetically responsive reagents.

37. The method of claim 34 wherein the degree of manifestation is determined by detecting an apparent weight change of said attached magnetically responsive reagents in said magnetic field.

38. The method of claim 37, wherein a balance is used to detect said apparent weight change.

39. The method of claim 34, wherein a visual device is used to determine said degree of manifestation.

40. The method of claim 34, wherein an optical device is used to determine said degree of manifestation.

41. The method of claim 34 wherein a position sensing device is used to determine said degree of manifestation.

42. The method of claim 34, wherein said degree of manifestation is determined visually.

43. The method of claim 34, wherein said magnetically responsive reagents comprise superparamagnetic material attached to a specific binding member.

44. The method of claim 43, wherein said superparamagnetic material is a ferrofluid.

* * * * *

UNITED STATES PATENT AND TRADEMARK OFFICE
CERTIFICATE OF CORRECTION

PATENT NO. : 5,998,224            Page 1 of 1
DATED : December 7, 1999
INVENTOR(S) : Thomas E. Rohr et al.

It is certified that error appears in the above-identified patent and that said Letters Patent is hereby corrected as shown below:

Column 48,
Line 20, replace "superparamagnetic material is derived from a ferrofluid."
with -- superparamagnetic material is a ferrofluid. --.

Signed and Sealed this

Fourteenth Day of May, 2002

*Attest:*

*Attesting Officer*

JAMES E. ROGAN
*Director of the United States Patent and Trademark Office*